United States Patent
Reid

(10) Patent No.: US 11,022,490 B1
(45) Date of Patent: *Jun. 1, 2021

(54) METHODS AND APPARATUS FOR SPECTROSCOPIC IDENTIFICATION AND/OR CALIBRATED QUANTIFICATION OF SURFACE CONCENTRATION OF MATERIALS

(71) Applicant: Photon Systems, Inc., Covina, CA (US)

(72) Inventor: Michael R. Reid, Newport Beach, CA (US)

(73) Assignee: Photon Systems, Inc., Covina, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/904,471

(22) Filed: Jun. 17, 2020

Related U.S. Application Data

(63) Continuation of application No. 16/290,002, filed on Mar. 1, 2019, now Pat. No. 10,732,037.

(Continued)

(51) Int. Cl.
*G01J 3/02* (2006.01)
*C12Q 1/24* (2006.01)
(Continued)

(52) U.S. Cl.
CPC ............ *G01J 3/0297* (2013.01); *C12Q 1/08* (2013.01); *C12Q 1/24* (2013.01); *G01J 3/28* (2013.01); *G01J 2003/2879* (2013.01)

(58) Field of Classification Search
CPC . G01B 5/28; G01B 5/30; G01N 23/00; G01N 21/227; G01N 15/06; G01N 21/27; G06N 7/00
See application file for complete search history.

(56) References Cited

U.S. PATENT DOCUMENTS 10,732,037 B1 * 8/2020 Reid ................... G01J 3/0297
2003/0080291 A1 5/2003 Larson et al.

OTHER PUBLICATIONS

Moon, Raphael P.; Guicheteau, Jason A.; Christesen, Steven D.; Fountain, Augustus W. III; Ginter, Joy; Tokarz, John; Green, Norman; Tripathi, Ashish; Emmons, Erik; and Hung, Kevin, "Preparation of Chemical Samples on Relevant Surfaces Using Inkjet Technology", Apr. 2013, Edgewood Chemical Biological Center; U.S. Army Research, Development and Engineering Command, Aberdeen Proving Ground, MD 21010-5424.

(Continued)

*Primary Examiner* — Abdullahi Nur
(74) *Attorney, Agent, or Firm* — Dennis R. Smalley

(57) ABSTRACT

Apparatus and methods for creating deposits of uniformly spaced or uniformly overlapping droplets of selected chemicals where each droplet has an a priori known amount of the selected chemical or chemicals is taught (including biological and microbial materials). In some embodiments the deposits may be used as samples of different but known concentrations that may be used to calibrate spectroscopic inspection instruments to enable such instruments to not only provide identification in situ of unknown materials but also to provide calibrated and traceable surface concentrations of such materials. In some embodiments, such calibrated instruments may be used in enhanced processes for validating the cleanliness of manufacturing surfaces such as surfaces of equipment used in the preparation of pharmaceuticals, food, or semiconductor devices. Such instruments may be used to ensure adequate purity, or non-contamination, of surfaces of products themselves or packaging materials or of locations where such products will be used. Such calibrated instruments may also be useful in detecting cleanliness of non-manufacturing surfaces where contamination may be of concern, whether they be public or private spaces such as laboratories, restaurants, airports, satellites or other (Continued)

spacecraft. In some embodiments, such instruments may range from deep UV instruments to far infrared instruments or beyond.

20 Claims, 21 Drawing Sheets

Related U.S. Application Data

(60) Provisional application No. 62/805,748, filed on Feb. 14, 2019, provisional application No. 62/795,536, filed on Jan. 22, 2019, provisional application No. 62/637,378, filed on Mar. 1, 2018.

(51) Int. Cl.
*G01J 3/28* (2006.01)
*C12Q 1/08* (2006.01)

(56) References Cited

OTHER PUBLICATIONS

Reid, Ray, "TraC—A disruptive new hand-held rapid measurement system to verify pharma equipment surface cleanliness", International Forum on Process Analytical Chemistry, Mar. 2, 2017, Photon Systems Inc.
Reid, Michael; Hug, William; and Reid, Ray, "ChemCal, a surface cleaning validation tool for depositing pre-determined chemical concentrations, used in the calibration of surface cleaning validation tools.", International Forum on Process Analytical Chemistry, Feb. 14, 2018, Photon Systems Inc.

* cited by examiner

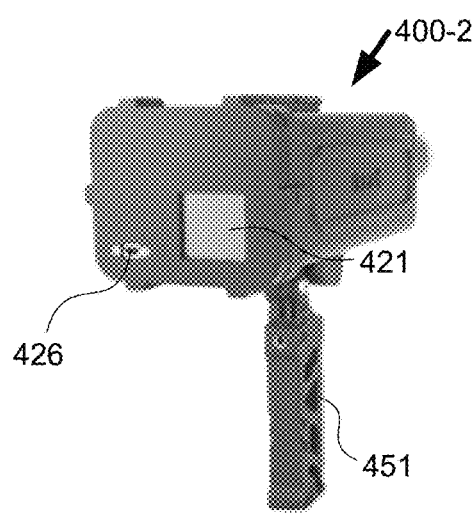
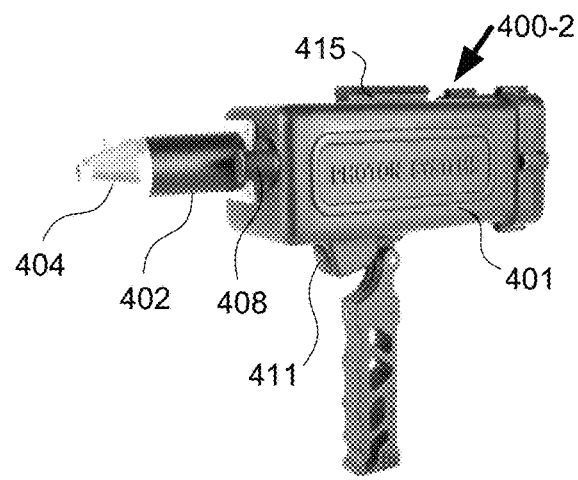
FIG. 4B-2
FIG. 4B-3
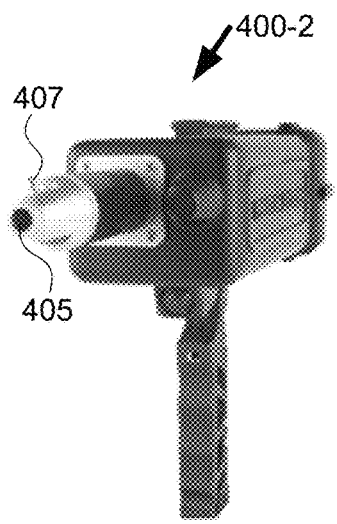
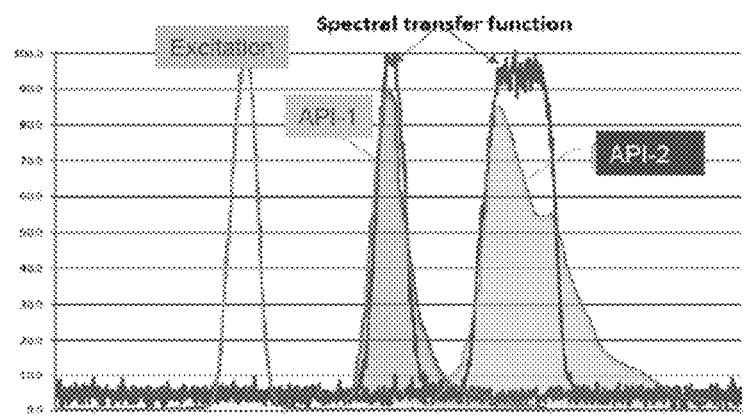
FIG. 4B-1
FIG. 4C

Deposition Pattern 1

Deposition Pattern 1

Deposition Pattern 4

Deposition Pattern 4

METHODS AND APPARATUS FOR SPECTROSCOPIC IDENTIFICATION AND/OR CALIBRATED QUANTIFICATION OF SURFACE CONCENTRATION OF MATERIALS

RELATED APPLICATIONS

This application is a continuation of U.S. patent application Ser. No. 16/290,002, filed on Mar. 1, 2019, which claims the benefit of U.S. Provisional Patent Application No. 62/805,748, filed Feb. 14, 2019; U.S. Provisional Patent Application No. 62/795,536, filed Jan. 22, 2019; and U.S. Provisional Patent Application No. 62/637,378, filed Mar. 1, 2018. Each of these applications is incorporated herein by reference as if set forth in full herein.

FIELD OF THE INVENTION

This invention relates to spectroscopic instruments and methods for performing chemical analysis and more particularly to methods and apparatus for calibrating such spectroscopic instruments such that measured spectral levels may not only be used to ascertain selected chemical or biological content but also surface or areal density (e.g. micrograms per square centimeter or $ug/cm^2$) of such selected content. In some embodiments such calibrated spectroscopic instruments may be used to provide quantitative cleanliness determination in manufacturing environments such as, for example, pharmaceutical, food, chemical, munition, semiconductor, and other manufacturing environments). In some embodiments, excitation radiation may, for example, take the form of one or more of deep UV, UV, visible, near infrared, and far infrared radiation and where measured radiation may, for example, take the form of Raman radiation, photoluminescence radiation (i.e. native fluorescence and/or phosphorescence), absorbed or unabsorbed radiation (e.g. via infra spectroscopy such as FTIR or FTNIR spectroscopy).

BACKGROUND OF THE INVENTION

Various spectroscopic methods and instruments have existed for years that can be used to perform chemical analysis and identification of materials. Such chemical analysis methods and instruments utilize, for example, Raman spectroscopy, fluorescence spectroscopy, and/or phosphorescence spectroscopy. These methods and instruments have been used in a wide range of biological and chemical research, as well as clinical, industrial, and governmental applications. These methods and instruments are being increasingly used in commercial and governmental applications such as for product inspection during the manufacture of pharmaceutical and medical products, manufactured food and chemical products, environmental testing, hazardous material detection, and other applications.

When a sample is exposed to radiation (e.g. infrared (IR) radiation, visible light, or ultraviolet (UV) radiation) at a given frequency, some of the radiation may be transmitted through the sample. Some of the radiation may be elastically scattered and retain the same frequency as the incident radiation. Some of the radiation may be absorbed in the sample. The absorbed radiation is either re-emitted after interaction with the sample or converted to thermal energy in the sample. The re-emitted radiation is sometimes referred to as inelastically scattered radiation. The inelastically scattered radiation is re-emitted as fluorescence or phosphorescence at wavelengths longer than, or frequencies lower than, the irradiation or excitation frequency, and a small fraction may be re-emitted as Raman scattered radiation. Fluorescence or phosphorescence emissions are red shifted from the excitation frequency and have a spectral distribution that is relatively independent of the excitation frequency. Raman emissions are dependent on excitation frequency and are measured as a sum or difference frequency from the excitation frequency. Absorption of radiation requires that the energy of the exciting photon be of higher energy than that of an excited state of the molecule that is being targeted. Raman emissions can be either blue (anti-Stokes) or red (Stokes) shifted from the excitation frequency by an amount determined by the rotational and vibrational bonds within the molecules being irradiated. Raman scattering efficiency is typically very low compared to fluorescence. However, when the energy of the excitation radiation corresponds to strong absorption bands of an analyte, a resonance effect can amplify the Raman signal by many orders of magnitude. Another detection method in common use uses infrared radiation and is known as Fourier Transform Infrared (FTIR) spectroscopy.

Detection and identification of materials may be one objective but when identifying trace amounts of a material on a surface another useful or even more important parameter may be the quantification of such trace material at different locations on the surface (e.g. as a surface density of the material at a given location, for example in units of nanograms (ng) or micrograms (ug) per square centimeter ($cm^2$)). Quantification may be the sole parameter of interest in situations where identify of the trace material is already known.

Traditional methods for identifying and quantifying trace chemical or biological contamination on surfaces employs:
  (1) swabbing a defined surface area,
  (2) removing the chemical or biological material from the swab using sonication in a liquid or similar process, and
  (3) examining the liquid with, for example, high performance liquid chromatography, capillary electrophoresis, mass spectrometry, or other methods which may or may not be electromagnetic spectrographic methods.

This process and variants have been employed for many decades as the standard by which chemical or biological contamination on surfaces has been determined. This process is regulated by the U.S Food and Drug Administration, and other government agencies as the gold standard for identifying and quantifying such trace materials. This process is long and tedious, takes significant manpower and equipment, and has significant short comings resulting from inherent process limitations and implementation limitations. Such flaws include inaccuracies due to losses of sample during extraction, losses during sonication, transfer to an analytical method, and the like, which causes the ultimate concentration determination to be flawed. This process is used in cleaning validation in the pharmaceutical, food, chemical, biological manufacturing businesses as well as other places where contamination of surfaces is of importance and is regulated by government or internal standards.

FIG. 1 illustrates a more detailed process flow according to an example of prior art cleaning validation processes. The process 100 starts with block 101 where it is assumed that cleaning has occurred, and that validation is to be undertaken. The process then flows to block 102 which calls for preparation of a validation cart that will be used in block 103 to move all of the materials and any necessary apparatus to the room or equipment that is to be validated. From block 103 the process moves to block 105 which calls for the use of a plurality of swabs to collect samples from defined areas to be examined. From block 105 the process moves to block 106 which calls for taking the swabs to a laboratory while 107 calls for setting up the laboratory. From block 107 the process moves to block 108 which calls for extracting the samples from the plurality of swabs while carefully controlling the handling of the swabs, or at least samples from swabs, such that associated sampling locations and samples remain correlated. Once appropriate samples have been extracted, the samples are run through HPLC analysis according to block 109 which is followed by data evaluation in block 110 and disposal of the consumed sample material in block 111. Finally, in block 112 the report on cleanliness validation is ready which may be 24, 48, or even 72 hours, or more, after the samples were originally taken. In block 113, a determination is made as to whether cleanliness requirements were met for each location, and if they have been, the process ends at block 116, but if they have not, the process moves to block 114 wherein a global or local decision on recleaning is made and implemented for at least some locations after which the process loops back into block 102 for another loop through the cleaning validation process. Of course, in the prior art, variation of this process is possible but the main take away is that the standard process in use today is manpower intensive, takes a long time, and has a slow feedback loop that limits how quickly cleaning is validated, recleaning can be performed, and the equipment or room put back into use for product production.

Significant efforts have been taken recently to update technology used in detecting concentrations on surfaces in many different application areas including cleaning validation in pharmaceutical manufacturing, control processes where cleaning is essential, trace chemical identification for antiterrorism and drug detection, and many more. Processes of most interest eliminate contact with contaminants though that may not be required in all embodiments, operate and produce results rapidly, involve little manpower, and are hopefully traceable to standards of chemical identity and concentration. These new methods are focused on optical detection methods from the deep ultraviolet to the infrared.

A problem with any method of contamination concentration detection or determination is certification of accuracy. Whether the method is swabbing, optical detection, or another method, samples of different, known concentrations need to be generated and tested to certify the accuracy of whatever method is used. Ideally, measuring of samples of known concentration for calibration purposes would be in similar form to that of the unknown samples, but this is not always the case. Sometimes, surface concentration values are inferred from readings of unknown volume concentrations of samples dissolved in solvents. Furthermore, concentrations of the known samples that have been applied to surfaces and dried have had their concentrations determined by a two-step destructive process. In such processes, a sample is first deposited onto a surface, then the sample is swabbed off the surface over a known area and analyzed via a quantifying methodology such as HPLC, where the areal concentration is determined to be the mass of the material found divided by the known area of sampling. This means that no precise calibration of a spectral analysis tool can be obtained until after measurements of the samples are made with the spectral analysis tool and the samples destroyed to provide precise quantification whereby further use of the sample to confirm continued calibration is not possible as the sample no longer exists. A more satisfactory, efficient, and timely method to achieve spectral instrument calibration is needed.

Accurate, traceable, calibration has remained elusive as uniformly deposited patterns with an a priori quantity of targeted chemicals has remained elusive. Either known quantities were obtainable without adequate uniformity or adequate uniformity could be obtained without precise knowledge of the quantity of material present. The simultaneous lack of both parameters has resulted in a failure to provide calibration samples of known surface concentration which can be used to provide direct accurate conversions between spectral signal measurements to concentration levels of materials of interest. Use of micropipettors have yielded depositions having well known sample quantities that have lacked needed uniformity. Use of spin coating has yielded uniform depositions but without adequate quantification of sample amount. Use of vapor deposition has yielded acceptable uniformity but without adequate quantification. Use of inkjet and piezo printing has also led to uniformity without adequate quantification. Inkjet printing can yield excellent XY printing resolution and accuracy when printed on absorbent surfaces with adequate uniformity of droplet placement. Yet, this technique and piezo printers have droplet sizes that are affected by many physical parameters and thus droplet volumes are not well defined and thus quantity of material deposited is not well defined. For example, surface tension and size of the droplet shot out by the printhead are inversely proportional. Surface tension of the solution is governed by nearly all of the parameters within the solution, solvent type, solute, solute concentration, temperature, and trace contaminants. Because these droplet sizes vary while an area that the printer prints on remains constant, the concentration per unit area changes. Additionally, there are other parameters that change the droplet size, for example the headspace of the sample in the printer cartridge effects the sizes of the deposits. Usually in the beginning when the cartridge is full, the system makes larger deposits, and when the system is less full, the deposits are smaller. Even if a user finds the solvent and solute ratio and verifies the settings on one day, then prints on another day, temperature and humidity changes may cause the system to introduce excess variation into the deposited volume and thus the deposited amount.

A need exists for methods and instruments for providing a plurality of calibration articles of adequate size and known concentration via either completely uniform distribution of material or of sufficiently uniform distributions of material, for example by depositing a plurality of spaced or overlapping droplets of known size having known volume concentrations of sample material such that the reading of articles provides calibration data at a number of different surface concentrations so that calibration curves can be created and used to provide quantitative determination of surface concentrations of materials of interest for a given spectral instrument when investigating regions of unknown surface concentration.

SUMMARY OF THE INVENTION

It is an object of some embodiments of the invention to provide an improved method and/or an improved device capable of creating deposits of uniform distributions of known (e.g. a priori known) quantities of one or more selected chemicals.

It is an object of some embodiments of the invention to use such deposits of materials as samples of known areal concentration from which measurements can be made by a radiation sensing instrument to derive calibration data for correlating instrument readings to known areal concentration levels.

It is an object of some embodiments of the invention to use such deposits to confirm continued calibration of a previously calibrated instrument.

It is an object of some embodiments of the invention to use such calibrated instruments to perform rapid surface cleaning validation (e.g. within an hour or two for a plurality of points or areas, more preferably within a few minutes for a plurality of points, and most preferably within a few seconds for a single point or even a plurality of points) in a manufacturing environment (e.g. for pharmaceutical production, food production, semiconductor production, or other production where contaminates must be avoided or minimized).

It is an object of some embodiments of the invention to use such calibrated instruments and associated procedures to replace swabbing procedures to provide improved cleanliness testing and validation.

It is an object of some embodiments of the invention to provide improved methods for developing new swabbing protocols.

It is an object of some embodiments of the invention to provide improved methods for training swabbing personnel that provide more rapid feedback on swabbing success.

It is an object of some embodiments of the invention to provide known quantities of selected chemicals over known areas that may be used in one or more products or processes where known concentrations of the material are important (e.g. calibration kits).

It is an object of some embodiments of the invention to provide continual, periodic, question based, or after cleaning based confirmation of cleanliness/non-contamination of a working surface or of the surface of a product that is being produced or packaged.

It is an object of some embodiments of the invention to provide a cleanliness determination on point-by-point basis, or region-by-region basis and to reach a "clean" conclusion within 10 minutes, more preferably within 5 minutes, even more preferably within 2 minutes, and most preferably within 1 minute or even tens of seconds or less. Alternatively, it is an object of some embodiments of the invention to reach a "re-clean" decision within the above noted time periods. It is even further an object of some embodiments, to implement a detection, issue a reclean decision, perform recleaning, and initiate remeasurement of cleanliness within the time periods noted above plus the actual time needed for cleaning and surface drying. It is even a further object of some embodiments, to perform the above noted determinations within the indicated times along with using calibration samples one or more times before and after reading areas of unknown concentration to validate that the instrument has remained in calibration throughout the process of reading areas of unknown concentration.

It is an object of some embodiments of the invention to use such calibrated instruments in research activities such as, for example, sublimation of chemicals of interest, oxidative damage of chemicals of interest, photo-stability of chemicals of interest, temperature stability of chemical of interest, changes in chemistry due to presence of solvents, other chemicals, and the like.

Other objects and advantages of various aspects of the invention will be apparent to those of skill in the art upon review of the teachings herein. The various aspects of the invention, set forth explicitly herein or otherwise ascertained from the teachings herein, may address any one of the above objects alone or in combination, or alternatively may address some other object of the invention ascertained from the teachings herein. It is not intended that any specific aspect of the invention (that is explicitly set forth below or that is ascertained from the teachings herein) necessarily address any of the objects set forth above let alone address all of these objects simultaneously, but some aspects may address one or more of these objects or even all of these objects simultaneously.

In a first aspect of the invention, a method for cleaning verification, cleaning validation, contaminate detection, or intended material detection examines an item selected from the group consisting of (1) at least one piece of equipment, (2) at least one room, (3) at least one room and at least one piece of equipment, (4) at least one work product, and (5) a surface of any of (1)-(4), wherein the method includes: (a) providing a spectroscopic surface analysis instrument, including: (i) a housing; (ii) a source in the housing that is capable of producing and directing radiation onto a surface to be examined; (iii) at least one optical element within the housing for receiving emission radiation from a location on a surface undergoing examination; (iv) a detector within the housing for receiving at least a portion of the emission radiation coming from the location; and (v) control electronics for operating the instrument; (b) providing an electronic circuit, comprising at least one programmed processor and a memory, for determining whether emission radiation corresponds to at least one material selected from the group consisting of (1) a single selected material of interest or (2) a plurality of selected materials of interest and wherein a determination can be made that is selected from the group consisting of (1) a concentration of such a selected material (e.g. areal concentration), (2) concentration of such a selected material is above a predefined level and (3) concentration of such a selected material is below a predefined level; (c) operating the surface analysis instrument to provide emission radiation from at least one location and detection thereof; (d) operating the electronic circuit to determine a level of the at least one material at the at least one location; and (e) based on the determination, providing at least one indication associated with detection status at the at least one location, wherein the spectroscopic surface analysis instrument is provided with calibration data obtained by using the spectroscopic instrument to detect emission radiation from at least one set of calibration samples created by the dispensing of uniformly spaced fluid droplets of known volume and chemical concentration of at least one selected material on at least one substrate and the detected emission radiation from the at least one set of calibration samples is used to provide the calibration data over a useful range of surface concentrations for the at least one selected material and the calibration data is used in providing calibrated information from the instrument.

In a second aspect of the invention, a method for cleaning verification, cleaning validation, contaminate detection, or intended material detection examines an item selected from the group consisting of (1) at least one piece of equipment, (2) at least one room, (3) at least one room and at least one piece of equipment, (4) at least one work product, and (5) a surface of any of (1)-(4), wherein the method includes: (a) providing a spectroscopic surface analysis instrument, including: (i) a housing; (ii) a source in the housing that is capable of producing and directing radiation onto a surface to be examined; (iii) at least one optical element within the housing for receiving emission radiation from a location on a surface undergoing examination; (iv) a detector within the housing for receiving at least a portion of the emission radiation coming from the location; and (v) control electronics for operating the instrument; (b) providing an electronic circuit, comprising at least one programmed processor and a memory, for determining a concentration level associated with emission radiation from a selected material, wherein the concentration level is selected from the group consisting of (1) an actual concentration (e.g. areal concentration), (2) identifying that the concentration is above a predefined level, and (3) identifying that the concentration is below a predefined level; (c) operating the surface analysis instrument to provide emission radiation from at least one location and detection thereof; (d) operating the electronic circuit to determine a level of the material at the at least one location; and (e) based on the determination, providing at least one indication associated with detection status at the at least one location, wherein the spectroscopic surface analysis instrument is provided with calibration data obtained by using the spectroscopic instrument to detect emission radiation from at least one set of calibration samples created by the dispensing of uniformly spaced fluid droplets of known volume and chemical concentration of at least one selected material on at least one substrate and the detected emission radiation from the at least one set of calibration samples is used to provide the calibration data over a useful range of surface concentrations for the at least one selected material and the calibration data is used in providing calibrated information from the instrument.

Numerous variations of the first and/or second aspects of the invention exist and include for example: (1) the methods of either aspect wherein an amount of at least one selected chemical in each droplet being known a priori; (2) the methods of either aspect or of the previous variation where the droplets are dispensed at selected locations on an XY grid by a computer-controlled syringe, having a dispensing needle, from a fluid volume having known volumetric concentration of the at least one selected material; (3) the method of variation (2) including a digital syringe; (4) the methods of either aspect or any of the previous variations wherein multiple droplets are dispensed to the same XY location to increase the amount of the at least one selected material at that location; (5) the method of variation (4) wherein the plurality of droplets of variation (4) are dispensed at each of a plurality of locations wherein dispensing occurs with a timing selected from the group consisting of: (a) a subsequent droplet being dispensed on a given location while a previously dispensed droplet at the given location remains, at least in part, in a fluid state, and (b) a subsequent droplet being dispensed on a given location after all previously dispensed droplets contacting that location have dried such that an associated at least one selected material has become solid at the given location, and (c) a subsequent droplet being dispensed on a given location after all previously dispensed droplets, with the possible exception of one or more droplets dispensed in exactly the same location, contacting that location have dried such that an associated at least one selected material has become solid at the given location.

A sixth variation of the first and/or second aspects and any of their previously presented variations exist and include, for example: the droplets being dispensed to each of a plurality of dispensing locations being dispensed using a process selected from the group consisting of: (1) (i) while a tip of the needle of the syringe is located at a Z-level above a surface of a substrate, positioning the needle to an XY dispensing location (if not already there), (ii) lowering the needle until contact with the substrate is made, (iii) operating the syringe to dispense a droplet having a defined fluid volume containing a known concentration of at least one selected material, (iv) lifting the needle along the axis above the substrate, so that the droplet is released and such that the needle tip is at a height for XY movement to a next dispensing location, and (v) repeating (i) to (iv) to dispense a plurality of droplets at a plurality of locations; (2) (i) while a tip of the needle of the syringe is located at a Z-level above a surface of a substrate, positioning the needle to an XY dispensing location (if not already there), (ii) lowering the needle until contact with the substrate is made, (iii) raising the needle above the surface of the substrate by an amount that is less than a diameter of an unreleased droplet, (iv) operating the syringe to dispense a droplet having a defined fluid volume containing a known concentration of at least one selected material such that the volume comes in contact with the substrate prior to losing contact with the needle; (v) lifting the needle in Z away from the substrate, wherein the release of the droplet from the needle to the substrate occurs during a step selected from the group consisting of step (iv) as the syringe is being operated (i.e. the droplet is being formed) and step (v) as the needle is being lifted away from the substrate, and (vi) repeating (i) to (v) to dispense a plurality of droplets at a plurality of locations; (3) (i) while a tip of the needle of the syringe is located at a Z-level above a surface of a substrate, positioning the needle to an XY dispensing location (if not already there), (ii) lowering the needle until the tip of the needle is located above the substrate by a distance that is less than a diameter of a droplet to be dispensed, (iii) operating the syringe to dispense a droplet having a defined fluid volume containing a known concentration of at least one selected material such that the volume comes in contact with the substrate prior to losing contact with the needle, (iv) lifting the needle along the Z direction, wherein the release of the droplet from the needle to the substrate occurs during a step selected from the group consisting of step (iii) as the syringe is being operated (i.e. droplet is being formed) and step (iv) as the needle is being lifted away from the substrate, and (v) repeating (i) to (iv) to dispense a plurality of droplets at a plurality of locations; (4) (i) while a tip of the needle of the syringe is located at a Z-level above a surface of a substrate, positioning the needle to an XY dispensing location (if not already there), (ii) operating the syringe to dispense a droplet having a defined fluid volume containing a known concentration of at least one selected material, (iii) lowering the needle until the tip of the needle is located above the substrate by a distance that is less than a diameter of the dispensed droplet, (iv) lifting the needle along the Z direction, wherein the release of the droplet from the needle to the substrate occurs during a step selected from the group consisting of step (ii), step (iii) and step (iv), and (v) repeating (i) to (iv) to dispense a plurality of droplets at a plurality of locations; and (5) the process of any of (1)-(4) wherein each of a plurality of successive XY droplet dispensing locations is spaced from an immediately preceding XY droplet dispensing location by a distance such that two successively dispensed droplets do not touch one another when making contact with the substrate.

Still other variations include, for example: (7) the methods of either aspect or any of their previous variations wherein a nominal diameter of each of a plurality of droplets prior to dispensing is selected from a group consisting of: (a) between 0.05 mm and 5 mm, (b) between 0.1 mm and 3 mm, and (c) between 0.1 and 1 mm; (8) the methods of either aspect or any of their previous variations wherein a nominal diameter of each of a plurality of deposited drops is selected from a group consisting of: (a) between 0.1 mm and 5 mm, (b) between 0.2 mm and 2 mm, and (c) between 0.5 and 1.5 mm; (9) the methods of either aspect or any of their previous variations wherein the spacing between a plurality of successive XY dispensing locations is selected from a group consisting of: (a) between 0.1 mm and 10 mm, (b) between 0.2 mm and 5 mm, and (c) between 0.5 mm and 1.2 mm; (10) the methods of either aspect or any of their previous variations wherein an effective measurement diameter of the instrument is selected from a group consisting of: (a) between 0.5 mm and 15 mm, (b) between 1 mm and 10 mm, (c) between 1 mm and 5 mm, and (d) between 2.0 mm and 4.0 mm; (11) the methods of either aspect or any of their previous variations wherein the at least one set of calibration samples is not destroyed in the process of providing a calibration of the instrument; (12) the method of variation (11) wherein the at least one set of calibration samples is used after the instrument provides at least one indication using the original calibration information to confirm that the instrument remains within an acceptable calibration tolerance (e.g. 0.5 to 2.0, 0.5 to 1.5, or 0.75 to 1.25 of the original calibration); (13) the methods of either aspect or any of their previous variations wherein each calibration sample is provided with a single concentration of at least one selected chemical and wherein each such calibration sample is provided on its own separate substrate; (14) the methods of either aspect or any of their previous variations wherein the at least one set of calibration samples is provided by a chemical printer that provides at least one computer-controlled stage for relative XY movement of a printhead carrying the syringe needle and at least one substrate onto which calibration samples are printed; (15) the method of variation (13) wherein the XY position of the printhead is confirmed periodically by running a printhead that carries the syringe needle back to a known position, such as X=0, Y=0, as defined by X and Y sensors (e.g. limit switches) after which, control parameters (such as X and Y motor controller values) are reset to selected values; (16) the methods of either aspect or of any of their previous variations wherein the at least one selected material forms a solution of known concentration after it is dissolved in a solvent and wherein after depositing a droplet, the solvent evaporates from the at least one selected material to leave a dried deposit; (17) the methods of either aspect or of any of their previous variations wherein the at least one selected material forms a suspension when mixed with a liquid and wherein the suspension is maintained at a uniform dispersion by a method selected from the group consisting of: (a) vibrating, (b) shaking, (c) mixing, (d) stirring, (e) magnetic stirring, and (f) pumping; (18) the method of the first aspect and of any previous variation associated therewith wherein the instrument is calibrated prior to making in situ measurements of unknown materials such that in situ measurements are provided in calibrated form; (19) the methods of either aspect or of any of their previous variations wherein the data from in situ measurements are gathered and then calibration factors applied to the in-situ measurements; (20) the methods of either aspect or of any of their previous variations wherein the calibration samples are printed directly onto an in-situ surface; (21) the method of variation (14) wherein the printer is configured to hold multiple samples of liquids containing known concentrations of at least one selected material which can be used by the syringe in depositing different droplets; (22) the method of variation (21) wherein a plurality of droplets are dispensed during the formation of a first calibration sample using liquid from one sample container and a plurality of other droplets are dispensed using a liquid from another sample container in forming a calibration sample selected from the group consisting of (a) the first calibration sample and (b) a different calibration sample; (23) the method of variation (22) wherein two calibration samples are produced using a single selected material with each calibration sample providing a different areal concentration of the selected material; (24) the method of variation (22) wherein a single calibration sample is produced having a mixture of two different selected materials each having a defined areal concentration; (25) the methods of any of variations (21)-(24) wherein prior to using the syringe to hold and dispense a second selected material of at least two different materials, the syringe is purged of a first material and rinsed prior taking in a quantity of the second selected material that will be used in forming calibration samples; (26) the method of variation (25) wherein the purging and rinsing comprises a process of: (a) emptying the first material from the syringe into a waste receptacle, (b) loading a third fluid into the syringe at least once and emptying the syringe of the third fluid prior to loading in the fluid containing the second material that will be used in making a calibration sample, wherein the second fluid is selected from the group consisting of (a) a solvent and (b) a fluid containing the same material as the second selected material but extracted from a different container to avoid contamination; (27) the methods of either aspect or any of their previous variations wherein the item is located in a facility selected from the group consisting of: (a) a pharmaceutical processing facility, (b) a food processing facility, (c) an explosives processing facility, (d) a nanoparticle processing facility, (e) a semiconductor processing facility, (f) a research laboratory; (g) a manufacturing facility, (h) a sorting facility, and (i) a transportation facility; (28) the methods of either aspect or any of their previous variations wherein the item is further selected from a group consisting of: (a) an ingredient processing machine, (b) an ingredient mixing machine, (c) a packaging machine, (d) a transportation machine, (e) a vehicle, and (f) a dispensing machine; (29) the methods of either aspect or any of their previous variations wherein one or more materials of interest, comprise a material selected from the group consisting of (a) an active pharmaceutical ingredient (API), (b) an excipient, (c) a pharmaceutical drug, (d) a food or food ingredient, (e) an explosive or explosive ingredient, (f) a toxic material, (g) a bacteria, (h) a virus, (i) a cleaning material, and (j) an organic material.

Further variations include: (30) the methods of either aspect or any of their previous variations wherein the source is selected from the group consisting of: (a) a laser, (b) a hollow cathode laser, (c) a semiconductor laser, (d) a triode, (e) a diode, and (f) an arc lamp; (31) the methods of either aspect or any of their previous variations wherein the radiation has a wavelength selected from the group consisting of (a less than 350 nm, (b) less than 300 nm, (c) less than 280 nm, and (d) less than 250 nm; (32) the methods of either aspect or any of their previous variations wherein the emission radiation comprises radiation selected from the group consisting of: (a) fluorescence emission from a doping source; (b) native fluorescence emission, (c) phosphorescence emission, (d) Raman emission, and (e) non-absorbed radiation; (33) the methods of either aspect and any of variations (1)-(29) wherein the instrument provides detection via FTIR analysis; (34) the methods of either aspect or any of their previous variations wherein the at least one optical element comprises an element selected from the group consisting of: (a) at least one filter, (b) at least one band pass filter, (c) at least one diffraction grating, (d) a least one prism, (e) at least one lens, (f) at least one mirror, and (g) at least one quartz window; (35) the methods of either aspect or any of their previous variations wherein the detector comprises an element selected from the group consisting of: (a) at least one photodiode, (b) at least one photomultiplier tube (PMT), (c) at least one charge coupled device (CCD), and (d) a CCD array; (36) the methods of either aspect or any of their previous variations wherein the instrument also includes at least one battery, held within the instrument housing for powering the instrument; (37) the methods of either aspect or any of their previous variations wherein the instrument has a weight selected from the group consisting of (a) under 8 pounds, (b) under 4 pounds, and (c) under 2 pounds; (38) the methods of either aspect or any of their previous variations wherein the dimensions of the instrument housing (exclusive of any handle) are selected from the group consisting of (a) a length under 20 inches, (b) a length under 16 inches, (c) a length under 12 inches; (d) a width under 15 inches, (e) a width under 10 inches, (f) a width under 5 inches, (g) a height under 15 inches, (h) a height under 10 inches, and (i) a height under 5 inches; (39) the methods of either aspect or any of their previous variations wherein the housing of the instrument is connected to a collapsible handle; (40) the methods of either aspect or any of their previous variations wherein the control electronics of the instrument comprises at least one control input device for operating the instrument selected from the group consisting of: (a) a control panel, (b) at least one switch, (c) a touch screen, (d) a button, (e) a sensor, (f) a microphone, (g) a tethered connection to a separate electronic device, and (h) a wireless connection to a separate electronic device; (41) the methods of either aspect or any of their previous variations wherein the control electronics comprises at least one device selected from the group consisting of: (a) a microprocessor for controlling the system and processing data, (b) a memory for storing selected data, (c) a ROM for storing a boot program and data, (d) a display screen for displaying information, (e) an output for transferring data to another electronic device via a wired connection, (f) wireless communication electronics for transmitting data to a separate electronic device, (g) an input port for receiving data from a separate electronic device via a wired connection, and (h) wireless communication electronics for transmitting data to another electronic device; (42) the methods of either aspect or any of their previous variations wherein the instrument further comprises one or more components selected from the group consisting of: (a) internal wireless battery charging circuitry, (b) internal cabled battery charging circuitry; (c) a camera for recording surface images at the at least one detection location, and (d) sensors for supplying position and/or orientation information when obtaining emission information; (43) the methods of either aspect or any of their previous variations wherein the electronic circuit is located within the housing and forms part of the instrument; (44) the methods of either aspect or any of their previous variations wherein the control electronics are provided by an electronic circuit which is located within the housing; (45) the methods of either aspect and any of variations (1)-(43) wherein the electronic circuit is located external to the instrument and communication between the instrument and the electronic circuit occurs while data from emission radiation is being gathered; (46) the methods of either aspect and any variations (1)-(43) wherein the electronic circuit is located external to the instrument and communication between the instrument and the electronic circuit occurs between data gathering events associated with receiving emission radiation; (47) the methods of either aspect and any of variations (1)-(43) wherein the electronic circuit is located external to the instrument and communication between the instrument and the electronic circuit occurs after data gathering for a plurality of locations is completed; (48) the methods of first aspect and any variations proceeding therefrom wherein spectral information gathered for a given location is compared to a spectral information library associated with at least one material of interest to determine the presence of the at least one material as indicated by the spectral data gathered from the location; (49) the methods of either aspect or any of their previous variations wherein magnitude information associated with the data gathered from that at least one location is compared to calibration information to determine a concentration level of the at least one material at the given location; (50) the method of variation (49) wherein the predetermined level is a concentration level measured in mass/area (e.g. micrograms/cm$^2$); (51) the methods of either aspect or any of their previous variations wherein the instrument is capable of detecting concentrations levels for the one or more materials of interest at levels selected from the group consisting of: (a) <=1 milligram (mg)/cm$^2$, (b) <=100 micrograms (ug)/cm$^2$, (c) <=10 ug/cm$^2$, (d) <=1 ug/cm$^2$, (e) <=100 nanograms (ng)/cm$^2$, (f) <=10 ng/cm$^2$, and (g) <=1 ng/cm$^2$; (52) the methods of either aspect or any of their previous variations wherein a test time per location is selected from the group consisting of: (a) <1 minute per location, (b) <10 seconds per location, and (c) <1 second per location; (53) the methods of either aspect or any of their previous variations wherein a data processing time per location, per material of interest is selected from the group consisting of (a) <1 hour, (b) <10 minutes, (c) <1 minute per location, (d) <10 seconds per location, and (e) <1 second per location; (54) the methods of either aspect or any of their previous variations wherein a standoff height, H, between a surface to be examined and a proximal end of the instrument is selected from the group consisting of (a) 0 cm <H<=1 cm, (b) 0 cm<H<=2 cm, (c) 1 cm<=H<=2 cm, (d) 0 cm<H<=4 cm, (e) 2 cm<=H<=4 cm, (f) 4 cm<=H<=8 cm, and (g) 0 cm<=H; (55) the method of the first aspect and any variations associated therewith wherein the probability of not identifying a material of interest that is present is selected from the group consisting of (a) <10%, (b) <5%, and (c) <1%, while the specificity of identification is selected from the group consisting of (a) >90%, (b) >95%, and (3) >99%, while the probability of misidentifying a detected material of interest as being below a specified limit is selected from the group consisting of (a) <5%, (b) <1%, (c) <0.1%; (56) the methods of either aspect or any of their previous variations wherein the method provides cleanliness validation and the predefined level defines a boundary between a surface that is sufficiently clean and one that is not; (57) the methods of either aspect or any of their previous variations wherein the at least one location comprises a plurality of locations; (58) the methods of either aspect or any of their variations wherein the spectroscopy instrument is operated to take at least some measurements with the instrument touching the surface that is being measured (i.e. the instrument is operated in a contact mode); and (59) the methods of either aspect or any of their variations wherein the spectroscopy instrument is operated to take at least some measurements with the instrument not touching the surface that is being measured (i.e. the instrument is operated in a non-contact mode).

In a third aspect of the invention a method of calibrating a spectroscopic surface analysis instrument provides not only identification of trace materials of interest but also provides quantitative indications of concentrations of one or more materials of interest, and includes: (a) providing a spectroscopic surface analysis instrument, including: (i) a housing; (ii) a source in the housing that is capable of producing and directing radiation onto a surface to be examined; (iii) at least one optical element within the housing for receiving emission radiation from a location on a surface undergoing examination; (iv) a detector within the housing for receiving at least a portion of the emission radiation coming from the location; and (v) control electronics for operating the instrument; (b) providing an electronic circuit, comprising at least one programmed processor and a memory, for determining whether emission radiation corresponds to at least one material selected from the group consisting of: (1) a single selected material of interest, and (2) a plurality of selected materials of interest, and wherein a determination can be made that is selected from the group consisting of: (1) a concentration of such a selected material (e.g. areal concentration), (2) concentration of such a selected material is above a predefined level, and (3) concentration of such a selected material is below a predefined level; (c) providing an electronic circuit for creating and storing quantitative calibration data; (d) operating the instrument in a calibration mode, including: (i) operating the surface analysis instrument to provide excitation radiation on to a plurality of sample surfaces, in a serial manner, with each sample having a known material with at least one known concentration; (ii) collecting data from the emission radiation being returned from each sample while a proximal end of the instrument is located within a known spatial separation distance from each sample; and (iii) processing the data obtained to provide calibration data for a desired range of concentrations of a specific material; whereby upon use of the instrument to examine a surface to be tested, which may have an unknown material thereon, obtained emission radiation may be compared to the calibration data to ascertain information about the type and quantity of material of interest that is present.

In a forth aspect of the invention a method of calibrating a spectroscopic surface analysis instrument provides quantitative indications of concentrations of one or more materials of interest, and includes: (a) providing a spectroscopic surface analysis instrument, including: (i) a housing; (ii) a source in the housing that is capable of producing and directing radiation onto a surface to be examined; (iii) at least one optical element within the housing for receiving emission radiation from a location on a surface undergoing examination; (iv) a detector within the housing for receiving at least a portion of the emission radiation coming from the location; and (v) control electronics for operating the instrument; (b) providing an electronic circuit, comprising at least one programmed processor and a memory, for determining a concentration level associated with emission radiation from a selected material, wherein the concentration level is selected from the group consisting of (1) an actual concentration (e.g. areal concentration), (2) identifying that the concentration is above a predefined level, and (3) identifying that the concentration is below a predefined level; (c) providing an electronic circuit for creating and storing quantitative calibration data; (d) operating the instrument in a calibration mode, including: (i) operating the surface analysis instrument to provide excitation radiation on to a plurality of sample surfaces, in a serial manner, with each sample having a known material with at least one known concentration; (ii) collecting data from emission radiation being returned from each sample while a proximal end of the instrument is located within a known spatial separation distance from each sample; and (iii) processing the data obtained to provide calibration data for a desired range of concentrations of a specific material; whereby upon use of the instrument to examine a surface to be tested, which may have an unknown material thereon, obtained emission radiation may be compared to the calibration data to ascertain information about the quantity of material of interest that is present.

Numerous variations to the third and/or fourth aspects are possible and include for example: (1) the calibration data comprising a list of data points obtained from operating in the calibration mode; (2) the calibration data comprising a list of the average values of data obtained for each concentration value; (3) the calibration data comprising a best fit plot of signal strength vs. concentration; (4) the signal strength of the data from the sample of the material of interest of unknown concentration being matched to the corresponding signal strength of the calibration data from which a concentration, or relative concentration, of the sample may be extracted; and (5) each of the variations, mutatis mutandis, set forth above with respect to the first and/or second aspects and variations associated therewith.

In a fifth aspect of the invention a device for printing known concentrations of a material, includes: (a) a printer with a substrate and a printhead capable of relative XYZ movement with respect to the substrate; (b) at least one computer-controlled syringe mounted to the head and capable of dispensing known volumes and concentrations (mass/volume) of one or more materials of interest; (c) a control system configured for operating the printer to dispense the at least one material from the at least one syringe to at least one surface so that a desired surface concentration of material is deposited; wherein the controller relatively moves the syringe horizontally (in XY) to a desired print location and then vertically (in Z) so that a tip of the syringe, or at least a droplet of material extending from the tip, contacts the surface whereby a known volume of known volume concentration is dispensed onto the surface and the tip is then moved vertically away from the surface, wherein the relative horizontal and relative vertical movements and the dispensing is repeated to deposit a plurality of droplets onto the at least one surface In a sixth aspect of the invention a device for printing samples of known concentrations of a material, includes: (a) a printer with a substrate and a printhead capable of relative XYZ movement relative to the substrate; (b) at least one computer controlled syringe mounted to the printhead and capable of dispensing known volumes and concentrations (mass/volume) of at least one material of interest; (c) a control system configured to operate the printer to print a plurality of droplets of the material while in solution from the at least one syringe to a plurality of defined X and Y locations on at least one surface so that a precise amount of the material is deposited over a given area to provide a known uniform average areal concentration of the at least one material after a fluid portion of the solution evaporates living a dried deposit of the material, wherein the controller relatively moves the syringe horizontally (in X and Y) to desired print locations, operates the syringe to expel known volumes of the material, moves the syringe vertically (in Z) so that a tip of the syringe, or at least a droplet of material extending from the tip contacts the surface after which the tip is raised which results in a known volume of known concentration being is dispensed onto the surface and the syringe being in a position for further horizontal movements and dispensing operations as necessary to complete formation of the sample on the surface.

Numerous alternatives to the fifth and/or sixth aspects of the invention are possible and include for example: (1) the surface being segmented into separate coupons; (2) the device of variation (1) where a plurality of coupons are printed with different areal concentrations of the material; (3) the device of either variation (1) or (2) where a plurality of coupons are made of different materials; (4) the device of any of variations (1)-(3) wherein a plurality of coupons have different surface textures; (5) the device of any of variations (1)-(4) wherein a plurality of coupons have different surface perforation or hole patterns; (6) the device of either aspect or any of the previously noted variations wherein an amount of the material in each dispensed droplet is known a priori; (7) the device of either aspect or any of the previously noted variations wherein the droplets are dispensed at selected locations on an XY grid by a computer-controlled syringe, having a dispensing needle; (8) the device of either aspect or any of the previously noted variations wherein the computer-controlled syringe comprises a digital syringe; (9) the device of either aspect or any of the previously noted variations wherein the printer is programmed to dispense multiple droplets to the same XY location to increase the amount of the at least one selected material at that location; (10) the device of either aspect or any of the previously noted variations wherein the printer is programmed to dispense multiple droplets in proximity to one another such that partial droplet overlap occurs; (11) the device of either of the aspects or any of the previously noted variations wherein the printer is programmed to dispense a plurality of droplets that may overlap with other dispensed droplets with a timing that results in previously dispensed droplets being in a non-fluid state at the time the plurality of potentially overlapping droplets are dispensed; (12) the device of either aspect or any of the previously noted variations wherein the printer is programmed to dispense a plurality of droplets that may overlap with other dispensed droplets with a timing that results in previously dispensed droplets being in a dried state at the time the plurality of potentially overlapping droplets are dispensed.

A thirteenth (13) variation of the fifth and sixth aspects and any of their previously presented variations exists and includes, for example: programming of the printer such that the dispensing of droplets to each of a plurality of dispensing locations occurs using a computer controlled process that implements steps selected from the group consisting of: (1) (i) while a tip of the needle of the syringe is located at a Z-level above a surface of a substrate, positioning the needle to an XY dispensing location (if not already there), (ii) lowering the needle until contact with the substrate is made, (iii) operating the syringe to dispense a droplet having a defined fluid volume containing a known concentration of at least one selected material, (iv) lifting the needle along the axis above the substrate, so that the droplet is released and such that the needle tip is at a height for XY movement to a next dispensing location, and (v) repeating (i) to (iv) to dispense a plurality of droplets at a plurality of locations; (2) (i) while a tip of the needle of the syringe is located at a Z-level above a surface of a substrate, positioning the needle to an XY dispensing location (if not already there), (ii) lowering the needle until contact with the substrate is made, (iii) raising the needle above the surface of the substrate by an amount that is less than a diameter of an unreleased droplet, (iv) operating the syringe to dispense a droplet having a defined fluid volume containing a known concentration of at least one selected material such that the volume comes in contact with the substrate prior to losing contact with the needle; (v) lifting the needle in Z away from the substrate, wherein the release of the droplet from the needle to the substrate occurs during a step selected from the group consisting of step (iv) as the syringe is being operated to form the droplet) and step (v) as the needle is being lifted away from the substrate, and (vi) repeating (i) to (v) to dispense a plurality of droplets at a plurality of locations; (3) (i) while a tip of the needle of the syringe is located at a Z-level above a surface of a substrate, positioning the needle to an XY dispensing location (if not already there), (ii) lowering the needle until the tip of the needle is located above the substrate by a distance that is less than a diameter of a droplet to be dispensed, (iii) operating the syringe to dispense a droplet having a defined fluid volume containing a known concentration of at least one selected material such that the volume comes in contact with the substrate prior to losing contact with the needle, (iv) lifting the needle along the Z direction, wherein the release of the droplet from the needle to the substrate occurs during a step selected from the group consisting of step (iii) as the syringe is being operated to form the droplet and step (iv) as the needle is being lifted away from the substrate, and (v) repeating (i) to (iv) to dispense a plurality of droplets at a plurality of locations; (4) (i) while a tip of the needle of the syringe is located at a Z-level above a surface of a substrate, positioning the needle to an XY dispensing location (if not already there), (ii) operating the syringe to dispense a droplet having a defined fluid volume containing a known concentration of at least one selected material, (iii) lowering the needle until the tip of the needle is located above the substrate by a distance that is less than a diameter of the dispensed droplet, (iv) lifting the needle along the Z direction, wherein the release of the droplet from the needle to the substrate occurs during a step selected from the group consisting of step (ii), step (iii) and step (iv); and (v) repeating (i) to (iv) to dispense a plurality of droplets at a plurality of locations; and (5) the process of any of (1)-(4) wherein each of a plurality of successive XY droplet dispensing locations is spaced from an immediately preceding XY droplet dispensing location by a distance such that two successively dispensed droplets do not touch one another when making contact with the substrate.

Additional alternatives to the fifth and sixth aspects of the invention are possible and include for example: (14) the device of either aspect or any of their previously presented variations wherein a nominal diameter of each of a plurality of un-released droplets is selected from a group consisting of: (a) between 0.05 mm and 5 mm, (b) between 0.1 mm and 3 mm, and (c) between 0.1 and 1 mm; (15) the device of either aspect or any of their previously presented variations wherein a nominal diameter of each of a plurality of deposited drops is selected from a group consisting of: (a) between 0.1 mm and 5 mm, (b) between 0.2 mm and 2 mm, and (c) between 0.5 and 1.5 mm; (16) the device of either aspect or any of their previously presented variations wherein the device is programmed such that a spacing between a plurality of successive XY dispensing locations is selected from a group consisting of: (a) between 0.1 mm and 10 mm, (b) between 0.2 mm and 5 mm, and (c) between 0.5 mm and 1.2 mm; (17) the device of either aspect or any of their previously presented variations wherein the computer-controlled syringe can dispense droplets with a volume selected from (a) <200 nanoliters (nL), (b) <100 nL, (c) <50 nL, (d) <25 nL, (e) <10 nL, (f) <5 nL, and (g) <1 nL; (18) the device of either aspect or any of their previously presented variations wherein the surface concentrations are selected from the group consisting of: (a) <10 mg/cm$^2$, (b) <1 mg/cm$^2$, (c) <0.1 mg/cm$^2$, (d) <10 ug/cm$^2$, (e) <1 ug/cm$^2$, (f) <0.1 ug/cm$^2$, (g) <10 ng/cm$^2$, and (h) <1 ng/cm$^2$; and (19) the device of either aspect or any of their previously presented variations wherein the droplet dispensing rate is selected from the group consisting of (a) >100 droplets/minute, (b) >200 droplets/minute, and (c) >500 droplets/minute.

Further aspects of the invention will be understood by those of skill in the art upon review of the teachings herein. These other aspects of the invention may provide various combinations of the aspects presented above as well as provide other configurations, structures, functional relationships, and processes that have not been specifically set forth above.

BRIEF DESCRIPTION OF THE DRAWINGS

FIGS. 4B-1 to 4B-3 provide several isometric views of a spectroscopic instrument that may be used as part of or in conjunction with some embodiments of the invention.

FIG. 4C provides a plot of response vs wavelength for two sample APIs that might be produced by a spectroscopic instrument of the type of FIG. 4A.

FIG. 12A-1 provides a flowchart of a first droplet dispensing process while FIG. 12A-2 provides a schematic illustration of a device performing that droplet dispensing process wherein at the time of syringe operation (to dispense a given volume as a droplet) a needle tip of the syringe is in contact with a dispensing substrate and after dispensing, the tip of a needle of the syringe is raised to a height above the substrate that is greater than the height of an unreleased droplet.

FIG. 12B-1 provides a flowchart of a second droplet dispensing process while FIG. 12B-2 provides a schematic illustration of a device performing the droplet dispensing process wherein at the time of syringe operation (to dispense a given volume as a droplet) a tip of the dispensing needle of the syringe is above a substrate surface by an amount smaller than an unreleased droplet height where the distance is set by first touching the substrate with the needle (prior to dispensing) and then retracting the needle a desired amount to a height above the substrate that is less than a height of an unreleased droplet.

FIG. 12C-1 provides a flowchart of a third droplet dispensing process while FIG. 12C-2 provides a schematic illustration of a device performing the droplet dispensing process wherein at the time of dispensing a given volume (as a droplet) from a tip of a syringe dispensing needle, the tip is above a substrate surface by an amount smaller than a droplet height where the distance is set by moving the needle downward and stopping movement prior to the needle making contact with the substrate and then after dispensing raising the needle to a height above the substrate that is greater than the height of an unreleased droplet.

FIG. 12D-1 provides a flowchart of a fourth droplet dispensing process while FIG. 12D-2 provides a schematic illustration of a device performing the droplet dispensing process wherein at the time of dispensing a known volume (as a droplet) from a tip of a syringe dispensing needle, the tip is above a substrate surface by an amount greater than an unreleased droplet height and where after dispensing, the needle tip is lowered to a position above the substrate less than a height of the unreleased droplet after which the tip of the needle is raised away from the substrate by an amount greater than a height of an unreleased droplet.

DETAILED DESCRIPTION OF PREFERRED EMBODIMENTS OF THE INVENTION

Figure 1:
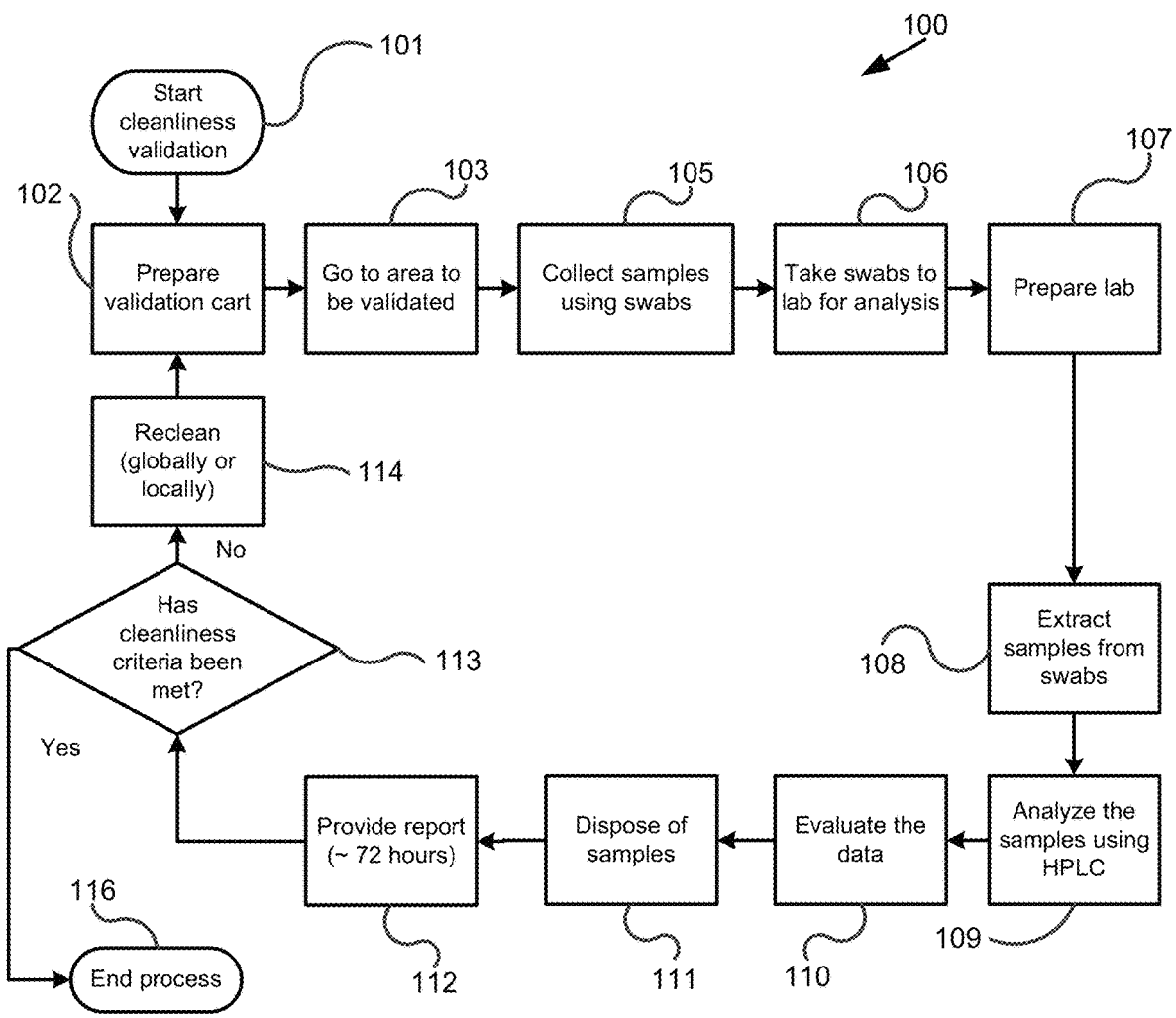
FIG. 1 provides a sample flowchart for a cleaning validation process that begins after a preliminary cleaning process has occurred.

Some embodiments of the invention relate to methods and apparatus for printing known quantities of selected materials (e.g. chemicals and biological materials) over unknown surface areas with an acceptable degree of uniformity or homogeneity relative to a measurement size where the surface areas (e.g. coupons or in situ surfaces) can be used as known values for calibrating analytic instruments.

Other embodiments of the present invention relate to calibrating analytic instruments and particularly handheld analytic instruments that will identify and/or read surface concentrations of selected materials where such instruments may be calibrated by measuring the known values as noted above and correlating resultant instrument readings with the known concentrations. In some embodiments, the calibration of the analytic instrument may involve the calibration of a plurality of different wavelength channels of an instrument, may involve the calibration of a single wavelength channel of the instrument, or may involve calibrating a combined output of a combination of different wavelength channels. In some embodiments, when material identification is being determined, the determination may be based on raw data from one or more channels and/or on the reading level variations from a plurality of channels. When identification is assumed or known, instrument calibration for a given material and given set of acquisition parameters may still be based on reading from a number of channels, relative readings from a number of channels, or it may be based on a single channel reading, or a sum of channel readings. In the simplest situations, calibration and measurements of unknowns occur using similar parameters (e.g. calibration substrate materials, surface textures, hole and/or mesh patterns, and the like, as well as similar excitation radiation exposure and reading parameters). In other situations, some differences may exist between calibration conditions and measurement conditions of unknowns such that some additional potential sources of difference will need to be taken into consideration and accommodations made, for example, via a priori knowledge, empirical correlations, or via probabilistic considerations, and the like. For example, if calibration samples are printed on solid substrates while substrates holding unknowns are perforated, it may be acceptable to simply modify the calibration factors by a ratio of the actual or average surfaces areas of the surfaces (e.g. by a perforation factor). As another example, if the excitation power when making calibration samples is different from that when measuring unknowns, the ratio of excitation powers may be used to adjust resulting calibration data (particularly where prior experimentation or theoretical consideration indicate that such power differences have linear effects on output data).

Other embodiments of the present invention relate to using calibrated spectroscopic analytic instruments in various application areas. In some embodiments, such instruments will be used in cleaning validation procedures (that may be used in laboratory settings or production settings (e.g. pharmaceutical, food, munitions, spacecraft, semiconductor, or nanotechnology), or even crime scenes, or public settings where security or contamination issues are a concern. In cleaning validation procedures, relevant surfaces will be evaluated for residual quantities of selected materials wherein quantitative determinations of surface concentrations of such materials will be made and used to determine adequacy of prior cleaning efforts to determine whether or not further cleaning is required either globally or in specific locations or of specific pieces of equipment.

Figure 2A:
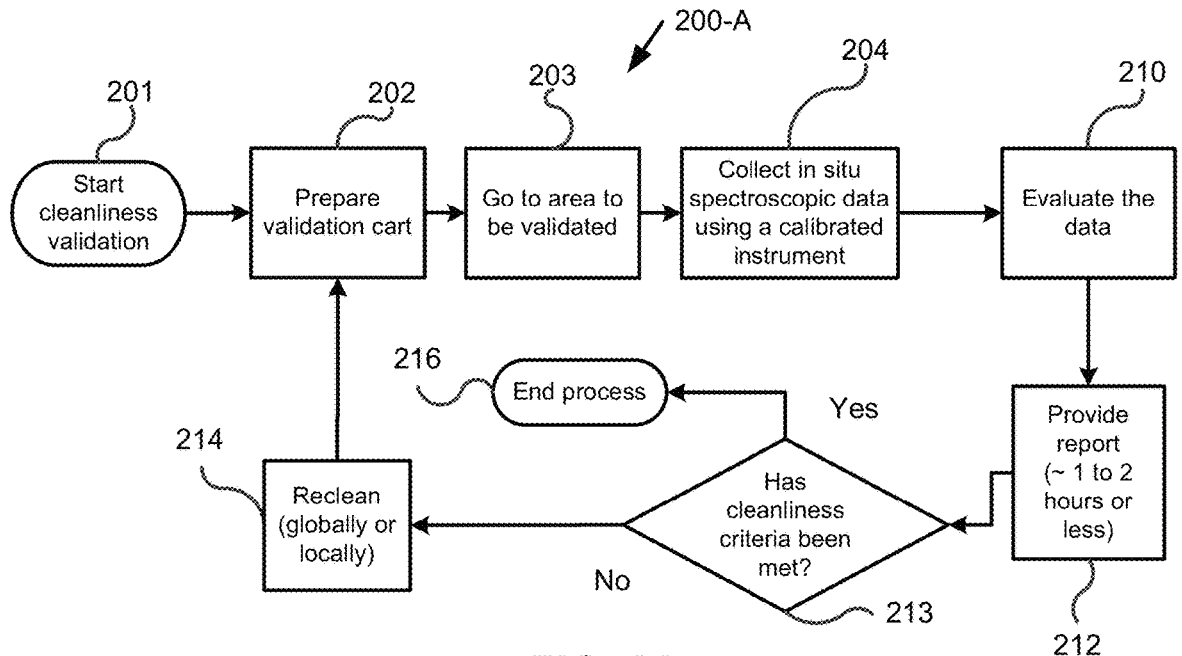
FIG. 2A provides a sample flowchart for a sample cleaning validation process according to an embodiment of the invention where any required re-cleaning occurs after the cleaning validation is completed and data is evaluated.

FIG. 2A provides a sample flowchart for a sample cleaning validation process according to an embodiment of the invention where any required re-cleaning occurs after the cleaning validation is completed and data is evaluated.

The process 200-A of FIG. 2A starts with block 201 after a cleaning has already occurred or after an assumption of cleanliness is made. From block 201 the process moves to block 202 which calls for the preparation of a validation card. Unlike block 102 of FIG. 1, the validation card of this embodiment does not include swabs and solvents, but instead includes a single or multi-channel analytical instrument and any required peripheral elements such as batteries, power supply, data cables, interface computer or the like. From block 202 the process proceeds to block 203 which moves the validation cart to the inspection area and in block 204 the collection of situ spectroscopic data occurs. The spectroscopic data is gathered from a plurality of locations which are correlated to the data gathered. The gathering of data may or may not provide direct cleanliness feedback to an operator as data is gathered and data gathering may manually be recorded or captured by the analytical instrument or a linked computer system. From block 204 the process moves forward to block 210 which calls for the evaluation of the data while block 212 calls for the providing of a cleanliness report. It is anticipated that the cleanliness report, which may be based on dozens, if not hundreds of data points, can be provided in 1 to 2 hours or less as each measurement can be obtained in as little as 1 second or less and as multiple readings from a single location can be secured within a few seconds or less. This turnaround time may be one order of magnitude, or even approaching two orders of magnitude, less than the report time using a traditional swabbing technique with all associated advantages. From block 212 the process moves forward to decision block 213 where a determination is made as to whether all cleaning requirements have been met (i.e. validated), in which case the process moves to block 216 and ends. If the requirements have not been met, the process moves forward to block 214 which calls for recleaning either globally or locally at required locations after which the process returns to block 202 for another validation attempt.

Numerous variations of the process of FIG. 2A are possible. Some variations may involve wireless transmission of data to a control computer so that the report generation can occur in parallel with data gathering. In some variations, the data collection may involve use of a single spectroscopic channel or multiple spectroscopic channels. Data gathering, or initial data gathering, may be based on an assumption that the residual material is a known material, and thus analysis may be limited to a determination of areal concentration. In some embodiments, residual material identification may occur, or multiple material identifications may occur, in addition to concentration levels for those materials having calibration data. In some embodiments, measured location may be recorded by GPS coordinates or coordinates that are temporarily or permanently affixed to the room or equipment from which electronic data may be gathered with regard to position, measurement direction, and or precise measurement location (e.g. a plurality of temporary optical image recognition signs may be used to precisely provide relative distance, position, and or angle) while in other embodiments, manual recordation of measurement regions can be made and/or non-contaminating markers can be temporarily placed on surfaces). As provided for in FIG. 2B, another variation may provide for identification of local area recleaning needs and provision of local area re-cleaning prior to data gathering for other areas such that reinspection of a local area may occur without delay.

Figure 2B:
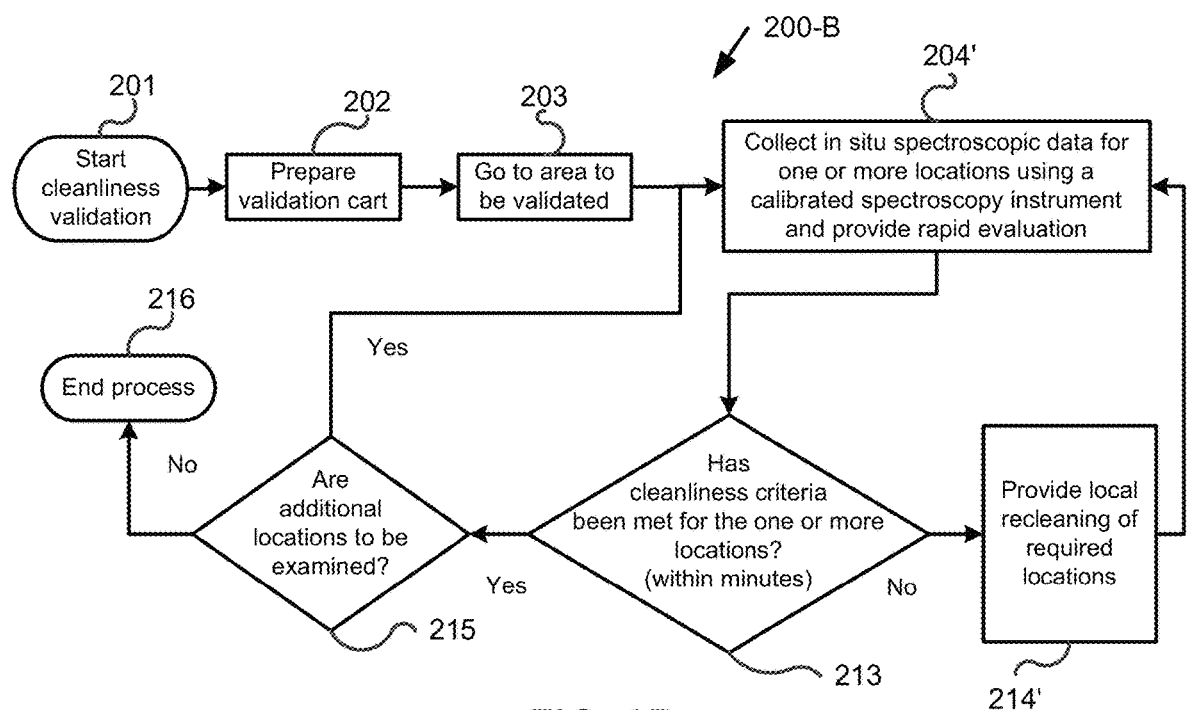
FIG. 2B provides a sample flowchart for a second sample cleaning validation process according to an embodiment of the invention where data evaluation occurs as data for each location, or data for a subset of locations (e.g. locations in a specific region), is gathered which initiates immediate re-cleaning prior to completing data gathering.

FIG. 2B provides a sample flowchart for a second sample cleaning validation process 200-B according to an embodiment of the invention where data evaluation occurs as data for each location, or data for a subset of locations (e.g. locations in a specific region), is gathered which initiates immediate re-cleaning prior to completing data gathering. Block 201-203 are similar to the same blocks in FIG. 2A. Block 204' of FIG. 2B is different from block 204 of FIG. 2A in that rapid feedback is provided to the operator without waiting for the report from sampling all locations. Because of this feedback the process moves from block 204' to decision block 213 wherein a determination of whether cleaning requirements for a location or multiple locations (e.g. within a given local area) have been met. If not, the process moves to block 214' which calls for the immediate recleaning of the location, locations, or the entire local area followed by the looping of the process back to block 204' for rereading. When the answer from block 213 provides a positive response to cleanliness criteria being met, the process moves forward to decision block 215 which asks whether additional locations are to be tested. If the answer is yes, the process loops back to block 204' for the reading of a specific location or readings of multiple locations or multiple areas. If the answer is no, the process moves forward to block 216 and ends.

As with the process of FIG. 2A, numerous alternatives to the process of FIG. 2B are possible. One such alternative may involve taking data (i.e. making of measurements) of other areas while recleaning a validation-failed area occurs. When recleaning is completed, measurement of new areas may be temporarily halted and the recleaned area may be re-inspected so that a revalidation attempt of that area can occur so that any required additional recleaning of that area, or selected portions of that area can occur, while inspection of other areas is continued, thus even further reducing the overall time of cleaning validation.

Various other cleaning validation processes are possible and will be understood by those of skill in the art upon review of the teachings herein in combination with the teachings incorporated herein by reference. Some such variations will mix and match elements of other processes and make use of various apparatus elements set forth in other embodiments discussed herein.

Next, methods for reading data from printed samples (either printed on coupons or on in situ surfaces) that may be used for providing calibration data for one or more materials of interest are addressed. The calibration samples that are read in these embodiments may be marked with their respective material, materials, concentration level, or concentrations levels so that such information may be read and manually entered into a computer system or directly into the analytical instrument. Alternatively, such information may otherwise be coded in the sample or sample substrate such that it may be read directly by one or more sensors (e.g. color sensor, camera, RF ID tag, or the like by a computer system or directly by the analytical instrument either as readings from the sample are being taken or in a separate operations. In some embodiments, samples may be encapsulated in an envelope or container (e.g. with an inert gas) to protect the samples from contamination and ensure accuracy of samples for multiple uses over an extended period. In some embodiments, coupons with samples may be marked with additional identifiers that may help validate their identity, accuracy, or viability for future use such as by inclusion of creation date information, printer information, chemical sample batch number(s), print pattern used, inclusion of temperature markers, chemical markers, irradiation exposure markers, or the like that may bring into question current accuracy of the areal concentration compared to what was initially provided.

Figure 3A:
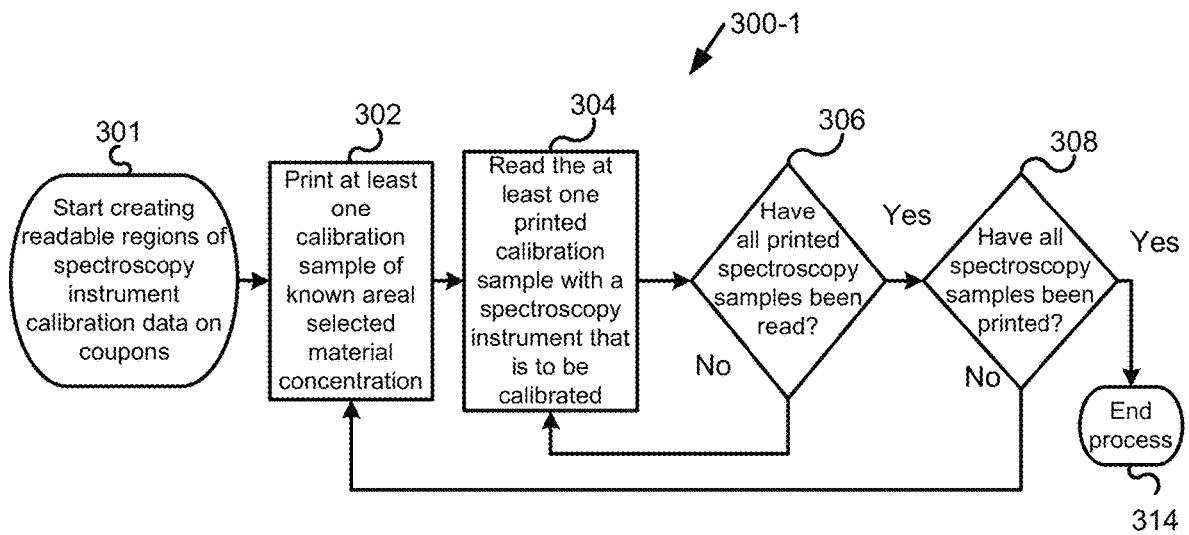
FIG. 3A provides a sample flowchart of a process for printing calibration coupons of known material and areal concentration that may be used for calibrating a spectroscopy instrument and/or for verifying calibration of a spectroscopy instrument that was previously calibrated (using the calibration coupons or using some other calibration method).

FIG. 3A provides a sample flowchart for a process 300-1 for creating coupons having known material and areal concentration and then reading the coupons using a specific spectroscopy analysis instrument to gather data for calibrating, verifying calibration, or recalibrating the spectroscopy instrument. The process of FIG. 3 begins with block 301 which calls for starting of the creation of readable data and then moves to block 302. Block 302 calls for printing of at least one calibration sample of known areal concentration of a known material. From block 302, the process moves to block 304 which calls for the reading of the one or more printed coupons. In some embodiments, in addition to the obtaining of output readings for one or more channels of the instrument for a given coupon, actual concentration data for the coupon may be directly read by the instrument, read by an associated computer system, or may be manually input into the instrument or the computer system by a user so that correlations between signal strength and actual concentration may be made. In some embodiments, where a coupon printer also holds and operates the analytic instrument (for calibration purposes), it may be unnecessary to mark individual coupons with actual concentration data as that information may be input directly from the printer into the analytic instrument or alternatively only actual calibration curve data (linear curve fit data, or the like) may be provided to the instrument. From block 304 the process moves to decision block 306 where a determination is made as to whether additional coupons have been printed that need to be read. If yes, the process loops back to block 304. If no, the process moves forward to decision block 308 where a determination is made as to whether additional samples need to be printed. If yes, the process moves back to block 302 and works forward again through blocks 304 and 306 as needed. If no, the process moves to block 314 and ends.

Numerous variations to the process of FIG. 3A, in addition to those noted in the above paragraph, are possible and include, for example, printing the readable regions on in situ substrate surfaces instead of on coupon surfaces. For example, in other embodiments all coupons might be printed and thereafter one or more spectroscopic instruments may read the coupons using a desired set of exposure and reading parameters to gather useful calibration data for each spectroscopic instrument and in particular for each spectroscopic instrument as it is intended to be used.

Figure 3B:
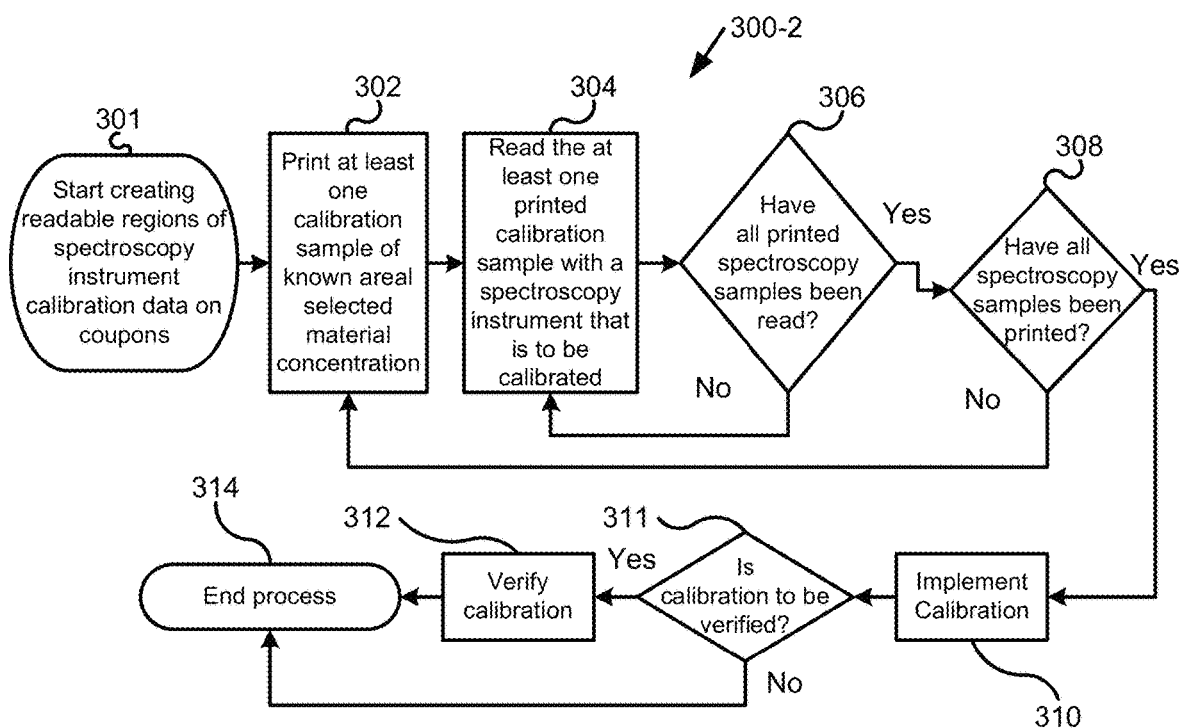
FIG. 3B provides a sample flowchart of a sample process for printing calibration coupons (similar to that of FIG. 3A) and then using those coupons to calibrate a spectroscopic instrument and then, if desired, verifying the calibration that has been performed.

FIG. 3B provides a sample flowchart for a sample process for printing calibration coupons (like that of FIG. 3A) and then using those coupons to calibrate a spectroscopic instrument and then, if desired, verifying the calibration that has been performed. The process 300-2 of FIG. 3B starts with blocks 301, 302, 304, 306 and 308 just as did the process of FIG. 3A. Instead of the process moving from 308 to 314 as if did in FIG. 3A the process moves from block 308 to block 310 which calls for implementing the calibration in the spectroscopic instrument. Thereafter the process moves to decision block 311 which calls for a decision as to whether the calibration should be verified. If no verification is to occur the process jumps ahead to block 314 and ends. If validation is to occur the process moves to step 312 where the calibration is verified (e.g. by reading samples of known material and concentration and determining if the calibrated instrument produces the correct values within an acceptable tolerance) after which the process ends at block 314.

As with the other embodiments, numerous variations of the process of FIG. 3B are possible and include, for example, using a single channel of the instrument during calibration and during verification of the calibration, using multiple channels during each, using a sum or other combination of multiple channels during each. In some embodiments, one or more of the original calibration samples could be used during verification while in other embodiments, one or more calibration samples that were not used during initial calibration could be used for verification purposes. Other examples include the variations noted above for FIG. 3A.

Various spectroscopic instruments may be calibrated by the methods and apparatus of some embodiments of the invention. Examples of some such instruments can be found in a number of U.S. patent applications filed by the present Applicant, including, for example those found in: (1) application Ser. No. 09/250,820, filed on Feb. 17, 1999, now U.S. Pat. No. 6,287,869; (2) application Ser. No. 11/245,486, filed on Oct. 5, 2005, now U.S. Pat. No. 7,525,653; (3) application Ser. No. 12/545,772, filed on Aug. 21, 2009, now U.S. Pat. No. 8,395,770; (4) application Ser. No. 12/628,205, filed on Nov. 30, 2009, now U.S. Pat. No. 8,759,791; (5) application Ser. No. 15/909,260, filed on Mar. 1, 2018, now pending, which is a continuation of and has the same specification as application Ser. No. 15/263,063, now U.S. Pat. No. 9,909,990; and (6) application Ser. No. 15/909,176, filed on Mar. 1, 2018, now abandoned, which is a continuation of and has the same specification as application Ser. No. 15/432,865, now U.S. Pat. No. 9,915,603. Each of these applications is incorporated herein by reference as if set forth in full herein.

In some embodiments, these instruments may use a variety of different incident or excitation radiations. Such radiation may, for example, take the form of one or more of deep UV (i.e. <350 nm, e.g. <=300 nm, <=280 nm, <=250 nm), UV (i.e. <=400 nm), visible (~400-700 nm), near infrared, and far infrared radiation and where emission radiation may take the form of Raman radiation, photoluminescence radiation (i.e. native fluorescence and/or phosphorescence), absorbed or unabsorbed radiation (e.g. via infra spectroscopy such as FTIR or FTNIR spectroscopy).

Figure 4A:
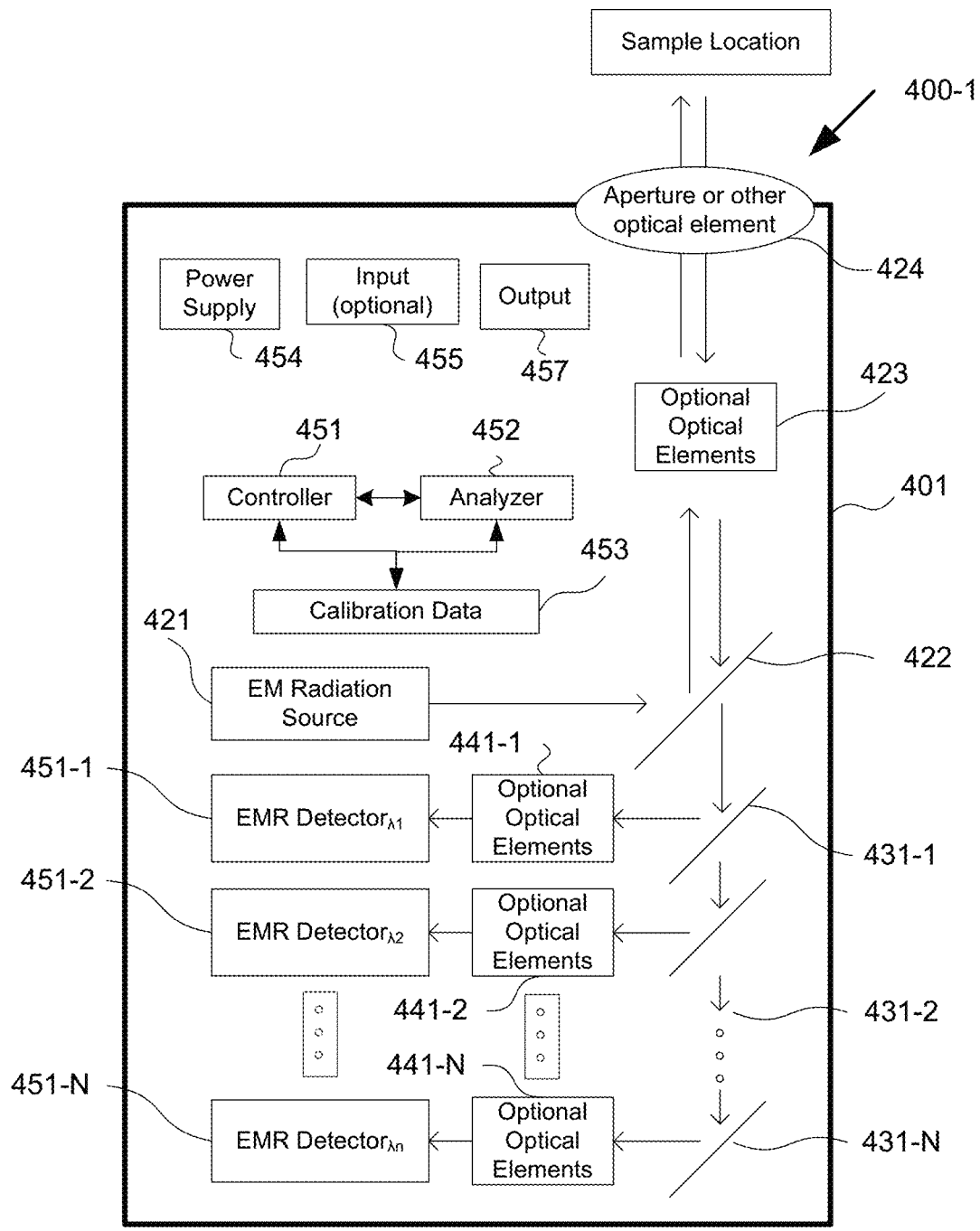
FIG. 4A provides a schematic representation of a spectroscopic instrument that may be calibrated according to some embodiments of the invention.

FIG. 4A provides a schematic representation of a spectroscopic instrument that may be calibrated according to some embodiments of the invention. In some embodiments, the device may include optical elements that provide the device with an elongated sampling appendage so that a sampling orifice, window, or lens may reach into corners or other confined spaces as well as providing access to large flat areas while maintaining a relative constant placement relative to a surface that is being examined. In some variations the device may include a pistol-like handle and one or more trigger-like interface elements, other input elements, a conveniently located display screen or other output device.

The device 400-1 includes a housing 401 that can hold a variety of optical elements and electronic elements such as: (1) a power supply 454; (2) an input device 455, such as a trigger, a key pad, a touch screen, switches, capacitive or inductive elements, wireless connections or wired connections to a separate device with manual or programmed input capability, or the like; (3) an output device 457, such as a visual screen, an auditory speaker or alarm, a wireless connection or wired connection to a separate device with output functionality, a vibrator or other tactile element, (4) a controller 451 such as an ASIC, a microprocessor including memory elements and hard coded or software implemented fixed or selectable sensing, calibration, analysis, uploading, downloading and other functional routines; (5) a source of excitation radiation 421 such as a hollow cathode metal ion laser (such as those set forth in U.S. Pat. No. 6,693,944 which is incorporated herein by reference), an LED, or an LET, or a semiconductor laser or the like (such as those set forth in U.S. Pat. No. 7,590,161 which is incorporated herein by reference); (6) an analyzer 452 which may be part of the controller or a separate component that performs or aids in determining what substances have or have not been detected and may be used to implement chemometric algorithms to provide a wide range of detection capability or focused detection for specific applications; (7) one or more optical elements 422 for directing excitation radiation onto the sample location and for passing emission radiation, which may include, for example, filters, splitters and the like (in some variations of this embodiment these elements are optional); (8) one or more optional optical elements 423 for shaping the excitation radiation prior to reaching the sample location or for providing a fixed size aperture for sealed window 424 for the housing, (9) one or more optical elements 431-1, 431-2, . . . , and 431-N (such as, for example dichroic filters, diffraction gratings, prisms, or the like) for receiving emission radiation and for directing it along different optical paths for detection by different detector elements; (10) one or more optional optical elements 441-1, 441-2, . . . , and 441-N for filtering and/or shaping emission radiation (e.g. bandpass filters, focusing lenses, and the like) that is being directed along each optical path for each separate spectral detection band or channel; (11) one or more detectors 451-1, 451-2, . . . , and 451-N (e.g. photodiodes, photomultiplier tubes (PMT), CCD, combinations of such detectors, and arrays of such detectors) for detecting the quantity of emission radiation present within each of the separate spectral detection bands; and (12) optional calibration data that can be used to convert raw data associated with a given material to a traceable calibrated value of amount of material per unit area (e.g. micrograms or nanograms per centimeter squared). Various additional elements may be included in a variety of alternative embodiments some of which have been discussed herein above while others will be discussed herein after, while still others will be apparent to those of skill in the art upon review of the teachings herein. In some embodiments, the number of detectors and associated filters and lens may be less than three (e.g. 1 or 2) while in other embodiments they may number slightly or significantly more than three (e.g. 10 or more). In some alternative embodiments, one or more secondary sources of excitation radiation may be included in device. In some alternative devices the device size may be larger or smaller than that of the most preferred embodiments, may be heavier or lighter than that of the most preferred embodiments, or may use power at a lower rate or higher rate than that of the most preferred embodiments. For example, in some embodiments, the device may have a volume that is up to ½ liters, 1 liter, or even 2 liters or more, it may have a weight up to one pound, up to two pounds, up to five pounds, or even more than ten pounds. In some embodiments, the instrument may take the shape of a badge sensor that is cell-phone sized with a 300 g weight and 10 hour battery lifetime. In some embodiments the device may use, for example, a 280 nm LED for fluorescence excitation though in other embodiments other sources may be used. Sources having shorter wavelengths will be preferred in some embodiments while longer radiation sources may be preferred in other embodiments.

FIGS. 4B-1 to 4B-3 provide several isometric views of a spectroscopic instrument that may be used as part of, or in conjunction with, some embodiments of the invention. The device of FIGS. 4B-1 to 4B-3 is known as a TraC Detector (short for Trace Chemical Detector) by Photon Systems. In some embodiments, the TraC detector is capable of trace surface or liquid contamination detection with the detector being able to detect, identify, quantify, and record data in near-real-time. Trace amounts of chemicals on the surfaces or in liquids in manufacturing machines or manufactured products can be detected. Various applications for the device and especially for a calibrated device are possible and include processes such as cleaning validation, product quality testing and control, on-line process monitoring, environmental science, forensics-crime scene investigation with industrial applications including food manufacturing, pharmaceutical manufacturing, chemical manufacturing, semiconductor/thin film manufacturing. In some usages microbial or chemical consistency in the food or beverage manufacturing industries can be monitored. In some embodiments, detectors may be made for general usage while in other embodiments, detectors may be focused and optimized for usage under vary specific and controlled conditions. In some implementations an instrument that like of FIGS. 4B-1 to 4B-3 may be made to operate at a working distance of 0 to 5 cm and more preferably from 0.5-2 cm; to operate with a sampling area or measurement area of 0.1-0.5 $cm^2$ and more preferably with an area of 0.2 to 0.3 $cm^2$; to provide a sensitivity better than 1 $ug/cm^2$; a detection time of <1 sec, a sampling rate of >10 samples/second; a housing size of <4" by <3.5" by <8" and a weight of <2 pounds.

In some implementations, the device of FIGS. 4B-1 to 4B-3 may include the components and functionality discussed with regard to FIG. 4A while in other implementations other components and functionality may be included with some of the electronic functionality removed to a separate device to which communication occurs via a wired connection or via a wireless connection. In some embodiments, internal batteries may be charged by wired connection or via wireless charging. The device 400-2 of 4B-1 to 4B-3 includes: (1) a housing 401; (2) an extended sampling appendage 402 with a cone-like tip 404 providing an input/output aperture 405 (e.g. of between 1-20 mm, preferably between e.g. 1-10 mm, or even between 2-8 mm, or even 4-6 mm); (3) a built in test sample 408 that can be placed over tip 404 and aligned with guide 407 for functionality testing; (4) a display screen 421, (5) a wired output, input, and charging port 426, (6) a slotted attachment member 415 for temporary mounting of the instrument to a calibration coupon printer or other controlled device for reading calibration coupons, (7) a trigger 411 for powering the instrument and for taking readings according to predefined settings that have been programmed into the device, and (8) a handle 451 for holding the device and for allowing easy operation of the trigger.

Numerous additional variations to the devices of FIGS. 4A and 4B-1 to 4B-3 are possible and will be apparent to those of skill in the art upon review of the present disclosure. Some variations include providing different programmed functionalities to the device, ability to vary operational parameters, and ability to perform different types of analysis and verification routines based in part on input data that is read from coupons, measurements from surfaces being tested, or acceptable error tolerance in different circumstances.

FIG. 4C provides a plot of response vs wavelength for two sample APIs that might be produced by a spectroscopic instrument of the type of FIG. 4A. The chart shows shorter wavelength excitation radiation and the associated emission responses generated by two APIs of certain concentrations and the corresponding fluorescence output generated by a multi-channel instrument similar to those illustrated in the FIGS. 4A and 4B-1 to 4B-3 analytic instruments.

Figure 5A:
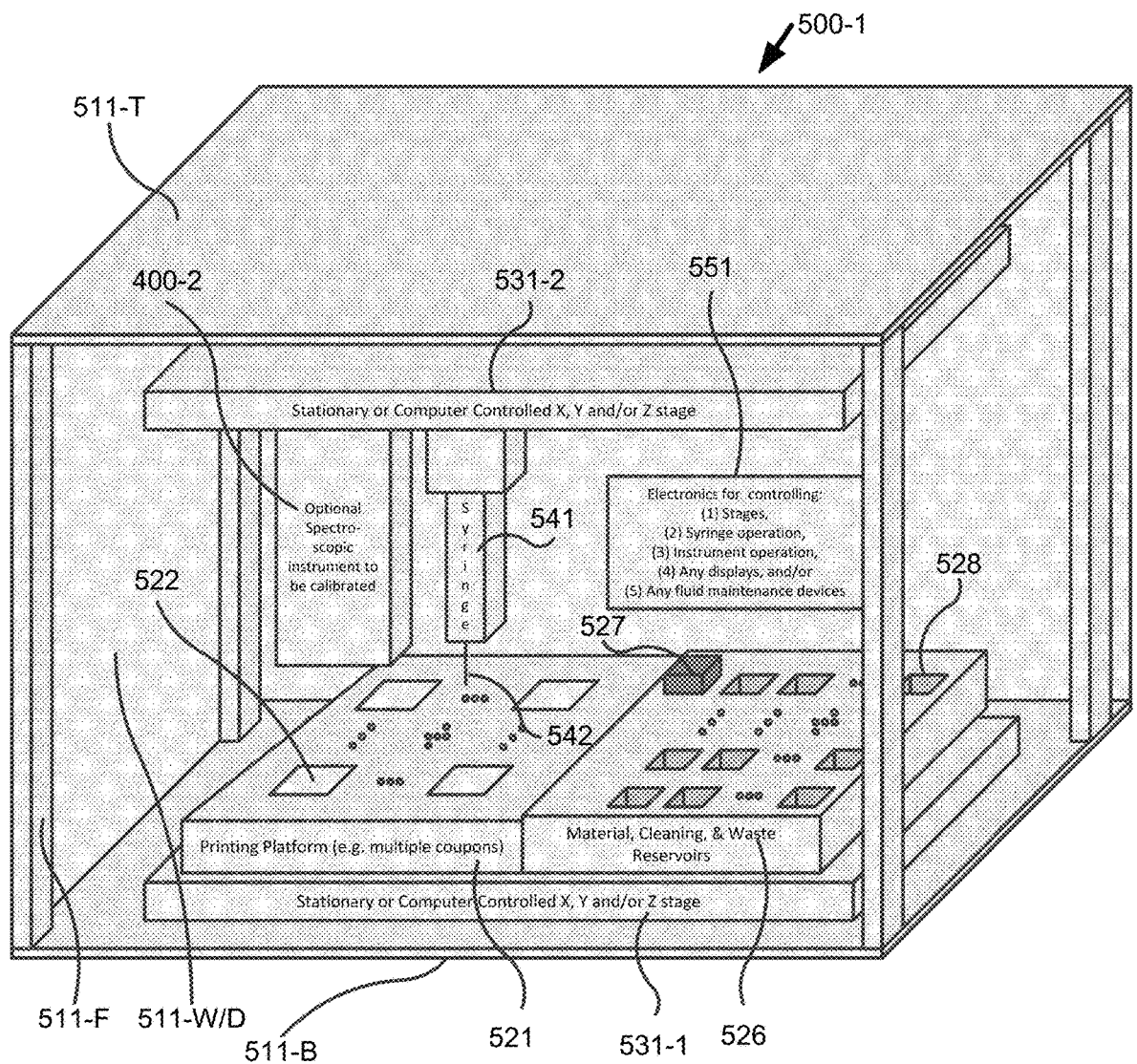
FIG. 5A provides an isometric view of major components of a sample chemical printing apparatus of an embodiment of the present invention that includes a printing area with an array of printing coupons, a printhead including a computer controlled syringe, at least one stage providing relative XYZ movement of the printhead and coupons, an optional spectroscopic instrument that may be calibrated during or after the printing of the coupons, a cleaning brush or wiping member, and a number of solution reservoirs that may hold different volumetric concentrations of different materials, cleaning solutions, waste products, or the like, that may be accessed by the syringe for cleaning, rinsing solution disposal, and printing purposes.

FIG. 5A provides an isometric view of major components of a sample chemical printing apparatus 500-1 of an embodiment of the present invention that includes a printing area with an array of printing coupons 522, a printhead including a computer controlled syringe 541 with a dispensing/filling needle 542, at least one stage 531-2 and 531-1 providing relative XYZ movement of the printhead and coupons (e.g. stage 531-2 may provide Z (or vertical) movement of the syringe and side to side movement in X while stage 531-1 provides for back and forth movement in Y), an optional spectroscopic instrument 400-2 may be attached to stage 531-2 and may undergo calibration during or after the printing of the coupons by the printer controlling operation of the instrument to read coupons after each is printed and dried, a cleaning brush or wiping member 527 may be included to allow needle wiping as necessary, while a number of solution reservoirs, such as 528, may be provided to hold different volumetric concentrations of different materials, cleaning solutions, waste products, or the like, that may be accessed by the syringe during refilling operations, during syringe emptying operations, during rinsing or cleaning prior to refiling operations, during preliminary refill operations for enhanced cleaning and concentration control, and during final refill operations before actual dispensing of droplets during the creation of calibration coupons. The printer may include frame elements 511-F, a base element, 511-B, a top element 511-T, and see through panels, windows, or doors 511W/D and one or more electronic control and interface boards 551.

Figure 5B:
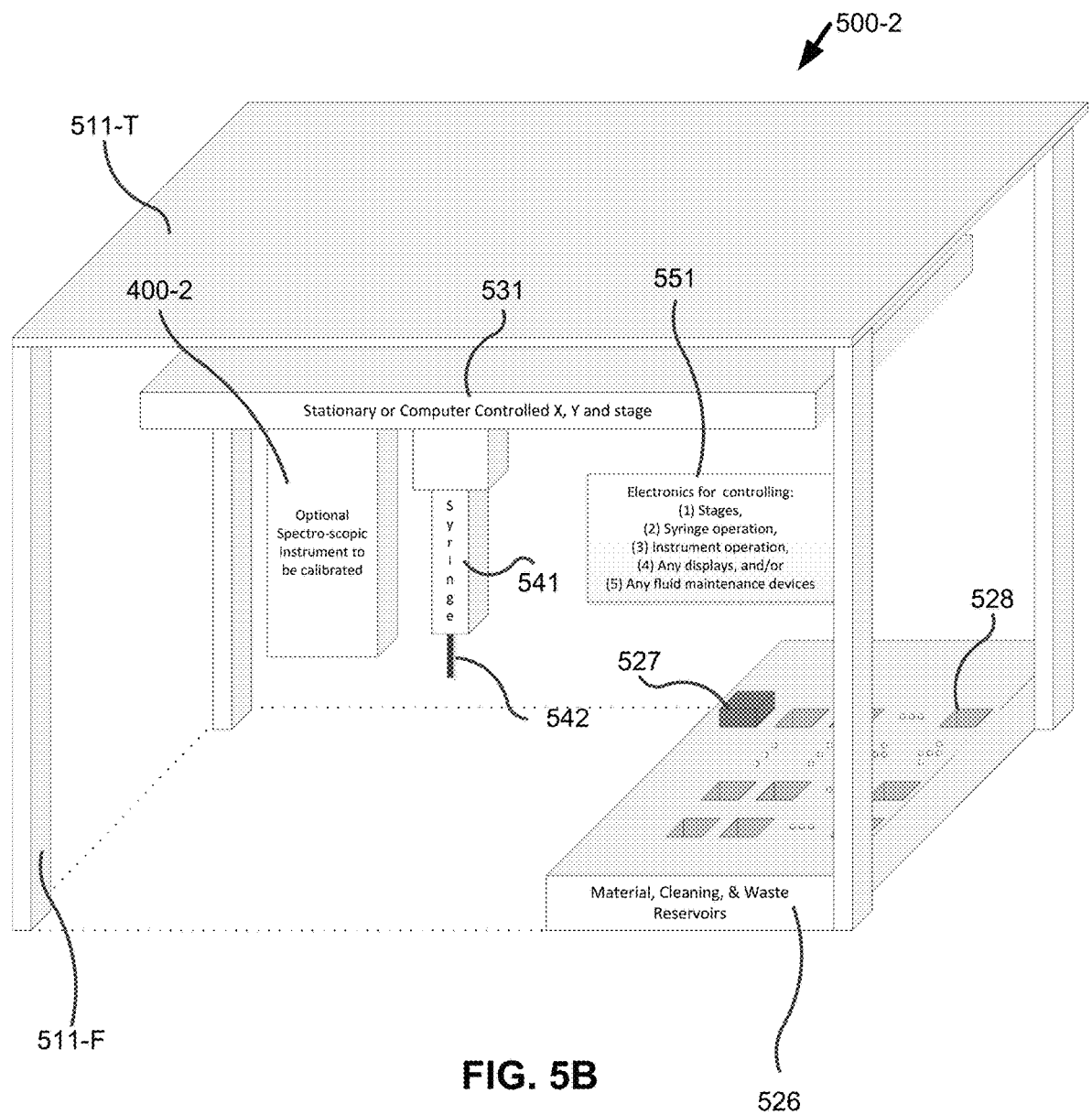
FIG. 5B provides an isometric view of major components of a sample chemical printing apparatus for printing onto an in situ surface according to an embodiment of the present invention wherein the printer includes a printhead including a computer controlled syringe, at least one stage providing XYZ movement of the printhead, an optional spectroscopic instrument that may be calibrated during or after the printing of the coupons, a cleaning brush or wiping member, and a number of solution reservoirs that may hold different volumetric concentrations of different materials, cleaning solutions, waste products, or the like, that may be accessed by the syringe for cleaning, rinsing disposal, and printing purposes.

FIG. 5B provides an isometric view of major components of a sample chemical printing apparatus 500-2 for printing onto an in situ surface according to an embodiment of the present invention wherein the printer includes a printhead including a computer controlled syringe 541 and a dispensing/filling needle 542, a stage providing XYZ movement of the syringe 541 and possibly only XY movement of a temporarily attached spectroscopic instrument 400-2 that may be calibrated during or after the printing onto the in situ surface, a cleaning brush or wiping member 527, and a number of solution reservoirs, 528 that may hold different volumetric concentrations of different materials, cleaning solutions, waste products, or the like, that may be accessed by the syringe for material disposal when no further use of the material is needed, cleaning in preparation for filling with new material, rinsing as part of the cleaning process, preliminary filing as part of concentration control process when a material is being replaced by a material of different identity or concentration, and for providing final filling material for printing purposes.

Numerous alternatives to the printers of FIGS. 5A and 5B are possible with the features of primary importance being (1) dispensing of droplets from a computer controlled syringe capable of applying small droplets of fixed and known size and of known material concentration, (2) dispensing at a droplet rate and X, Y, and Z movement rate that is fast enough and with high enough positioning accuracy and repeatability to form coupons in a reasonable time with high uniformity so that areal concentration across a coupon is consistent and known accurately, (3) sufficient movement control in Z to allow known and safe contact of needle tip with a substrate and/or sufficient movement control in Z to avoid needle contact with the substrate while allowing the needle to approach within one unreleased droplet height of the substrate so that accurate formation of droplets and controlled release can occur (e.g. when the droplet contacts the substrate or when the needle lifts from a droplet to substrate contact position to a needle to substrate separation distance greater than the height of an unreleased droplet from the substrate).

In some embodiments the following printing parameters may be targeted: (1) Droplet size: 1 to 50 nanoliters; (2) Print Area: Capable of producing a desired number of coupons (e.g. 1-25) of desired size (e.g. squares of 1.5 to 2.5 inches on edge), (3) desired areal concentrations: <1 nanogram/cm$^2$ to >10 milligrams·cm$^2$, (4) reasonable droplet dispensing rates: >200 droplets per minute, and (5) reasonable XY and Z movement rates allows timely coupon printing. In other embodiments different parameters may be acceptable. In some embodiments accurate and controlled setting of needle tip position in Z may occur by contacting the needle to the substrate which in turn may lift the syringe slightly from its seat on the Z-stage allowing a contact switch to release. Once contact is made for a given $X_n Y_n$ position, motion control systems (e.g. stepper motors and the like) or sensor systems may be used to provide knowledge of relative motion and provide for programmed control of any desired amount of motion. In other embodiments other methods may be used to provide contact detection between the substrate and the tip of the needle, such as application of a voltage or current source between the needle tip and the substrate such that detection of current or other electrical signal can indicate when contact occurs. In other embodiments, a spring-loaded physical contact sensor could be used where the tip of the contact sensor is located a desired distance below the tip of the needle. In still other embodiments, if it is possible to forego knowledge of absolute needle position relative to the substrate it may be possible to use circuit closing detection to detect when a droplet bridges the gap between the needle tip and the substrate. In still other embodiments, non-contact detection may involve use of, for example, a high resolution ultrasonic or inductive sensor. Similar reliable X and Y motion controlled may be implemented by the ability to provide for desired relative motion (e.g. via stepper motors or linear encoders or the like) in combination with a fixed detection position (e.g. via contact sensing of a 0,0 location).

In some embodiments, reasonably uniform distributions of material may be obtained by depositing droplets with a desired overlap. In some such embodiments, it may be possible to deposit such droplets one neighboring droplet after another to obtain acceptable results; however, as a general practice, when dispensing droplets where a uniform distribution is desired, it is optimal to dispense the droplets in a pattern that provides for a reasonable dispensing rate while still ensuring that newly dispensed droplets do not overlay previously dispensed droplets that are still wet. This may be done by dispensing droplets in patterns that ensure that the delay in dispensing overlapping droplets is sufficient large that previously dispensed droplets have cured or dried prior to receiving deposition of a new droplet which helps minimize surface tension effects, or other effects, from dragging droplets out of their dispensed positions.

Figure 6A:
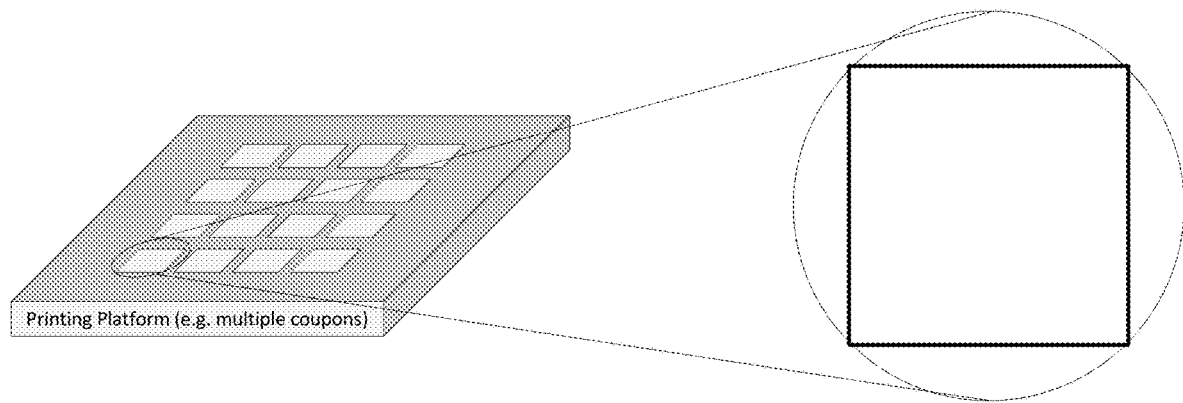
FIG. 6A provides an isometric view of a printing platform with 16 coupons with one coupon shown to the right in the form of an expanded top view of a coupon.

FIG. 6A provides an isometric view of a printing platform with 16 coupons with one coupon shown to the right in the form of an expanded top view of a coupon.

Figure 6B:
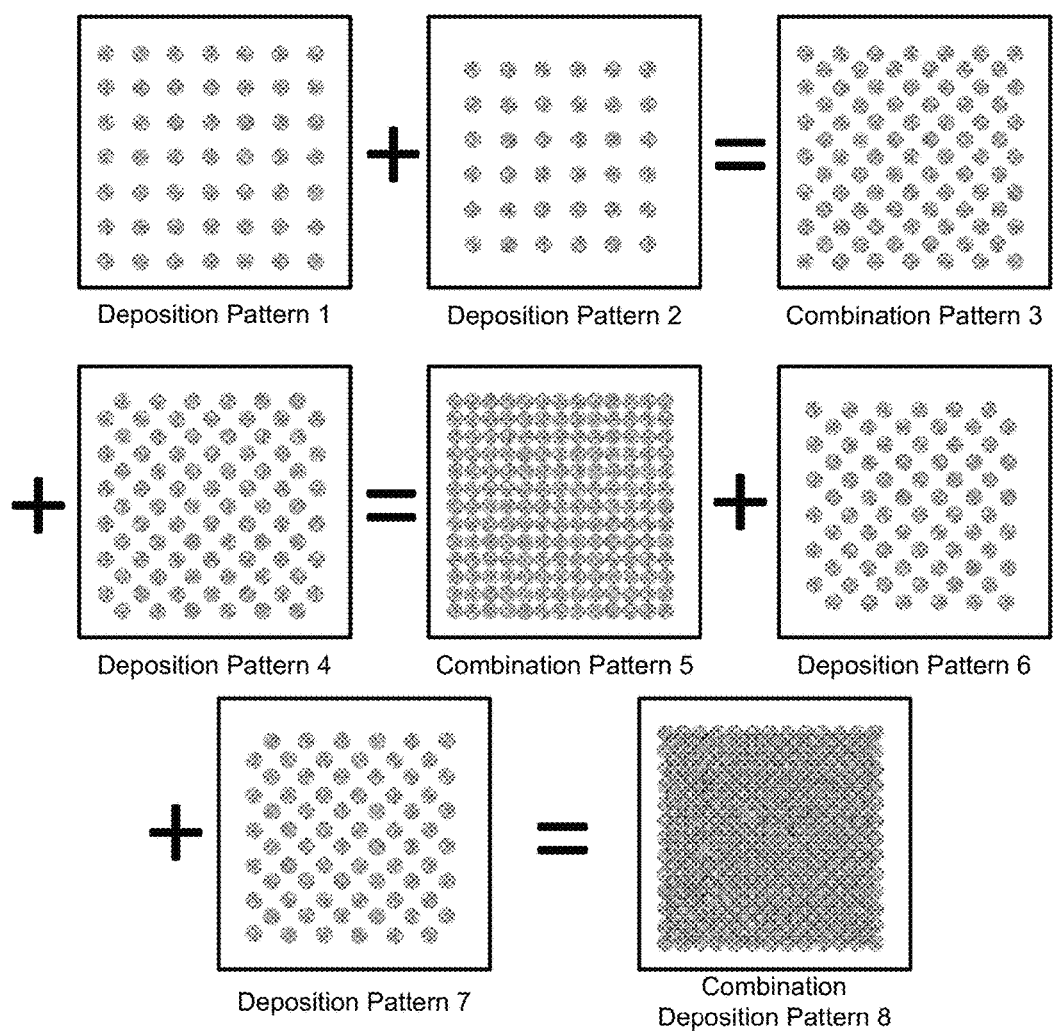
FIG. 6B provides eight top views of a coupon that has received different print patterns of chemical droplets illustrating a range of different droplet spacings and different levels of spaced and overlapped droplets that may be achieved by single or multiple deposition processes.

FIG. 6B provides eight top views of a coupon that has received different print patterns of chemical droplets illustrating a range of different droplet spacings and different levels of spaced and overlapped droplets that may be achieved from multiple interlaced deposition processes that yield adequate time between the dispensing of overlapping droplets so as to ensure that that new droplets do not overlay droplets that are still in a liquid state.

Deposition Pattern 1 (DP1) provides an example pattern of dispensed droplets having a first spacing from one another. In this first pattern the droplets are dispensed with a sufficient spacing that neighboring droplets do not overlap or contact each other initially upon dispensing. Without slowing the dispensing, all droplets may be dispensed in any order without concern that a newly dispensed droplets will contact a previously dispensed droplet while the previously dispensed droplet was still wet.

Deposition pattern 2 (DP2) provides an example pattern of dispensed droplets having the same spacing of those of DP1 but with an offset in X and Y positioning such that the droplets of DP2 would interlace with the droplets of DP1 such that each droplet of DP2 would center itself between four droplets of DP1 if they were overlaid.

Combination Pattern 3 (CP3) illustrates the pattern that would occur if DP1 were followed by DP2. Due to the spacing of droplets of DP1 and DP2, the pattern of CP3 indicates that the CP3 droplets do not overlap each other and as such, instead of dispensing two overlaid patterns to achieve CP3, CP3 could have been directly formed without worry of any droplets coming into premature contact with other droplets during dispensing. The other feature to note about the pattern of CP3 is that the droplets are getting close enough together that the distribution of material is significantly more uniform than the distributions of DP1 or DP2.

Deposition Pattern 4 (DP4) has a similar droplet-to-droplet spacing as does CP3 but careful observation also indicates that the droplets in DP4 are spaced to correspond to the vacancies in the pattern of CP3. As such, if the pattern of DP4 was deposited over CP3 the Combination Pattern 5 (CP5) would result in much more uniform spacing of deposited material than in any of proceeding droplet patterns. However, the pattern of CP5 could not readily be formed by use of a simple dispensing pattern as neighboring droplets in this pattern do overlap, or at least potentially contact one another, and thus could be negatively impacted if subsequently dispensed droplets contact previously dispensed droplets that are still in a liquid state which could cause the subsequent droplets to move from their desired positions. As such, in forming a pattern like CP5, care in the implementing the dispensing order must be observed to ensure droplets remain where they are placed where the care can be achieved by dispensing a pattern like CP3 followed by DP4 with possibly a small delay in between completing the deposition of the CP3 pattern and initiating deposition of the DP4 pattern if necessary to ensure that those portions of CP3 that will receive the initial deposits of DP4 have dried.

Deposition Pattern 6 (DP6) and Deposition Pattern 7 (DP7) are complementary patterns but have droplets too close to deposit at the same time in a simple order. In one example, these patterns could be dispensed one after the other to interlace them with a far reduced chance of any droplets landing on other droplets that are still in a partially liquid state. Further comparison of DP6, DP7 and CP5, show that DP6 and DP7 taken together are complementary to CP5 as their droplets are centered over the holes of CP5. As such, deposition of a pattern providing the configuration of CP5, followed by deposition of DP6 and then DP7 would produce the pattern of CP8 with little risk of dispensing droplets onto previously dispensed droplets that are still in a partially liquid state yielding a resulting pattern having even higher uniformity than any of the previous patterns.

Dispensing patterns may occur in a large variety of orders with the primary caveat being to avoid dispensed droplets contacting other droplets that are still in a liquid state. Additionally, as will be discussed later, the tighter a pattern of dispensed droplets are, the more uniform or homogenous the dispensed material will appear to a measurement or detection spot of a given diameter.

Figure 7A:
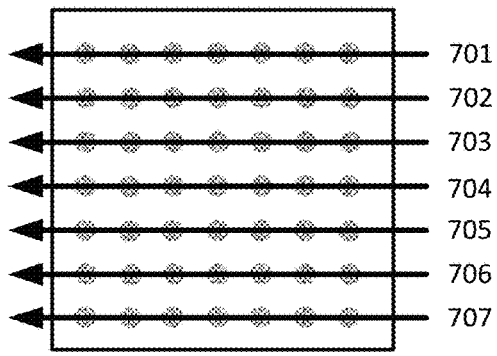
FIGS. 7A-7B illustrate a common pair of droplet patterns achieved using different dispensing orders.
Figure 7B:
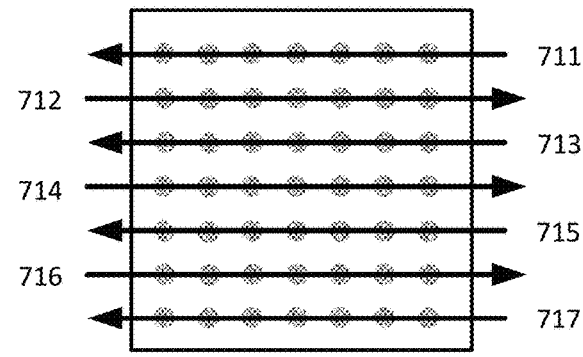

FIGS. 7A-7D illustrate how different dispensing patterns may result in the same nominal patterns of deposited materials. First, FIG. 7A provides a droplet pattern of 7 horizontal rows with each including seven droplets. In dispensing the pattern of FIG. 7A, line 701 is first formed from right to left, then 702 to 707 are formed also from right to left. This formation pattern is reasonably efficient, but the syringe must make a relatively large XY movement at the end of each row to position itself for depositing a subsequent row. In some cases, such movement may be useful in providing an appropriate delay prior to dispensing neighboring, and potentially overlapping, droplets. In the case of FIG. 7A since the droplets do not overlap, such a delay is not required. FIG. 7B depicts the deposition of a pattern which is the same as that of FIG. 7A but as indicated by the printing lines, a first line 711 is printed from right to left while a next, neighboring line 712 is printed from left to right. This pattern is repeated until the droplet array is fully deposited with odd numbered rows (711, 713, 715, and 716) being dispensed from right to left and even numbered rows being dispensed from left to right (712, 714, 716).

Figure 7C:
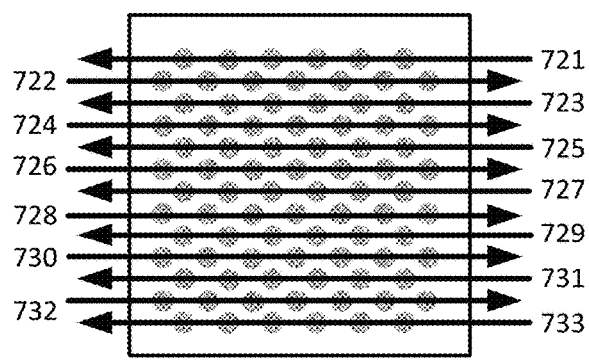
FIGS. 7C and 7D illustrate a different common pair of droplet patterns achieved using different dispensing orders.
Figure 7D:
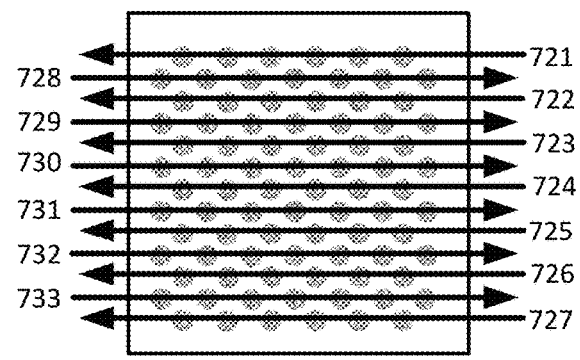
Figure 8A:
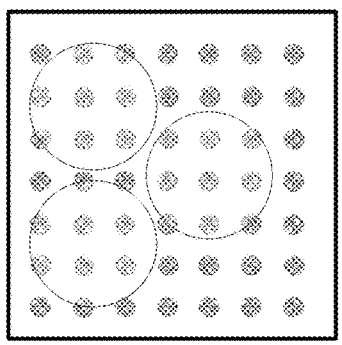
FIGS. 8A-8L provide illustrations of 4 different chemical droplet patterns (with FIGS. 8A-8C based on pattern 1 of FIG. 6B, FIGS. 8D-8F based on pattern 3 of FIG. 6B, with FIGS. 8G-8I based on pattern 5 of FIG. 6B, and with FIGS. 8J-8L based on pattern 8 of FIG. 6B), with each droplet having a given nominal diameter, in combination with a number of overlaying circles representing effective detection areas of different spectral instruments with 3 different diameters (i.e. areas that receive incident or excitation radiation and in turn provide emission radiation that can be read by the spectroscopic instrument) showing that effective droplet uniformity, or homogeneity, of concentration can exist even with patterns of discrete droplets so long as the measurement area picks up a relatively consistent number of droplets when it reads random locations on a coupon.
Figure 8B:
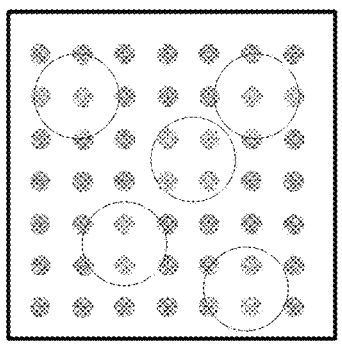
Figure 8C:
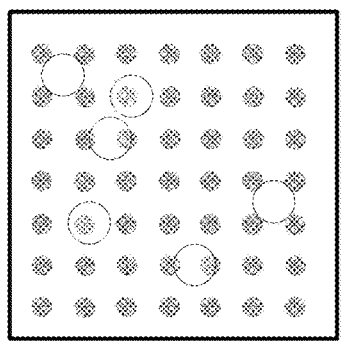
Figure 8D:
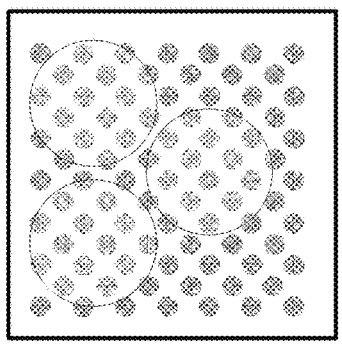
Figure 8E:
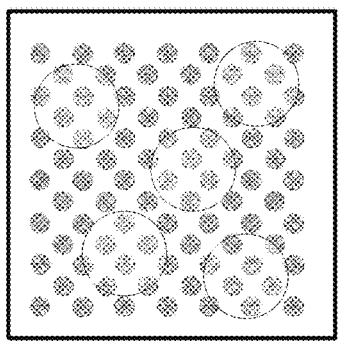
Figure 8F:
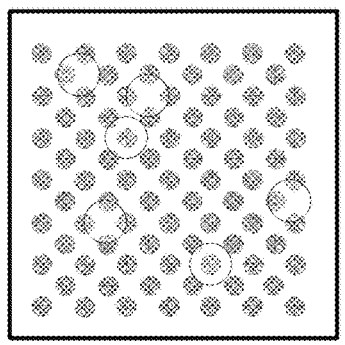
Figure 8G:
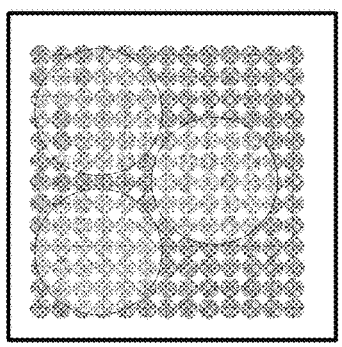
Figure 8H:
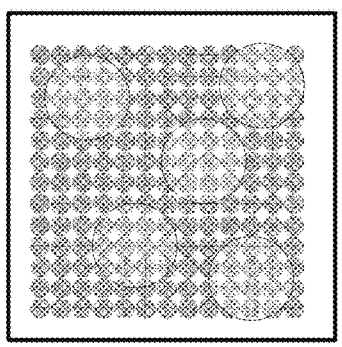
Figure 8I:
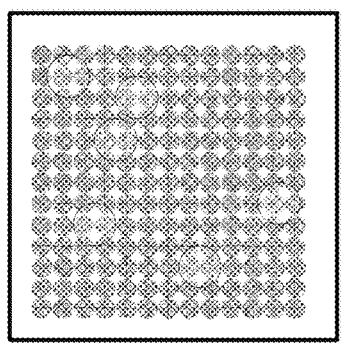
Figure 8J:
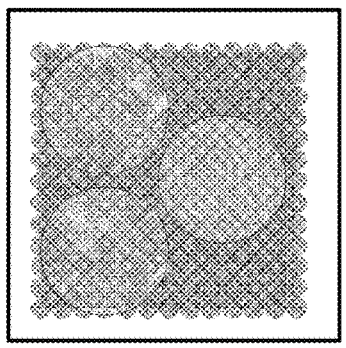
Figure 8K:
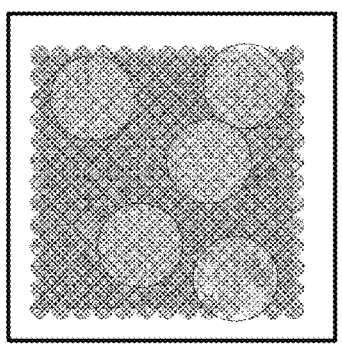
Figure 8L:
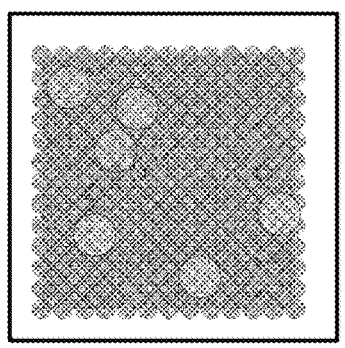

As another example, FIGS. 7C and 7D illustrate two different dispensing patterns that achieve a common result with different delays between printing neighboring droplets. In the final droplet pattern of FIGS. 7C and 7D, the droplets are more closely spaced than they were in FIGS. 7A and 7B and even though the droplets do not appear to overlap or touch each other, out of an abundance of caution it may be desired to use a dispensing pattern that provides a larger delay in dispensing neighboring droplets while still providing a reasonable overall dispensing time. In FIG. 7C the dispensing pattern for depositing each row is in a reversed order as was done in creating 7B. Odd numbered rows (721-733) are dispensed right to left while even numbered rows (722-732) are dispensed left to right which leaves only a small-time gap between dispensing the last and first, or first and last, neighboring droplets of successive rows. In FIG. 7D the dispensing order is changed such that the dispensing pattern skips every other row during a first series of right to left dispensing operations (721-727) and then fills in the missing rows with a series of left to right dispensing operations (728-733) which allows larger time gaps in dispensing neighboring droplets with the closest positioning to ensure that droplets are no longer in a liquid state when subsequent neighboring droplets are dispensed. The examples of 7A-7D are intended to be illustrative of how droplet dispensing order can be used in optimizing dispensing order for both efficient pattern creation and for minimizing occurrence of droplet migration. One of ordinary skill will, upon review of the teachings herein, recognize that other dispensing patterns may be used and that some will provide enhanced efficiency while still ensuring other requirements are met.

FIGS. 8A-8L provide illustrations of 4 different chemical droplet patterns (with FIGS. 8A-8C based on DP1 of FIG. 6B, FIGS. 8D-8F based on CP3 of FIG. 6B, with FIGS. 8G-8I based on CP5 of FIG. 6B, and with FIGS. 8J-8L based on CP8 of FIG. 6B), with each droplet having a given nominal diameter, in combination with a number of overlaying circles representing effective detection areas of different spectral instruments that might be randomly positioned when making readings from the print patterns with the first of each group of figures (A, D, G, and J) illustrating relatively large detection areas, the second of each group (B, E, H, and K) showing smaller detection areas, and the third of each group (C, F, I, and L) showing even smaller detection areas, where detection areas are those areas that receive incident or excitation radiation and which can provide emission radiation that can be read by the spectroscopic instrument). A review of FIGS. 8A, 8D, 8G, and 8J shows that as droplet dispensing locations become closer the amount of material, seen within the measurement area of instrument, for a given detection location, becomes more and more uniform and as such any given measurement is more likely to provide a similar reading to that of other measurements. When droplet spacing is more separated, the uniformity of seeing and reading similar amounts of material for a given measurement area becomes more difficult. One conclusion that can be drawn from this illustration is that the closer the droplets are spaced the more likely that droplets that are read by any single reading will represent the average concentration of the material that was dispensed. Another conclusion that might be reached is that if the droplets are not too far apart, a plurality of randomly located readings might be used, or groups of a plurality of randomly located readings might be used, along with calculations of means and standard deviations to provide statistically reasonable reading values that correspond to applied areal concentrations. Similar conclusions might be reached for FIGS. 8B, 8E, 8H, and 8K where a medium sized measurement area is used as well as FIGS. 8C, 8F, 8I, and 8L where a small diameter measurement area is used. Simple observation of geometry of these diagrams may lead one to conclude that a single measurement using any of the different measurement spot sizes applied to the tightest droplet patterns (FIGS. 8J, 8K and 8L) will yield a reading based closely on the average areal concentration of the dispensed material. However, multiple readings may be used to provide an average and standard deviation that may be useful in increasing confidence. One may also draw a similar conclusion for the patterns of FIGS. 8G and 8H but might question how reliable any single reading from pattern 8I would be. If the pattern of FIG. 8I were to be used, multiple measurements and averaging, or some other more sophisticated statistical methods, may be needed to provide the confidence in any conclusions reached. Comparing FIGS. 8D, 8E and 8F may yield a conclusion that simple averaging using a reasonable number of randomly positioned measurements may work for the pattern of FIG. 8D, but more sophisticated methods would be needed to make use of the patterns of FIGS. 8E and 8F, if the pattern of FIG. 8F could be used at all. Similar observations of 8A, 8B and 8C may lead one to conclude that the patterns are simply not useable under reasonable conditions though the pattern of FIG. 8A, and maybe even the pattern of FIG. 8B, could be useable if more readings and more extensive statistical analysis are used. A primary takeaway from this illustration is that using appropriate measurement areas and much smaller droplet pattern pitches may lead to simpler and potentially more reliable calibration procedures.

Coupon printing, or in situ surface printing, methods can take a variety of forms and be implemented, for example, in software or hardware on a control computer, be implemented in software or hardware on a print device itself or be implemented in a combination of a control computer and a printer. In different implementations, printer set up instructions may range from a very basic form where a user makes many of the printing decisions and lays out commands for printing up to a very sophisticated form where the user specifies printing goals and the printer or control computer creates and implements a printing plan to achieve the goals including generation of all detailed printing instructions.

Basic printing parameters may involve the user deciding droplet spacing based on droplet size and material concentration so that a desired areal concentration of material is achieved by printing process. The basic process may also require the user to determine a dispensing order for the droplet pattern so that droplets are not dispensed on other droplets that are still in a liquid form. Finally, once all decisions have been made by the user, appropriate parameters are created by the user and fed to the printer or control computer.

In a more sophisticated process, a user may only provide the printer or control computer with (1) solution identification and/or solution concentration, (2) a measurement size if not of a default size expected by the printer, and (3) a desired final areal concentration for each coupon to be printed. After receiving this general input, the control computer or printer can calculate various printing parameters and associated printing instructions. Such parameters might include calculation of things like droplet spacing, droplet dispensing order, material replacement operations, and the like. In still other implementations, parameter specification may involve user input that is intermediate to these two extremes or even user approval of implementation plans proposed by the control computer or printer. In some embodiments, the printer or control computer may associate the printing parameters of a coupon directly or indirectly with the coupon so that in using the coupon for calibration purposes, appropriate reading and analysis parameters may be implemented in the coupon reading process and in the process of using the spectroscopic instruments when reading unknown materials. Capture of such information may help in ensuring that parameters used in reading unknown materials or known materials of unknown concentration are appropriate to the calibration factors that will be used in converting raw data to calibrated data.

Figure 9A:
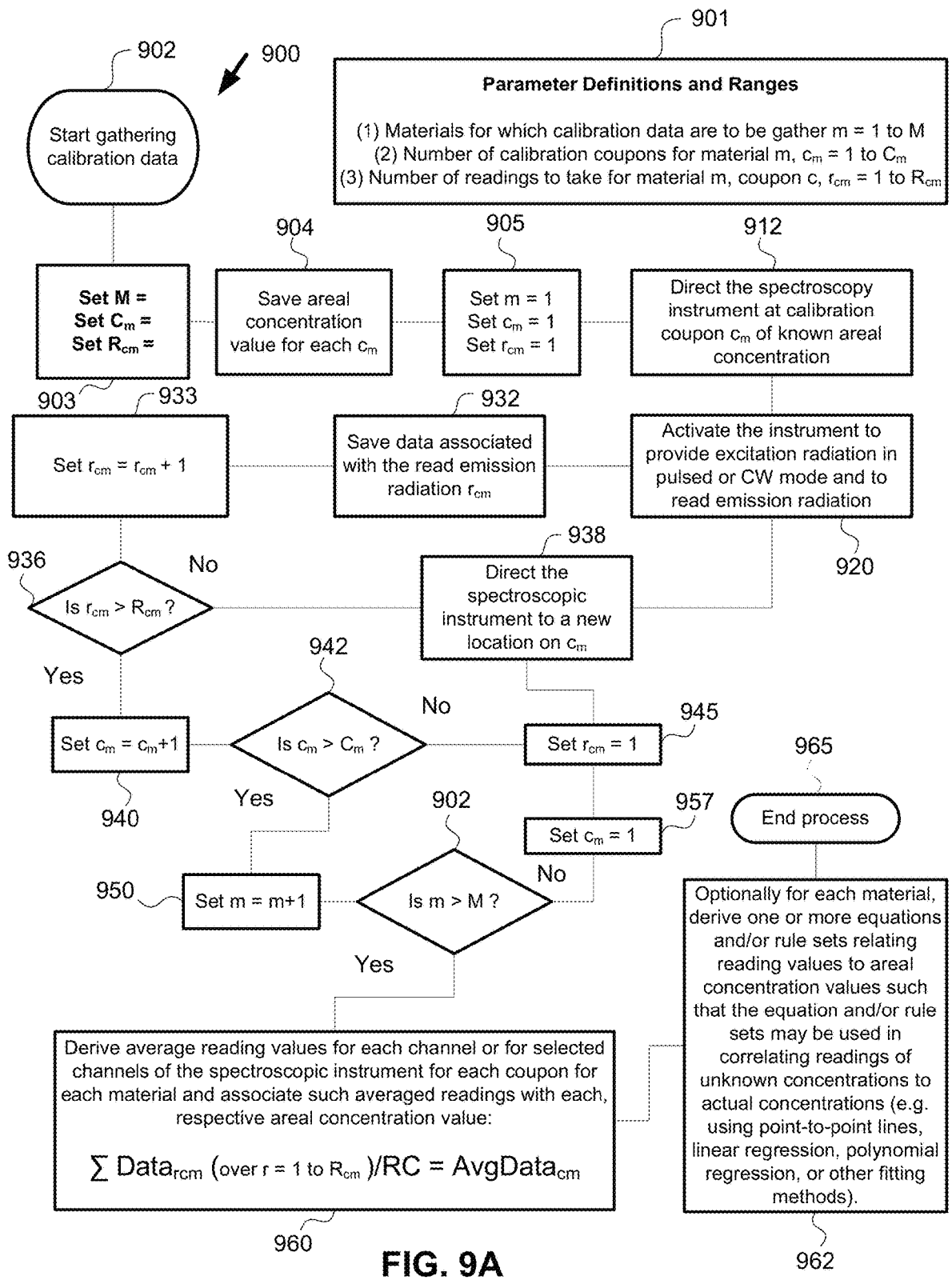
FIG. 9A provides a flowchart setting forth an example process for gathering data for a specific spectroscopy instrument from each of a plurality of coupons (using a hold, measure, move, and repeat process in combination with either pulsed or CW operation of the spectroscopic instrument's excitation radiation source or using a slow move and periodic read process) and using the data and known areal concentration of each coupon to establish calibration information for the specific spectroscopic instrument (e.g. by obtaining average data values for each concentration of each material or deriving one or more equations that fit the data or provide best fits to the data).

FIG. 9A provides a flowchart setting forth an example process for gathering data for a specific spectroscopy instrument from each of a plurality of coupons (using a hold, measure, move, and repeat process in combination with either pulsed or CW operation of the spectroscopic instrument's excitation radiation source or using a slow move and periodic read process) and using the data and known areal concentration of each coupon to establish calibration information for the specific spectroscopic instrument (e.g. by obtaining average data values for each concentration of each material or deriving one or more equations that fit the data, or provide best fits to the data).

Understanding of the process 900 of FIG. 9A requires an understanding of the parameters and definitions that form part of the process. These parameters and definitions are found in block 901. The process itself begins with the block 902 which calls for the gathering of calibration data from which the process moves to block 903 which provides for the setting or inputting of the number of materials M for which the calibration process will be performed, the number of calibration coupons that will be produced for each material $C_m$ which may be a different number for each material m, and the number of readings that will be made for each coupon $R_{cm}$ which may be different for each material m and each coupon c. Next in block 904 the process calls for saving the areal concentration that is associated with each coupon $c_m$. Next the process moves forward to block 905 where values for each of m, $c_m$, and $r_{cm}$ are set to 1. From 905 the process moves to block 912 which calls for directing the spectroscopy instrument at a calibration coupon $c_m$ of known areal concentration (e.g. at a substantially perpendicular angle at a relatively close spacing, e.g. 0.25 to 1.0 inches) while in block 920 the process calls for the activation of the instrument so as to provide exposure radiation or excitation radiation and reading of returned emission radiation. The process of block 920 may take on a variety of different forms with various examples listed in the block diagram of FIG.

9B. From block 920 the process moves to block 932 which calls for the saving of data associated with the returned emission radiation and thereafter in block 933 the incrementing of $r_cm$ by 1. From block 933 the process moves to decision block 936 where a determination is made as to whether $r_{cm}$ is greater than $R_{cm}$. If yes, the process moves forward to block 940 and if no, the process moves to block 938 which calls for directing the instrument to read a new location on cm and then to loop back to block 920 to begin the process of gathering data from another portion of the coupon. If the process moved forward to block 940, cm is increment by 1 which moves the process to decision block 942 which calls for determining whether the $c_m > C_m$. If yes, the process moves forward to block 950, and if no, the process moves to block 945 where $r_cm$ is reset to 1 in preparation for gathering data for a new coupon. From block 945 the process moves to block 938 and then to block 920 as discussed above.

When the process moves to block 950, m is incremented by 1 after which the process moves to decision block 902 where a determination is made as to whether m is greater than M. If m>M, the process moves forward to block 960 and if not, the process moves to block 957 wherein the cm is reset to 1 in preparation for reading of not only a new coupon but also a new material. From block 957 the process moves to block 945, then 938, and then 920 as discussed before.

When the process moves to block 960, an average value of each of the readings for a single instrument channel, or for multiple instrument channels, is, or are, determined. From block 960 the process moves forward to block 962 where an optional process of determining one or more calibration equations or rule sets for each material to allow readings of unknown concentration to be correlated to actual material concentrations. From 962 the process moves forward to block 965 and ends.

Various alternatives to the process of FIG. 9A are possible and include, for example: (1) with regard to block 903 the number of materials may be the only specifiable parameter as the number of calibration coupons for each material may be fixed at, for example, 4 to 6 and the number of readings per coupon could also be fixed at, for example, a number between 1 and 10 inclusive; (2) with regard to block 904 the input of the desired information may occur at a number of points in the process; (3) with regard to block 960, operations other than averaging operations may be used in associating values read from coupons with known concentration values wherein these methods may involve extracting other information and the performing of various tests (such as statistical tests) on the data to ensure reliability or at least sufficient probability of data veracity; and (4) in other processes different orders of operations may be used and different control parameters may be used.

Figure 9B:
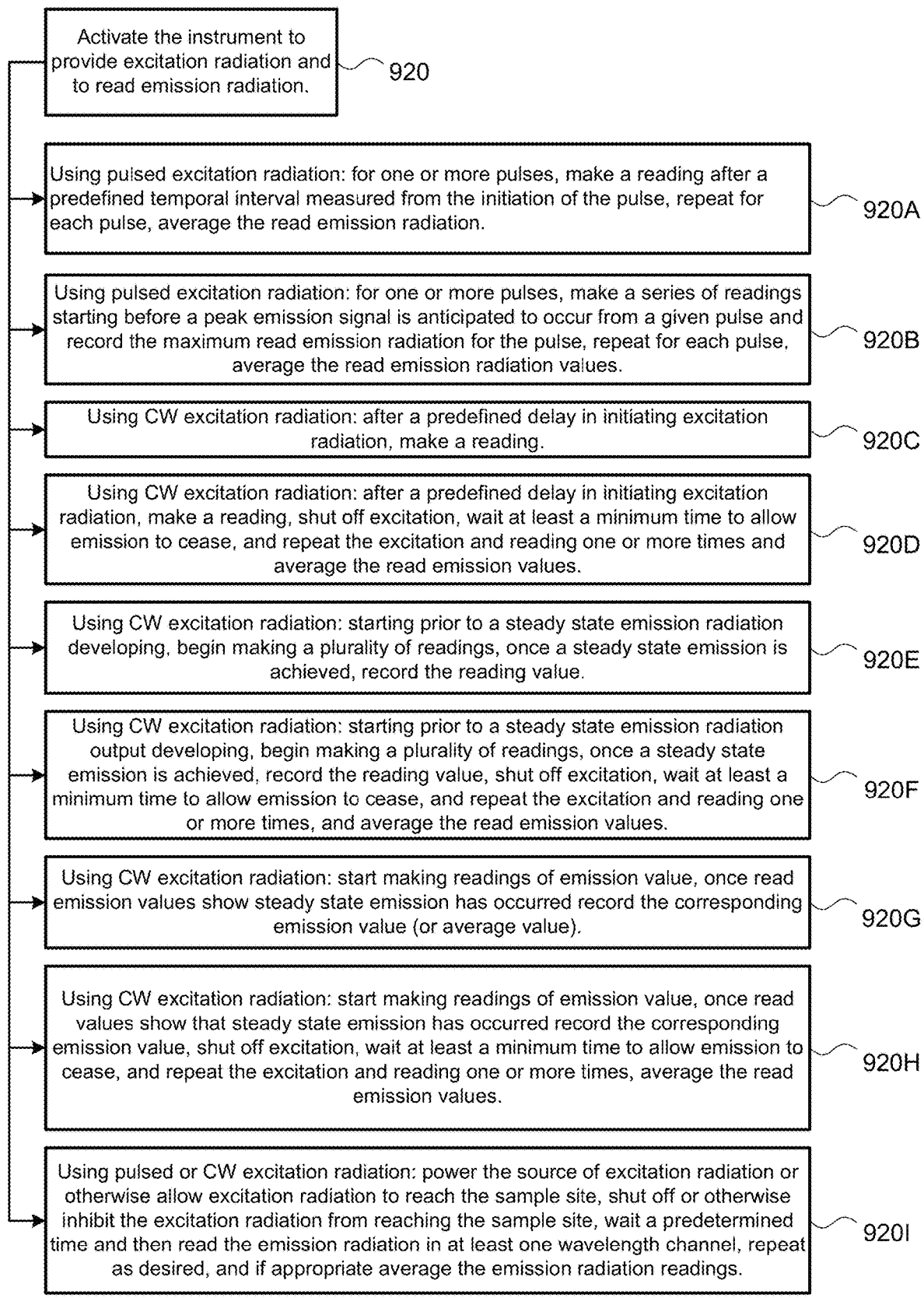
FIG. 9B provides a block diagram setting forth various example processes that may be used in implementing the exposure of a sample to excitation radiation (e.g. activation of instrument's excitation radiation source or otherwise passing excitation radiation onto the sample, e.g. via the opening of a shutter, moving the beam to an aperture path via a moving mirror, actuation of an acousto-optic modulator, or the like) and reading emission radiation as required by the operation of the process of FIG. 9A.

FIG. 9B provides a block diagram setting forth various example processes that may be used in implementing the exposure of a sample to excitation radiation as set forth in block 920 (e.g. activation of instrument's excitation radiation source or otherwise passing excitation radiation onto the sample, e.g. via the opening of a shutter, moving the beam to an aperture path via a moving mirror, actuation of an acousto-optic modulator, or the like) and reading emission radiation as required by the operation of the process of FIG. 9A. Blocks 920A to 920I each set forth an alternative data gathering method. Other data gathering methods are possible and will be apparent to those of skill in the art upon review of the teachings herein. For example, some such methods may involve use of data simplification methods other than averaging.

Figure 10A:
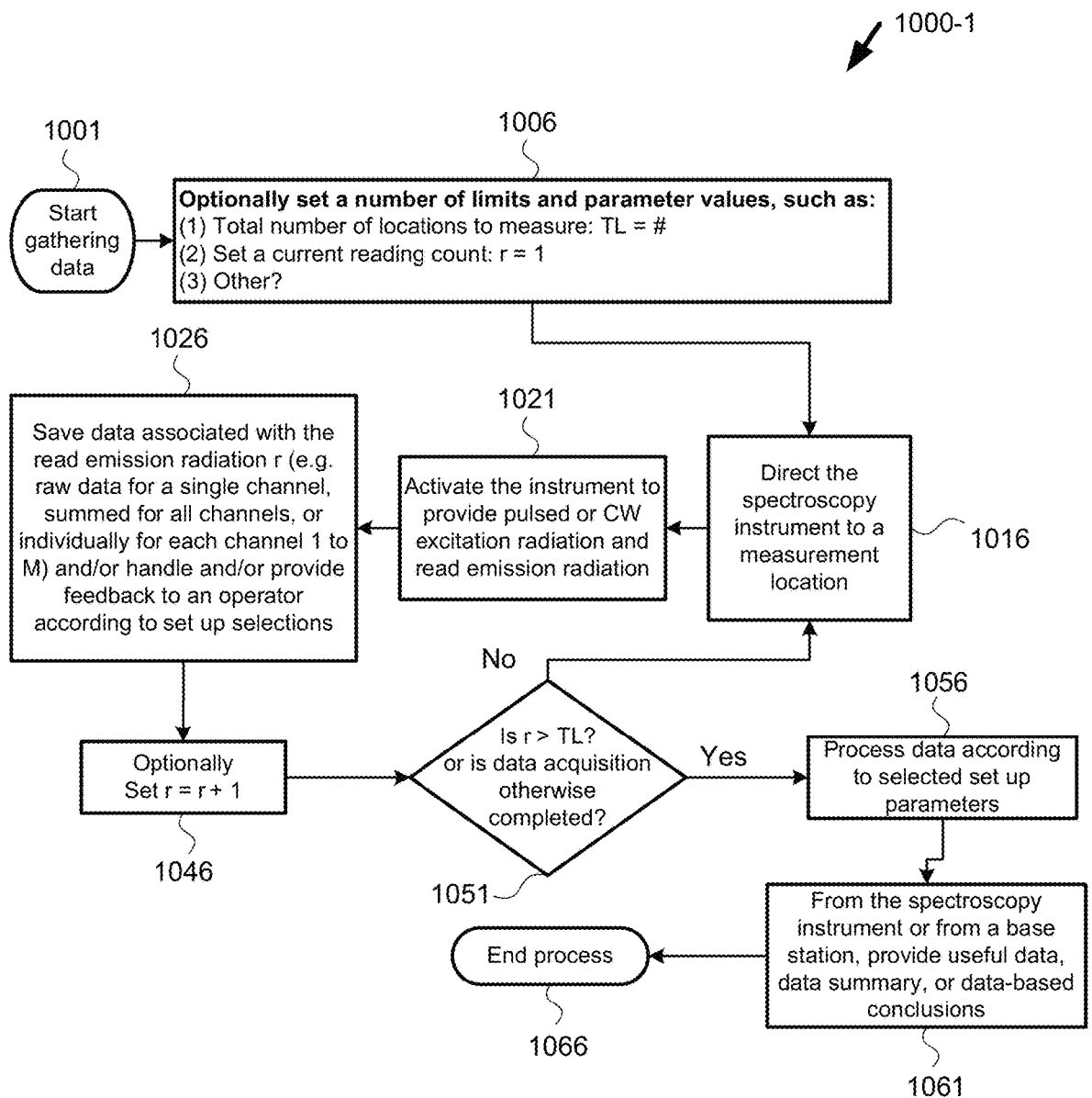
FIG. 10A provides an example flowchart for making in situ measurements of unknown samples and quantities involving a single measurement per location.

FIG. 10A provides an example flowchart for making in situ measurements of unknown samples and quantities involving a single measurement per location using a stationary or slowly moving spectroscopy instrument. In this example, the supplied exposure radiation or excitation radiation may take the form of pulsed radiation or continuous wave (CW) radiation. The application of such radiation and reading of emission radiation may be performed in any desired manner so long as recorded values can be correlated to calibration information such as that obtained by the process of FIG. 9A, e.g. when using an exposure and reading method such as one of those exemplified in FIG. 9B. In some pulsed exposure embodiments, it may be desirable to make, or retain, emission radiation readings when they are at their peak value (i.e. after waiting long enough so that the excitation radiation has produced a peak value but not waiting so long that the emission radiation has begun decreasing). In other embodiments, it may be desirable to make emission readings after a predefined period after initiation of exposure to excitation radiation whether or not emission radiation values are increasing or decreasing. In some embodiments, multiple values may be used such that emission growth or emission decay may be taken into consideration when ascertaining the identity of an unknown material or when determining a concentration value. In some such embodiments, some readings may be made during application of excitation radiation and others may be made after excitation radiation has been cut off, the time of such readings may be based on initial exposure to the excitation radiation or based on time of shutting off the emission radiation. In some CW embodiments, similar consideration may be made. In the process of FIG. 10A it is preferred that the measurements be made while the instrument and the surface are in fixed relative positions however, it is possible that readings can be accurately made when the instrument (i.e. in terms of the measurement area) is moving slowly enough relative to the surface. In some embodiments, the simplest calibration correlation may occur when the excitation and measurement parameters used during initial calibration are again used during reading of unknown samples and/or samples of unknown concentration.

The in-situ data gathering process of FIG. 10A starts with block 1001 and then moves to block 1006 which calls for the setting of a number of limits and parameter values such as total number of locations to measure (TL) and setting a current read count (r). Other setting parameters may include, for example: (1) Indicating whether a chemical identity is to be displayed with each reading (CI), (2) Indicating whether a calibrated areal concentration will be displayed with each reading (AC); (3) Indicating whether an uncalibrated areal concentration will be displayed with each reading (ACU); (4) Indicating whether a transfer of data (e.g. wirelessly) will occur to a base station (e.g. a programmed computer) after each reading (DT); (5) Indicating whether data will be stored with each reading for later download to a base station (DS); and (6) Indicating whether the spectroscopic instrument will be operated directly or remotely (O). From block 1006 the process moves to block 1016 which calls for directing the instrument to a measurement location and then to block 1021 which calls for activating the instrument to provide excitation radiation and reading of emission radiation. The operations of block 1021 may occur using one of the processes noted in FIG. 9B or by using some other process. From block 1021 the process moves to block 1026 which calls for saving data that is obtained (e.g. in one of several different examples forms) and/or providing feedback to an operator according to set up options and instrument capabilities. From block 1026 the process moves to block 1046 where r is incremented by 1. Next the process moves to decision block 1051 where a determination is made as to whether r is greater than TL or if data acquisition is otherwise completed. If yes, the process moves to block 1056 and if not, the process loops back to block 1016 for more data gathering. When at block 1056, the obtained data is processed according to set up options and then in block 1061 the spectroscopic instrument or a base station provides useful data, a data summary, data-based conclusions after which the process ends at block 1066.

In some embodiments, during the taking of measurements, the spectroscopic instrument is held in a fixed position (relative to a local XY position along the surface that is being measured and at a position touching or more preferably slightly above the surface (e.g. between about ¼" to 2" or more preferably between ½" to 1") and orientation (along a surface normal in Z) relative to the subject surface during exposure and reading, while in other embodiments the spectroscopic instrument may undergo some movement in X and Y during irradiation and reading so long as the movement is slow and/or does not deviate from the irradiated location by too large of a fraction of the measurement spot size. Such movement may be limited to a given fraction of the measurement spot size during the time it takes to complete a measurement. For example, a maximum acceptable fraction of the measurement size may be set to <1/16, <⅛, <⅙, <¼, or even <½ of the measurement size. In other embodiments it may be possible to extend this to <⅔, <¾ or even a larger amount of the measurement size (e.g. diameter of the readable area particularly if the readable area is much smaller than an excitation area). Measurement diameter may be, for example, <1 mm, <3 mm, <5 mm, or even more than 10 mm. The time it takes to complete sample exposure or excitation and associated reading may be, for example, <0.05 seconds, <0.1 seconds, <0.2 seconds, <0.4 seconds, or than 0.8 seconds, or even more than 1.6 seconds.

In the embodiment of FIG. 10A a measurement region of a spectroscopic instrument may be moving sufficiently slow (i.e. slow-moving speed—SMS) under the following condition:

$$SMS<(MD*MAMF) \div (PET \text{ or } CWET)$$

Where,
SMS=Slow Moving Speed,
MD=Measurement Diameter,
MAMF=Maximum Acceptable Measurement Fraction,
PET=Pulsed Excitation Time and/or Pulse Extinction Time, and
CWET=Continuous Wave Excitation Time over an area prior to making a reading.

Figure 10B:
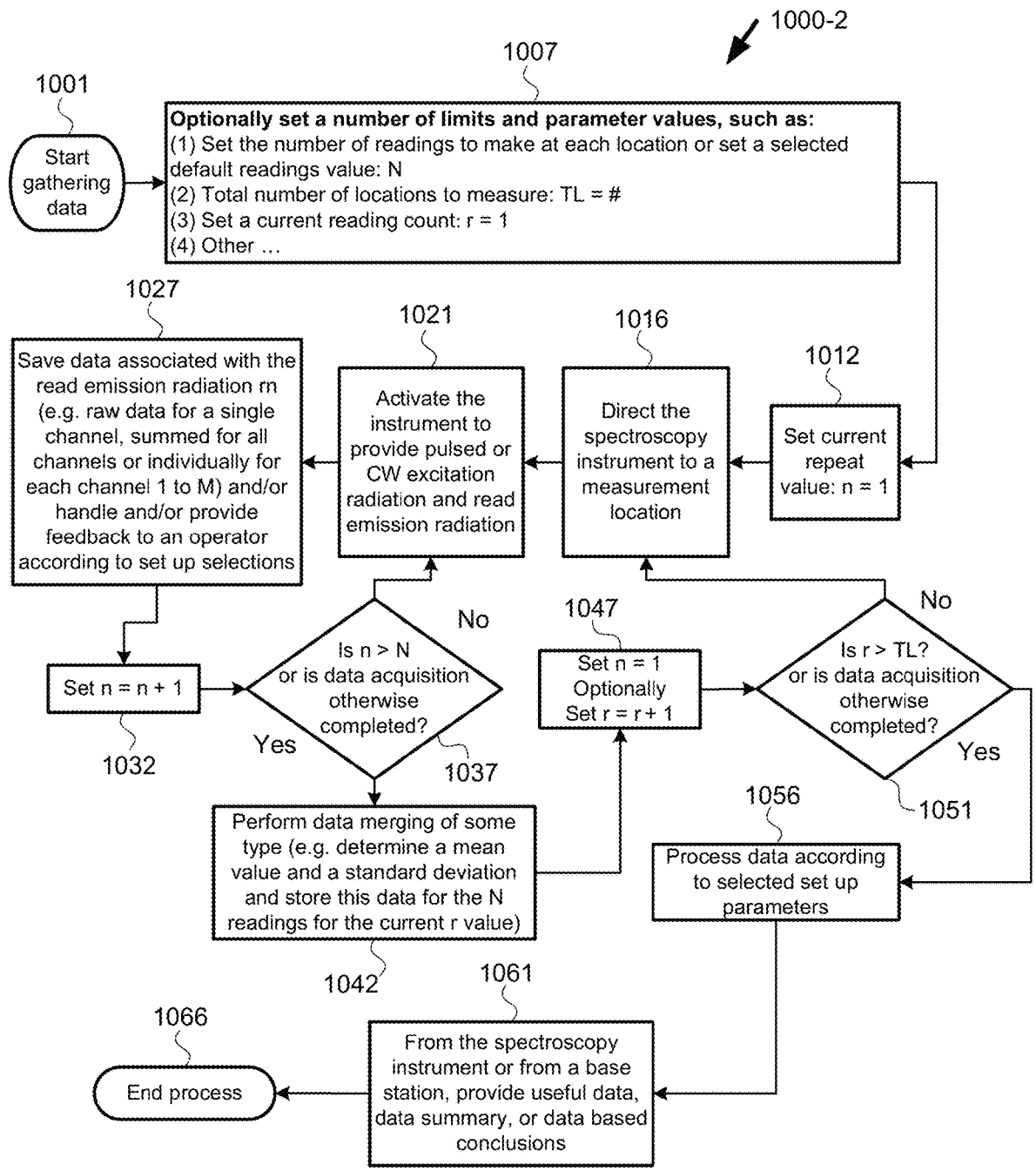
FIG. 10B provides an example flowchart for making a plurality (N) in situ measurements of unknown samples and quantities.

FIG. 10B provides an example flowchart similar to that of FIG. 10A with the exception that instead of making a single reading at each location, a plurality of N in situ measurements of unknown samples and/or quantities per location will be made and wherein some form of data averaging or other data merging will occur. In the process of FIG. 10B it is preferred that the measurements be made while the instrument and the surface are in fixed relative positions however, it is possible that readings can be accurately made when the movement of the instrument (i.e. in terms of the measurement area) is moving slowly enough relative to the surface. The example of FIG. 10B closely follows the example of FIG. 10A with a few exceptions: (1) In a block 1007 (instead of 1006) an additional set up parameter includes the number of readings N to make at each location; (2) In block 1012 a current read value n is set to one; (3) In block 1032, the read value n is incremented by 1; (4) In decision block 1037 a determination is made as to whether n is greater than N. If not, the process loops back to block 1021 for more readings, and if so, the process moves to block 1042 for the merging of the N readings into a more useful form. From block 1042 the process moves to block 1047 where n is reset to 1 and r is incremented by one and then the process moves to block 1051 where the process continues as it did in the process of FIG. 10A. As with all other embodiments discussed herein numerous variations of the present method are possible with some such variations derived from various alternatives and/or elements of other embodiments discussed herein. In some variations additional setup limits or parameters may be used, such as, for example those set forth with regard to the setup options for the process of FIG. 10A.

In the embodiment of FIG. 10B a measurement region of a spectroscopic instrument may be moving sufficiently slow under one of the following conditions:

$$SMS<(MD*MAMF) \div [(PET+TG)*N]$$

or $$SMS<(MD*MAMF) \div (CWET*N)$$

Where,
SMS=Slow Moving Speed,
MD=Measurement Diameter,
MAMF=Maximum Acceptable Measurement Fraction,
PET=Pulsed Excitation Time and/or Pulse Extinction Time, and
TG=Time Gap between pulses, and
CWET=Continuous Wave Excitation Time Between Readings
N=Number of reading Processes for using calibration data may differ significantly based on the assumptions that are made and on whether the assumptions are to be validated as part of the process. In the example process of FIG. 11A an assumption is made that the material is known and that assumption is never questioned, in the example process of FIG. 11b an assumption that the material is known is made but the assumption is tested during the course of the process, and in FIG. 11C no precise assumption concerning the material is made but instead the type of material is determined during the process.

Figure 11A:
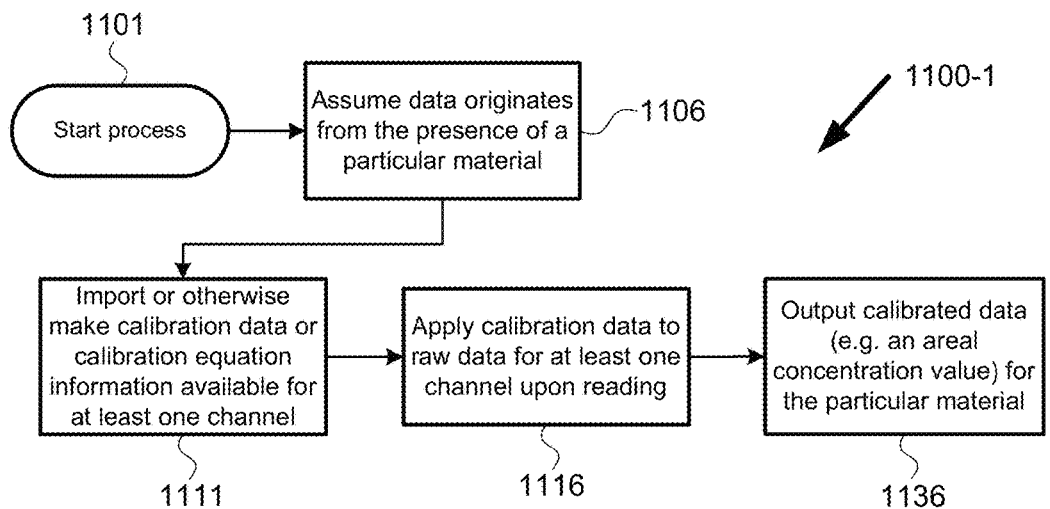
FIG. 11A provides a flowchart for using calibration data where a sample of unknown concentration is assumed to be of a particular material and its concentration is determined.

FIG. 11A provides an example flowchart for a process 1100-1 for using calibration data where a sample of unknown concentration is assumed to be of a particular material and its concentration is determined. The process begins with block 1101 and moves to block 1106 wherein an assumption of the material type is made. From block 1106 the process moves to block 1111 wherein calibration information for the particular material is imported or otherwise made available. From block 1111 the process moves to block 1116 where the calibration data is applied to the raw data for at least one channel and in block 1136, calibrated data is output so as to provide an areal concentration value for the assumed material. In variations of the process additional steps may be added, instead of using data from at least one channel, data from multiple channels may be used or combined in some manner (e.g. in a manner similar to how original calibration data was processed). In some embodiments, the assumption of known material type may be based on prior readings that identified the material, logical assertions derived from knowledge of how a facility or piece of equipment has been used, or based on some other criteria.

Figure 11B:
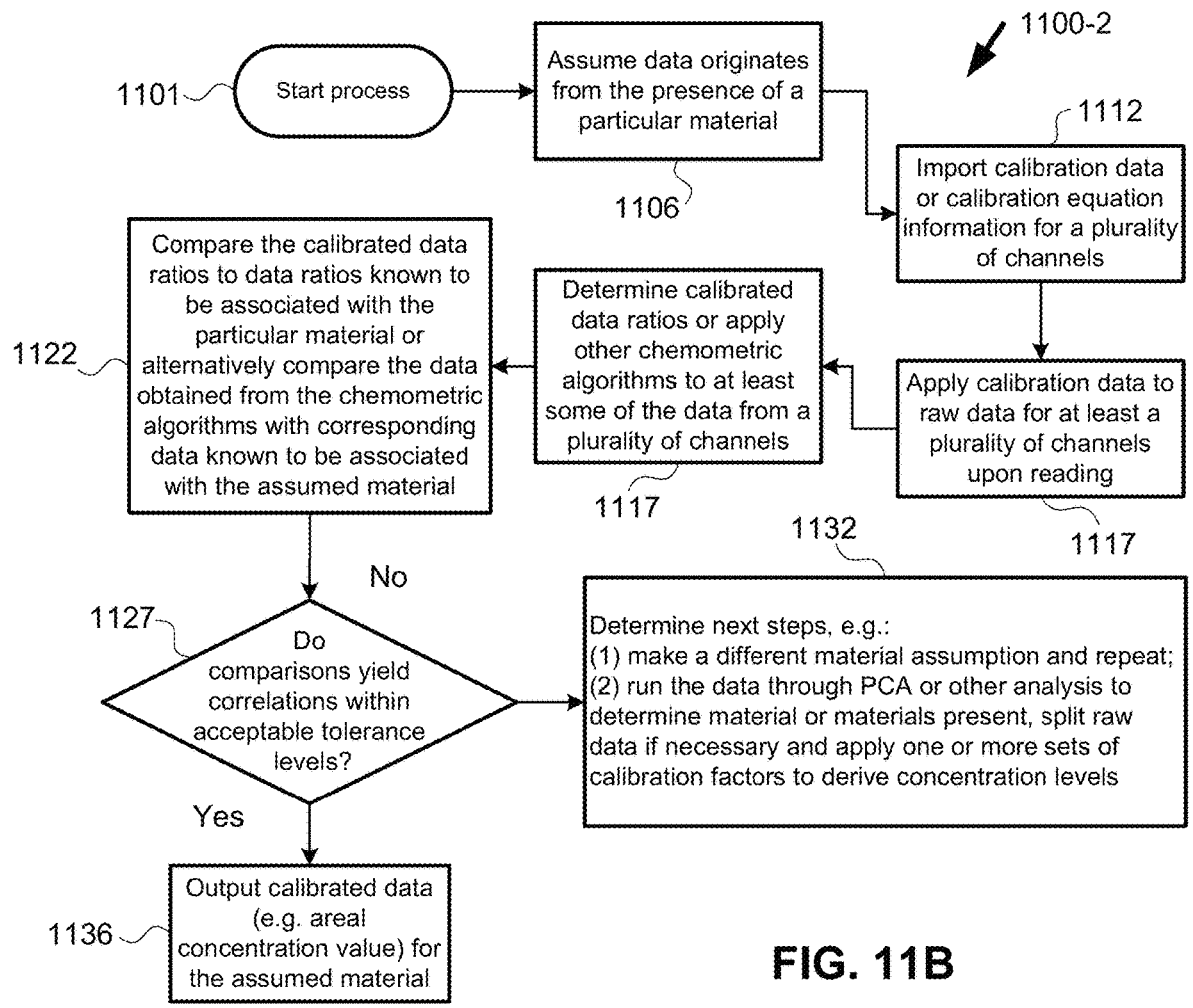
FIG. 11B provides a flowchart for using calibration data where a sample of unknown concentration is assumed to be of a particular material but where the validity of the assumption is checked prior to outputting calibrated concentration information.

FIG. 11B provides a flowchart for a process 1100-2 for using calibration data where a sample of unknown concentration is assumed to be of a particular material but where the validity of the assumption is checked prior to outputting calibrated concentration information. Like the flowchart of FIG. 11A, the process begins with block 1101 and moves to block 1106 wherein an assumption of the material type is made. From block 1106 the process moves to block 1112 wherein calibration information for a plurality of spectral channels of the assumed material is imported or otherwise made available. From block 1112 the process moves to block 1117 where the raw data ratios from different channels are determined or other chemometric algorithms are applied to the raw data. From block 1117 the process moves to block 1122 where obtained ratios from the measured data are compared to ratios for the assumed material or alternatively chemometric data for the measured data is compared to chemometric information for the assumed material. From block 1122 the process moves to decision block 1127 where a decision is made as to whether the assumed material matches the material identified by the data. If yes, the process moves to block 1136 where calibrated data is output so as to provide an areal concentration value for the material. If the answer is no, the process moves to block 1132 where a determination of next steps occurs. An example next step involves making a different assumption and repeating the process. Another next step may involve, if not already done in step 1122, completing any PCA or other analysis to actually ascertain the material found, or the most likely material found, based on the data and potentially based on assumptions concerning other materials that would likely be present. Other next steps are also possible.

Figure 11C:
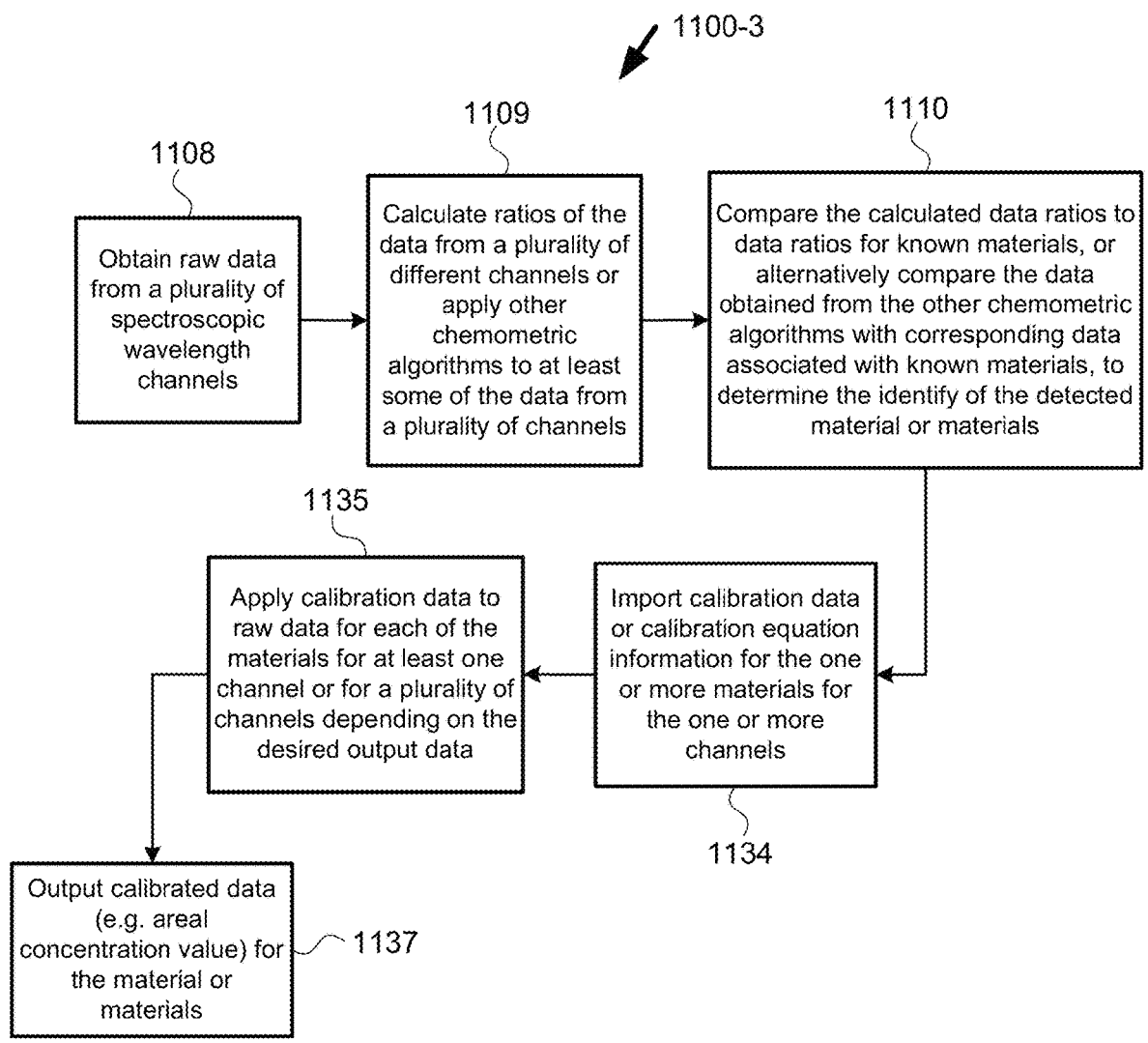
FIG. 11C provides a flowchart for using calibration data wherein a sample is read, and the material or materials present are ascertained prior to determining the concentration value or values.

FIG. 11C provides a block diagram for using calibration data wherein a sample is read, and the material or materials present are ascertained prior to determining the concentration value or values. The process 1100-3 of FIG. 11C starts with 1108 which calls for obtaining raw data from a plurality of spectroscopic channels. The process then moves to block 1109 which calls for calculating ratios of the data obtained from a plurality of different channels or applying other chemometric algorithms to at least some of the data from a plurality of channels. From block 1109 the process moves forward to block 1110 which calls for comparing the calculated data ratios to data ratios for known materials, or alternatively comparing the data obtained from the other chemometric algorithms with corresponding data associated with known materials to determine the identity of the detected material or materials. From block 1110 the process moves to block 1134 which calls for the importation of calibration data or calibration equation information to the one or more identified materials for one or more channels. From block 1134 the process moves to block 1135 which calls for applying calibration data to the raw data for at least one channel or for a plurality of channels depending on the desired output data. From block 1135 the process moves to block 1137 which calls for the outputting of calibrated data in the form of one or more areal concentration values.

Numerous variations of the embodiments of FIGS. 11A-110 are possible and will be apparent to those of skill in the art upon review of the teachings herein.

Figure 11D:
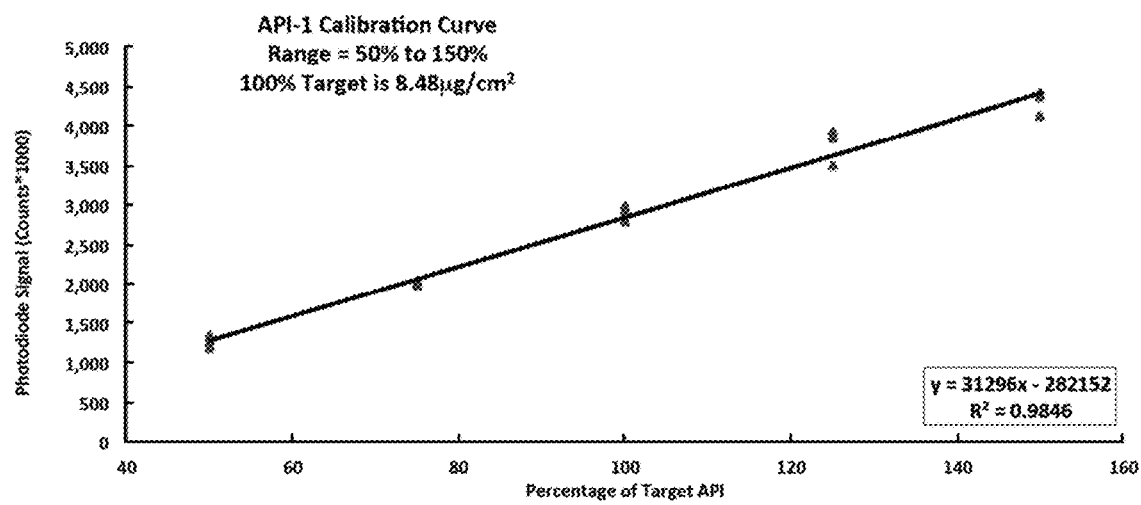
FIG. 11D provides a sample calibration plot of signal strength of raw data versus percentage of a target concentration value with a linear regression equation that can be used to correlate raw data of samples of unknown concentration to actual concentration values in micrograms/cm2.

FIG. 11D provides a sample calibration plot of signal strength of raw data versus percentage of a target concentration value with a linear regression equation that can be used to correlate raw data of samples of unknown concentration to actual concentration values in micrograms/cm$^2$.

Figure 11E:
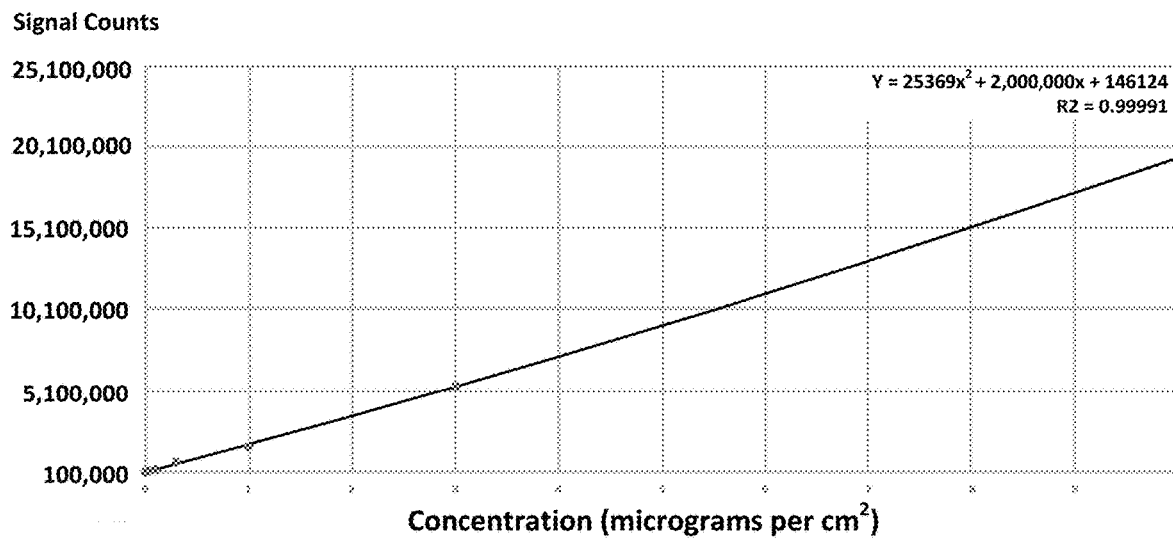
FIG. 11E provides a sample calibration plot of signal strength of raw data versus concentration of a particular material in micrograms/cm2 along with a quadratic regression equation that is derived from the data which in turn can be used to correlate raw data of samples of unknown concentration to actual concentration values.

FIG. 11E provides a sample calibration plot of signal strength of raw data versus concentration of a particular material in micrograms/cm$^2$ along with a quadratic regression equation that is derived from the data which in turn can be used to correlate raw data of samples of unknown concentration to actual concentration values.

FIGS. 12A-1 and 12A-2 to 12D-1 to 12D-2 provide both block diagrams and schematic representations of four example processes for controllably dispensing known volumes of material in the form of individual droplets from computer-controlled syringes. Other dispensing processes are possible and will be apparent to those of skill in the art upon review of the teachings herein.

Figures 1, 12A:
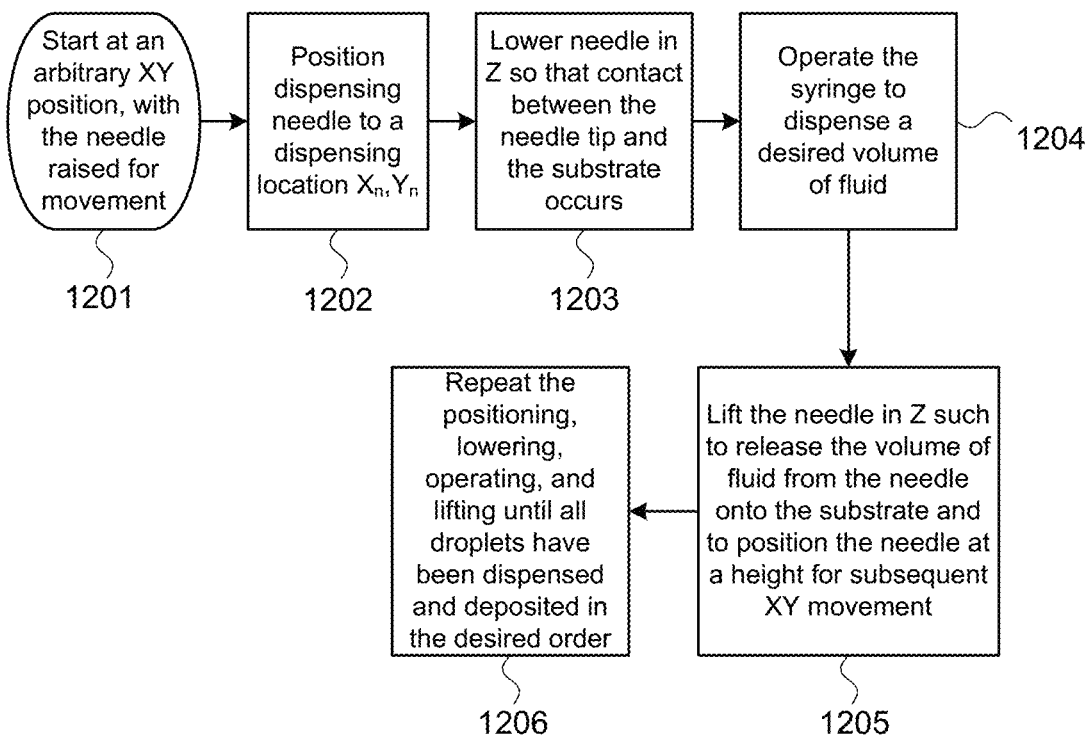
Figures 2, 12A:
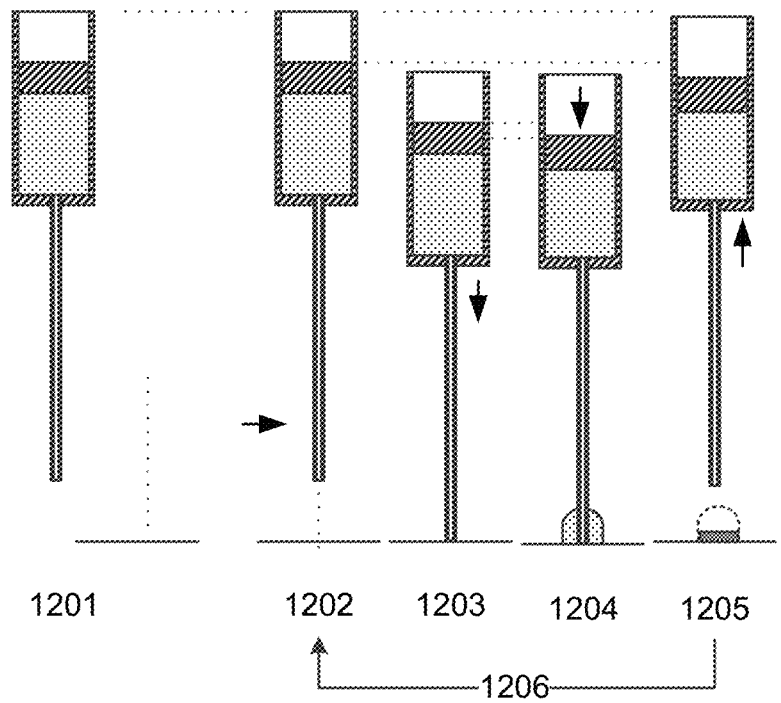

FIG. 12A-1 provides a block diagram while FIG. 12A-2 provides a schematic illustration of a droplet dispensing process according to a first process where at the time of syringe operation (to dispense a given volume as a droplet) a needle tip of the syringe is in contact with a dispensing substrate and after dispensing, the tip of a needle of the syringe is raised to a height above the substrate that is greater than the height of an unreleased droplet.

The process of FIGS. 12A-1 and 12A-2 are shown in six blocks 1201-1206 with the block operations and the corresponding schematic depictions provided with the same reference numbers. The process starts with block 1201 and with the computer-controlled syringe at an arbitrary XY position with the tip of the needle located sufficiently above a substrate to allow XY movement without risk of collision. The process then calls for the syringe to move to an $X_nY_n$ dispensing location (i.e. a needle location for droplet$_n$) as set forth in block 1202. Next the tip of the syringe is lowered in Z until contact is made with the substrate (detection can occur in a number of different ways) as set forth in block 1203. The syringe is operated to dispense a precisely known volume of material with the needle touching the substrate such that the amount of material is released but remains joined to the substrate and the needle as set forth in block 1204. After the dispensing operation, the syringe is lifted in Z to a height above the height of an attached droplet such that the material is stripped from the needle (by a preference to cling to the substrate) and remains in contact with the substrate as set forth in block 1205 whereafter solvent holding the material evaporates leaving behind a dried deposit of material having a precisely known amount of material. Finally, the process steps are repeated until all droplets are dispensed as set forth in block 1206.

Figures 1, 12B:
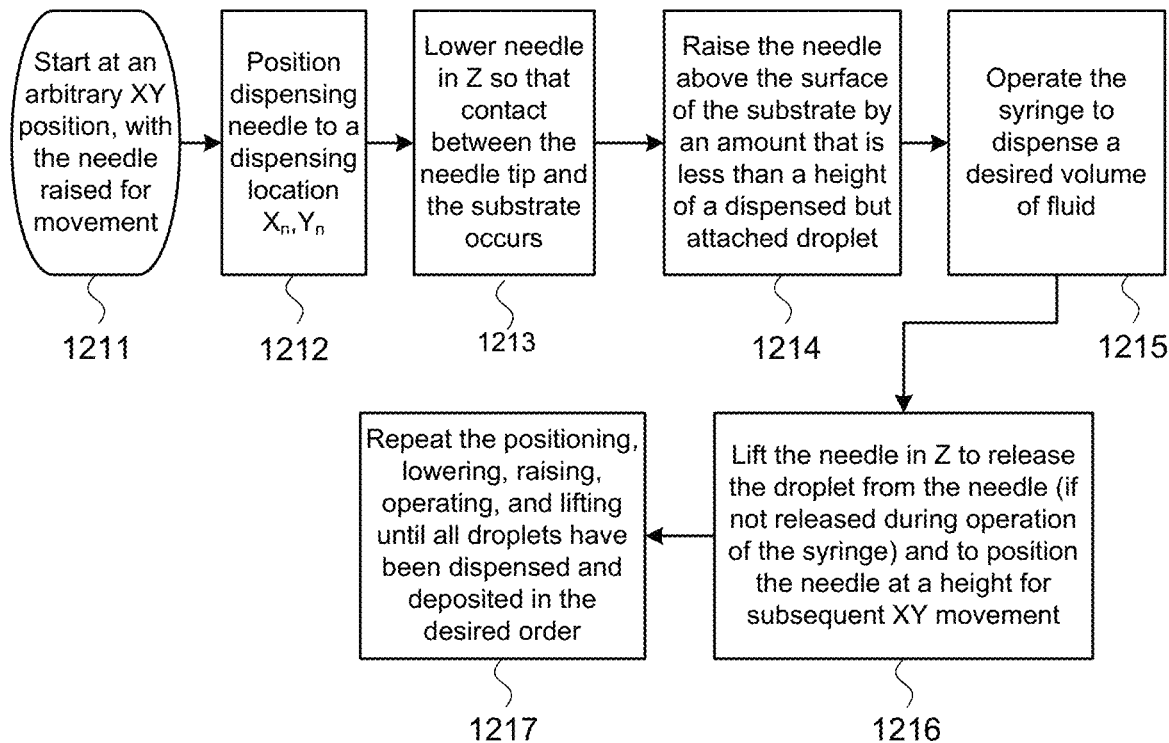
Figures 2, 12B:
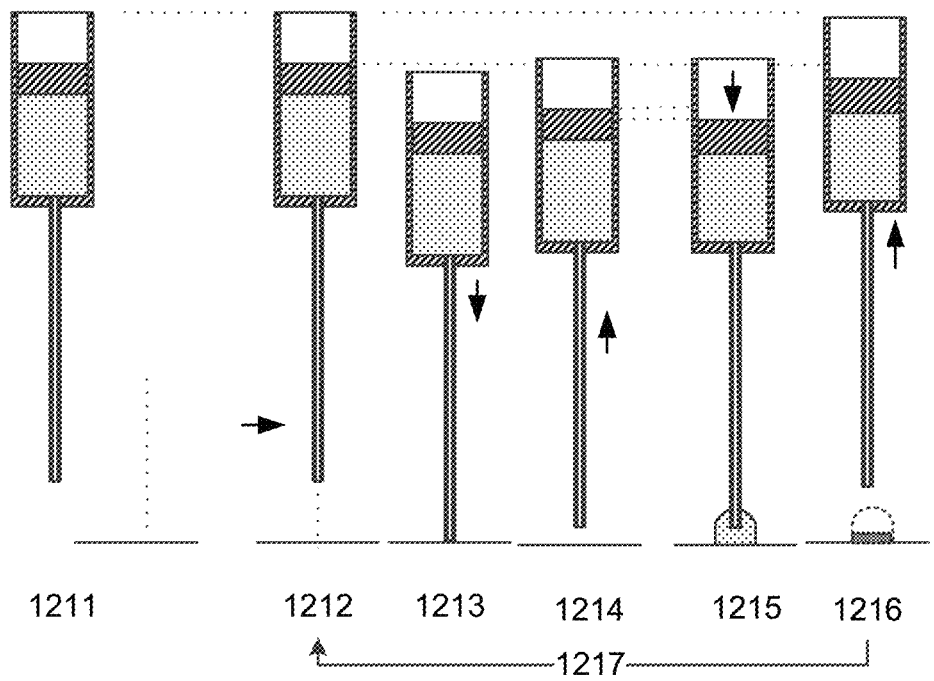

FIG. 12B-1 provides a block diagram while FIG. 12B-2 provides a schematic illustration of a droplet dispensing process according to a second process where at the time of syringe operation (to dispense a given volume as a droplet) a tip of the dispensing needle of the syringe is above a substrate surface by an amount smaller than an unreleased droplet height where the distance is set by first touching the substrate with the needle (prior to dispensing) and then retracting the needle a desired amount to a height above the substrate that is less than a height of an unreleased droplet.

The process of FIGS. 12B-1 and 12B-2 is shown in seven blocks 1211-1217 with the block operations and the corresponding schematic depictions provided with the same reference numbers. The process starts with block 1211 and with the computer-controlled syringe at an arbitrary XY position with the tip of the needle located sufficiently above a substrate to allow XY movement without risk of collision. The process then calls for, in block 1212, the syringe to move to an $X_nY_n$ dispensing location (i.e. a needle location for droplets$_n$). Next the tip of the syringe is lowered in Z until contact is made with the substrate (detection can occur in a number of different ways) as set forth in block 1213. The syringe is then lifted in Z from the substrate by an amount less than the height of an unreleased droplet of material as set forth in block 1214. The syringe is operated to dispense a precisely known volume of material such that a droplet while being dispensed and still clinging to the needle makes contact with the substrate which may or may not result in the release of the material from the needle as set forth in block 1215. After the dispensing operation, the syringe is lifted in Z to a height above a height of an released volume of material such that the material is striped from the needle (if not already stripped during the previous operation) and remains in contact with the substrate as set forth in block 1216 whereafter solvent holding the material evaporates leaving behind a dried deposit of material having a precisely known amount of material. Finally, the process steps are repeated until all droplets are dispensed as set forth in block 1217.

Figures 1, 12C:
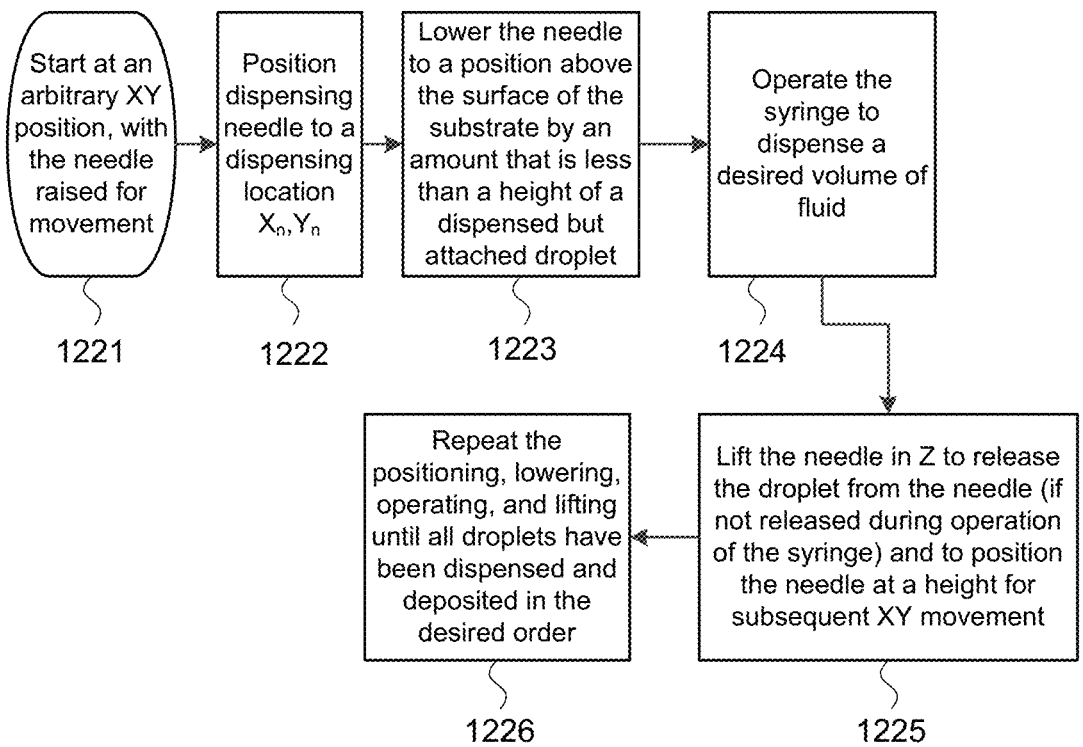
Figures 2, 12C:
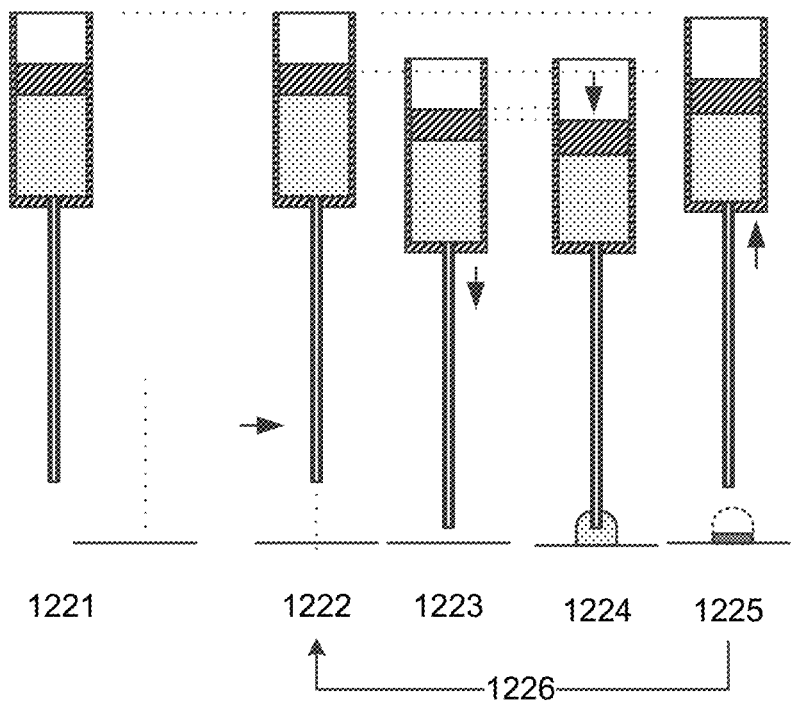

FIG. 12C-1 provides a block diagram while FIG. 12C-2 provides a schematic illustration of a droplet dispensing process according to a third process where at the time of dispensing a given volume (as a droplet) from a tip of a syringe dispensing needle, the tip is above a substrate surface by an amount smaller than a droplet height where the distance is set by moving the needle downward and stopping movement prior to the needle making contact with the substrate and after dispensing raising the needle to a height above the substrate that is greater than the height of an unreleased droplet.

The process of FIGS. 12C-1 and 12C-2 are shown in six blocks 1221-1226 with the block operations and the corresponding schematic depictions provided with the same reference numbers. The process starts with block 1221 and with the computer-controlled syringe at an arbitrary XY position with the tip of the needle located sufficiently above a substrate to allow XY movement without risk of collision. The process then calls for the syringe to move to an $X_nY_n$ dispensing location (i.e. a needle location for droplet$_n$) as set forth in block 1222. Next the tip of the syringe is lowered in Z until it is located above the surface of the substrate but closer to the substrate than a height of an attached droplet as set forth in block 1223. The syringe is operated to dispense a precisely known volume of material with the needle located from the substrate within the height of an attached droplet such that upon dispensing the droplet bridges the gap between the needle tip and the substrate as set forth in block 1224. After the dispensing operation, the syringe is lifted in Z to a height above a height of an attached droplet such that the droplet is striped from the needle (e.g. by a preference to cling to the substrate) and remains in contact with the substrate as set forth in block 1225 whereafter solvent holding the material evaporates leaving behind a dried deposit of material having a precisely known amount of material. Finally, the process steps are repeated until all droplets are dispensed as set forth in block 1226.

Figures 1, 12D:
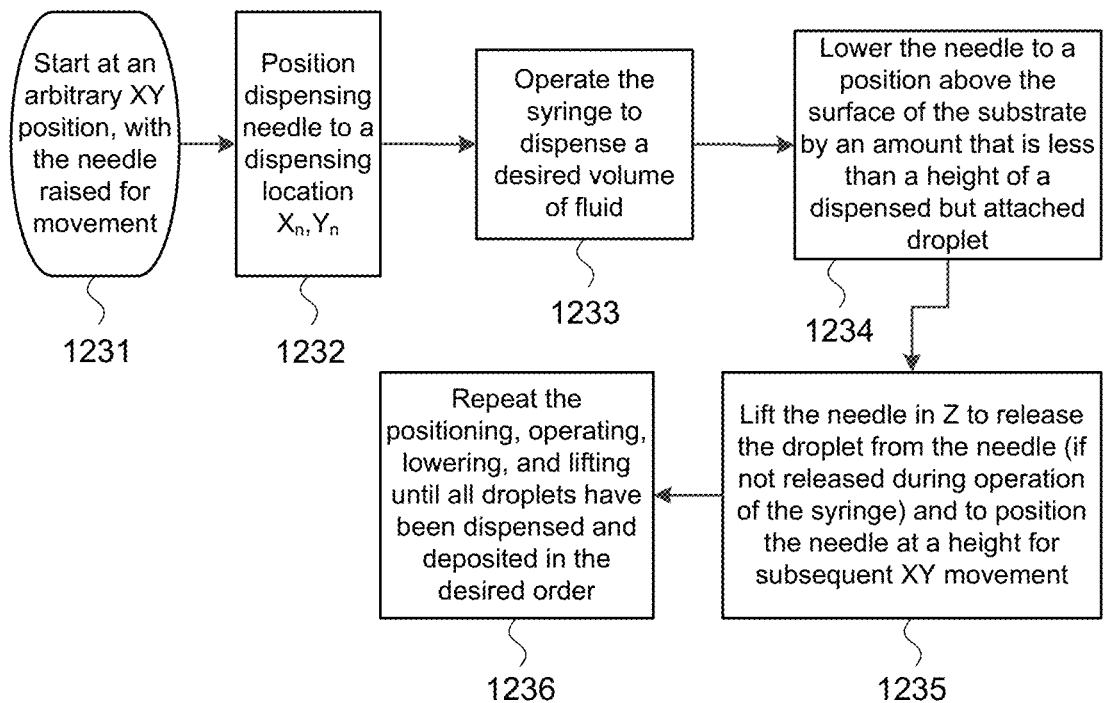
Figures 2, 12D:
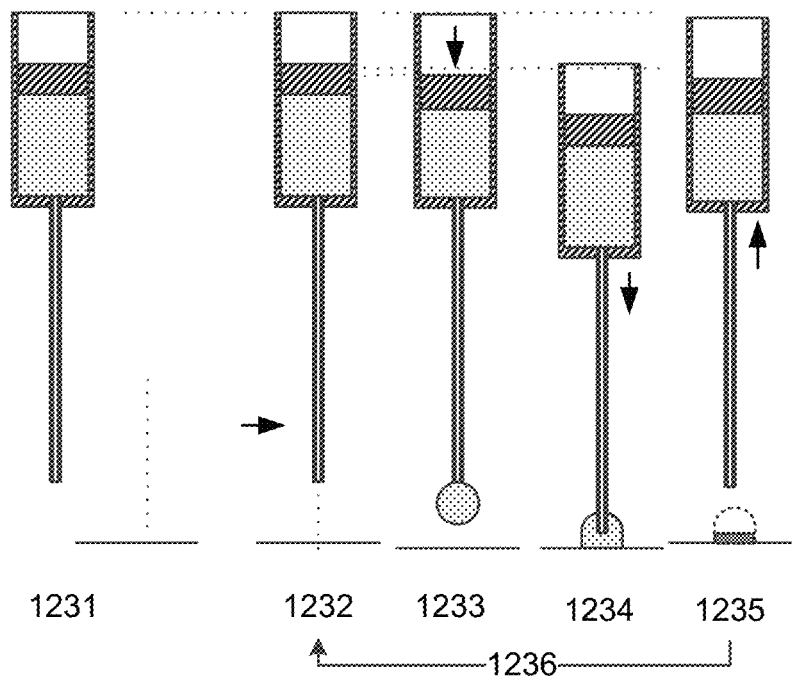

FIG. 12D-1 provides a block diagram while FIG. 12D-2 provides a schematic illustration of a droplet dispensing process according to a fourth process where at the time of dispensing a known volume (as a droplet) from a tip of a syringe dispensing needle, the tip is above a substrate surface by an amount greater than an unreleased droplet height and where after dispensing the needle tip is lowered to a position above the substrate less than a height of the unreleased droplet after which the tip of the needle is raised away from the substrate by an amount greater than a height of an unreleased droplet.

The process of FIGS. 12D-1 and 12D-2 are shown in six blocks 1231-1236 with the block operations and the corresponding schematic depictions provided with the same reference numbers. The process starts with block 1231 and with the computer-controlled syringe at an arbitrary XY position with the tip of the needle located sufficiently above a substrate to allow XY movement without risk of collision. The process then calls for the syringe to move to an $X_nY_n$ dispensing location (i.e. a needle location for droplet$_n$) as set forth in block 1232. The syringe is operated to dispense a precisely known volume of material with the needle located above the substrate by an amount greater than a height of an unreleased droplet which cannot reach the substrate without dropping from the needle as set forth in block 1233. Next the needle is lowered to within the height of an unreleased droplet from the substrate which causes the droplet to bridge the gap between the needle and the substrate and may or may not result in the release of the droplet from the needle as set forth in block 1234. Next the syringe is lifted in Z to a height above a height of an attached droplet such that the droplet is striped from the needle (by a preference to cling to the substrate) and remains in contact with the substrate as set forth in block 1235 whereafter solvent holding the material evaporates leaving behind a dried deposit of material having a precisely known amount of material. Finally, the process steps are repeated until all droplets are dispensed as set forth in block 1236.

Final Comments

Various embodiments of the invention have been discussed above with some directed to printing material on coupons or on in situ surfaces wherein the printed materials are dispensed in discrete droplets of precisely known size and volume concentration and wherein the printing occurs with sufficient uniformity in droplet positioning and close enough center-to-center spacing that a spectroscopy instrument with a certain measurement area can obtain relatively uniform readings from location-to-location or effective averaging or other statistical manipulations can provide adequate repeatability such that deposited materials can be used as calibration samples for spectroscopy instruments without need for other methods of confirming sample concentration levels. Other embodiments have been directed to methods of using such samples in calibrating spectroscopy instruments while still others have been directed to using the calibrated spectroscopy instruments in a variety of applications and especially applications where trace surface concentrations are of interest. While embodiments have focused on surface concentrations, methods and apparatus of various embodiments of the present invention may have application in calibrating spectroscopic instruments for reading volume concentrations as well as areal concentrations. While many embodiments of the invention are capable of providing both material identification and material quantification, not all useful processes need to provide both of these benefits. In some embodiments, materials may be known in advance and only quantification is required and, in such embodiments, apparatus and methods with reduced capabilities may be optimally deployed alone or in combination with a smaller number of more powerful instruments. Similarly, in some embodiments, quantification may be less important than identification and, in such cases, a single instrument may be capable of providing one functionality, or the other, or both, as the case may be. In some embodiments, instruments may be designed, programmed, and calibrated for specific applications while in other cases instruments may be designed, programmed, and calibrated for more general use. While a significant advantage to many embodiments of the present invention involve rapid calibration and/or rapid recalibration possibilities provided by the known concentration properties of printed calibration samples as well as their capability for reuse, it is understood that not every application needs to make direct use of each of these advantages.

Though various portions of this specification have been provided with headers, it is not intended that the headers be used to limit the application of teachings found in one portion of the specification from applying to other portions of the specification. For example, alternatives acknowledged in association with one embodiment, are intended to apply to all embodiments to the extent that the features of the different embodiments make such application functional and do not otherwise contradict or remove all benefits of the adopted embodiment. Various other embodiments of the present invention exist. Some of these embodiments may be based on a combination of the teachings set forth herein with various teachings incorporated herein by reference.

It is intended that the aspects of the invention set forth herein represent independent invention descriptions which Applicant contemplates as full and complete invention descriptions that Applicant believes may be set forth as independent claims without need of importing additional limitations or elements, from other embodiments or aspects set forth herein, for interpretation or clarification other than when explicitly set forth in such independent claims once written. It is also understood that any variations of the aspects set forth herein represent individual and separate features that may form separate independent claims, be individually added to independent claims, or added as dependent claims to further define an invention being claimed by those respective dependent claims should they be written.

In view of the teachings herein, many further embodiments, alternatives in design and uses of the embodiments of the instant invention will be apparent to those of skill in the art. As such, it is not intended that the invention be limited to the illustrative embodiments, alternatives, and uses described above but instead that it be solely limited by the claims presented hereafter, subsequently amended, or subsequently set forth in an application that claims priority to this application. In view of the teachings herein, many further embodiments, alternatives in design and uses of the instant invention will be apparent to those of skill in the art.

I claim:

1. A method of calibrating a spectroscopic surface analysis instrument providing both identification of at least one material of interest and a quantitative indication of the at least one material of interest that is detected, the method comprising:
    (a) providing a spectroscopic surface analysis instrument, comprising:
        (i) a housing;
        (ii) a source in the housing that is capable of producing excitation radiation that is directed onto a surface to be examined;
        (iii) at least one optical element within the housing for performing at least one function selected from the group consisting of: (1) directing excitation radiation onto the surface to be examined, and (2) receiving emission radiation from at least one location on a surface undergoing examination;
        (iv) a detector within the housing for detecting, as detected emission radiation, at least a portion of the emission radiation coming from the at least one location; and
        (v) control electronics for operating the instrument;
    (b) providing an electronic circuit, comprising at least one programmed processor and a memory, for determining whether the detected emission radiation corresponds to at least one material of interest, and wherein the determining also provides a quantitative indication selected from the group consisting of: (1) a detected quantity of the at least one material of interest at the at least one location, (2) a detected quantity of the at least one material of interest being above a predefined level at the at least one location, (3) a detected quantity of the at least one material of interest being below a predefined level at the at least one location, (4) an actual concentration of the at least one material of interest at the at least one location, (5) a concentration of the at least one material of interest being above a predefined level at the at least one location, and (6) a concentration of the at least one material of interest being below a predefined level at the at least one location;
    (c) providing an electronic circuit for creating and storing quantitative calibration data;
    (d) operating the instrument in a calibration mode, comprising:
        (i) operating the surface analysis instrument to provide excitation radiation onto a plurality of sample surfaces with each sample surface having at least one of the at least one material of interest with a known concentration;
        (ii) collecting data from the detected emission radiation being returned from each sample surface; and
        (iii) processing data that is collected to provide the calibration data for a desired range of concentrations of the at least one material of interest;
    whereby upon use of the instrument to examine a surface to be tested, which may have an unknown material thereon, the detected emission radiation may be compared to the calibration data to ascertain information about the quantitative indication of the at least one material of interest that may be present.

2. A method of calibrating a spectroscopic surface analysis instrument which provides a quantitative indication of at least one material of interest that is detected, the method comprising:
    (a) providing a spectroscopic surface analysis instrument, comprising:
        (i) a housing;
        (ii) a source in the housing that is capable of producing excitation radiation that is directed onto a surface to be examined;
        (iii) at least one optical element within the housing for performing at least one function selected from the group consisting of: (1) directing excitation radiation onto the surface to be examined, and (2) receiving emission radiation from at least one location on a surface undergoing examination;
        (iv) a detector within the housing for detecting, as detected emission radiation, at least a portion of the emission radiation coming from the at least one location; and
        (v) control electronics for operating the instrument;
    (b) providing an electronic circuit, comprising at least one programmed processor and a memory, for providing a quantitative indication selected from the group consisting of: (1) a detected quantity of the at least one material of interest at the at least one location, (2) a detected quantity of the at least one material of interest being above a predefined level at the at least one location, (3) a detected quantity of the at least one material of interest being below a predefined level at the at least one location, (4) an actual concentration of the at least one material of interest at the at least one location, (5) a concentration of the at least one material of interest being above a predefined level at the at least one location, (6) a concentration of the at least one material of interest being below a predefined level at the at least one location;

(c) providing an electronic circuit for creating and storing quantitative calibration data;

(d) operating the instrument in a calibration mode, comprising:

(i) operating the surface analysis instrument to provide excitation radiation onto a plurality of sample calibration surfaces with each sample calibration surface having at least one of the at least one material of interest with a known concentration;

(ii) collecting data from the detected emission radiation being returned from each sample calibration surface; and (iii) processing data that is collected to provide calibration data for a desired range of concentrations of the at least one material of interest;

whereby upon use of the instrument to examine a surface to be tested, the detected emission radiation may be compared to the calibration data to ascertain information about the quantitative indication of the at least one material of interest that may be present.

3. The method of claim 2, wherein the calibration data comprises data selected from the group consisting of: (1) a list of data points obtained from operating in the calibration mode; (2) a list of average values of data obtained for each concentration value; and (3) a best fit equation of signal strength vs. concentration, wherein the providing of excitation radiation to the plurality of sample calibration surfaces occurs in a serial manner, wherein the plurality of sample calibration surfaces are provided from the group consisting of: (1) different sample surfaces being separated from each other by a spacing, (2) different sample surfaces being located on separate substrates, and (3) different sample surfaces being located on a common substrate, and wherein the quantitative indication is selected from the group consisting of: (1) a concentration value, (2) an areal concentration value, and (3) a surface concentration value.

4. The method of claim 2 wherein a signal strength of the detected emission radiation from the surface to be tested is matched to a corresponding signal strength associated with the calibration data from which a quantitative amount of the at least one material of interest may be extracted.

5. The method of claim 2 wherein the plurality of sample calibration surfaces are each formed from a plurality of droplets where an amount of the at least one of the at least one material of interest in each droplet is known a priori.

6. The method of claim 5 wherein the droplets are dispensed at selected locations on an XY grid by a computer-controlled syringe, having a dispensing needle, from a fluid volume having known volumetric concentration of at least one of the at least one material of interest.

7. The method of claim 2 wherein the plurality of sample surfaces are each formed from a plurality of droplets that are dispensed at each of a plurality of locations wherein dispensing occurs with a timing selected from the group consisting of: (1) a subsequent droplet being dispensed on a given location while a previously dispensed droplet at the given location remains, at least in part, in a fluid state and (2) a subsequent droplet being dispensed on a given location while all previously dispensed droplets at the given location have dried.

8. The method of claim 7 wherein the droplets are dispensed to a plurality of dispensing locations using a process selected from the group consisting of:

Process 1:
(i) while a tip of the needle of the syringe is located at a Z-level above a surface of a substrate, positioning the needle to an XY dispensing location;
(ii) lowering the needle until contact with the substrate is made;
(iii) operating the syringe to dispense a droplet having a defined fluid volume, containing a known concentration of at least one of the at least one material of interest;
(iv) lifting the needle along the axis above the substrate, so that the droplet is released and such that the needle tip is a height for XY movement to a next dispensing location; and
(v) repeating (i) to (iv) to dispense at least one droplet at each of a plurality of locations;

Process 2:
Steps (i)-(v) of Process 1 wherein each of a plurality of successive XY droplet dispensing locations is spaced from an immediately preceding XY droplet dispensing location by a distance such that two successively dispensed droplets do not touch one another when making contact with the substrate;

Process 3:
(i) while a tip of the needle of the syringe is located at a Z-level above a surface of a substrate, positioning the needle to an XY dispensing location;
(ii) lowering the needle until contact with the substrate is made;
(iii) raising the needle above the surface of the substrate by an amount that is less than a diameter of an unreleased droplet;
(iv) operating the syringe to dispense a droplet having a defined fluid volume, containing a known concentration of at least one of the at least one material of interest, such that the volume comes in contact with the substrate prior to losing contact with the needle;
(v) lifting the needle in Z away from the substrate, wherein the release of the droplet from the needle to the substrate occurs during a step selected from the group consisting of: step (iv) as the droplet is being dispensed and step (v) as the needle is being lifted away from the substrate; and
(vi) repeating (i) to (v) to dispense at least one droplet at each of a plurality of locations;

Process 4:
steps (i)-(vi) of Process 3 wherein each of a plurality of successive XY droplet dispensing locations is spaced from an immediately preceding XY droplet dispensing location by a distance such that two successively dispensed droplets do not touch one another when making contact with the substrate;

Process 5:
  (i) while a tip of the needle of the syringe is located at a Z-level above a surface of a substrate, positioning the needle to an XY dispensing location;
  (ii) lowering the needle until the tip of the needle is located above the substrate by a distance that is less than a diameter of a droplet to be dispensed;
  (iii) operating the syringe to dispense a droplet having a defined fluid volume, containing a known concentration of at least one of the at least one material of interest, such that the volume comes in contact with the substrate prior to losing contact with the needle;
  (iv) lifting the needle along the Z direction, wherein the release of the droplet from the needle to the substrate occurs during a step selected from the group consisting of step (iii) as the droplet is being dispensed and step (iv) as the needle is being lifted away from the substrate; and
  (v) repeating (i) to (iv) to dispense at least one droplet at each of a plurality of locations;

Process 6:
  Steps (i)-(v) of Process 5 wherein each of a plurality of successive XY droplet dispensing locations is spaced from an immediately preceding XY droplet dispensing location by a distance such that two successively dispensed droplets do not touch one another when making contact with the substrate;

Process 7:
  (i) while a tip of the needle of the syringe is located at a Z-level above a surface of a substrate, positioning the needle to an XY dispensing location;
  (ii) operating the syringe to dispense a droplet having a defined fluid volume containing a known concentration of at least one of the at least one material of interest;
  (iii) lowering the needle until the tip of the needle is located above the substrate by a distance that is less than a diameter of the dispensed droplet;
  (iv) lifting the needle along the Z direction, wherein the release of the droplet from the needle to the substrate occurs during a step selected from the group consisting of: step (ii), step (iii), and step (iv); and
  (v) repeating (i) to (iv) to dispense at least one droplet at each of a plurality of locations; and Process 8:
  Steps (i)-(v) of Process 7 wherein each of a plurality of successive XY droplet dispensing locations is spaced from an immediately preceding XY droplet dispensing location by a distance such that two successively dispensed droplets do not touch one another when making contact with the substrate.

9. The method of claim 7 wherein droplets have a property selected from the group consisting of: (1) a nominal diameter of each of a plurality of unreleased droplets being selected from a group consisting of: (i) between 0.05 mm and 5 mm, (ii) between 0.1 mm and 3 mm, and (iii) between 0.1 and 1 mm; and (2) a nominal diameter of each of a plurality of deposited droplets being selected from a group consisting of: (i) between 0.1 mm and 5 mm, (ii) between 0.2 mm and 2 mm, and (iii) between 0.5 and 1.5 mm.

10. The method of claim 2 wherein a spacing between a plurality of successive XY dispensing locations is selected from a group consisting of: (1) between 0.1 mm and 10 mm, (2) between 0.2 mm and 5 mm, and (3) between 0.5 mm and 1.2 mm.

11. The method of claim 2 wherein the at least one location has a measurement diameter selected from a group consisting of: (1) between 0.5 mm and 15 mm, (2) between 1 mm and 10 mm, (3) between 1 mm and 5 mm, and (4) between 2.0 mm and 4.0 mm.

12. The method of claim 2 wherein the at least one set of sample calibration surfaces has an attribute selected from the group consisting of: (1) not being destroyed in the process of providing a calibration of the instrument; (2) being used after the instrument provides at least one indication using the original calibration information to confirm that the instrument remains within an acceptable calibration tolerance, wherein the acceptable calibration tolerance is selected from the group consisting of: (i) 0.5 to 2.0 of the original calibration, (ii) 0.5 to 1.5 of the original calibration, and (iii) 0.75 to 1.25 of the original calibration; (3) each calibration sample is provided with a single concentration of at least one of the at least one material of interest and wherein each such calibration sample surface is provided on its own separate substrate; (4) being provided by a chemical printing device that provides at least one computer-controlled stage for relative XY movement of a printhead carrying a syringe needle and at least one substrate onto which calibration samples are printed; (5) being provided by a chemical printing device that provides at least one computer-controlled stage for relative XY movement of a printhead carrying the syringe needle and at least one substrate onto which calibration samples are printed and wherein the XY position of the printhead is confirmed periodically by running the printhead that carries a syringe needle back to a known position after which, at least one control parameter is reset to a selected value; and (6) wherein calibration samples are printed directly onto an in-situ surface.

13. The method of claim 2 wherein formation of the plurality of sample calibration surfaces comprises at least one material of interest forming a solution of known concentration after it is dissolved in a solvent and wherein after depositing a droplet of the solution, the solvent evaporates from the at least one material of interest to leave a dried deposit.

14. The method of claim 2 wherein the sample calibration surfaces are created by a chemical printer that is configured to hold multiple samples of liquids with each containing a known concentration-s of the at least one material of interest which can be used by a syringe in depositing different droplets.

15. The method of claim 14 wherein a plurality of droplets are dispensed during the formation of a first calibration sample surface using liquid from one sample container and a plurality of other droplets are dispensed using a liquid from another sample container in forming a calibration sample selected from the group consisting of (1) the first calibration sample and (2) a different calibration sample.

16. The method of claim 15 wherein prior to using the syringe to hold and dispense a second material of interest of at least two different materials, the syringe is purged of a first material of interest and rinsed prior to taking in a quantity of the second material of interest that will be used in forming a calibration sample.

17. The method of claim 16 wherein the purging and rinsing comprises: (1) emptying the first material from the syringe into a waste receptacle, (2) loading a third liquid into the syringe at least once and emptying the syringe of the third liquid prior to loading in a liquid containing the second material that will be used in making a calibration sample surface, wherein the third liquid is selected from the group consisting of: (1) a solvent, and (2) a fluid containing the same material as the second material of interest but extracted from a different container to avoid contamination.

18. The method of claim 2 wherein the spectroscopic surface analysis instrument is calibrated to provide a quantitative indication a material of interest that exists in chemical handling equipment in a chemical handling facility selected from the group consisting of: (1) a pharmaceutical processing facility, (2) a food processing facility, (3) an explosives processing facility, (4) a nanoparticle processing facility, (5) a semiconductor processing facility, and (6) a research laboratory; and wherein the chemical handling facility further comprises a facility selected from the group consisting of: (1) a manufacturing facility, (2) a packaging facility, and (3) a transportation facility; and wherein the chemical handling equipment comprises a chemical handling machine selected from the group consisting of: (1) an ingredient processing machine, (2) an ingredient mixing machine, (3) a packaging machine, (4) a transportation machine, (5) a vehicle, and (6) a dispensing machine.

19. The method of claim 2 wherein at least one of the at least one material of interest comprises a material selected from the group consisting of: (1) an active pharmaceutical ingredient (API), (2) an excipient, (3) a pharmaceutical drug, (4) a food, (5) a food ingredient, (6) an explosive, (7) an explosive ingredient, (8) a toxic material, (9) a bacteria, (10) a virus, (11) cleaning material, and (12) an organic material.

20. The method of claim 2 wherein the excitation radiation has a wavelength selected from the group consisting of: (1) less than 350 nm, (2) less than 300 nm, (3) less than 280 nm, and (4) less than 250 nm; and wherein the emission radiation comprises radiation selected from the group consisting of: (1) fluorescence emission from a doping source; (2) native fluorescence emission, (3) phosphorescence emission, (4) Raman emission, and (5) non-absorbed radiation.

* * * * *